US012799135B2

(12) United States Patent
Huang et al.

(10) Patent No.: US 12,799,135 B2
(45) Date of Patent: Nov. 17, 2026

(54) CEPHALOSPORIN ANTIBACTERIAL COMPOUND AND PHARMACEUTICAL APPLICATION THEREOF

(71) Applicants: SHANGHAI SENHUI MEDICINE CO., LTD., Shanghai (CN); SHANGHAI SHENGDI PHARMACEUTICAL CO., LTD., Shanghai (CN); JIANGSU HENGRUI MEDICINE CO., LTD., Lianyungang (CN)

(72) Inventors: Jian Huang, Shanghai (CN); Lingjian Zhu, Shanghai (CN); Yang Zou, Shanghai (CN); Cili Zhang, Shanghai (CN)

(73) Assignees: Senhui Medicine Co., Ltd., Shanghai (CN); Shanghai Shengdi Pharmaceutical Co., Ltd., Shanghai (CN); Jiangsu Hengrui Medicine Co., Ltd., Lianyungang (CN)

( * ) Notice: Subject to any disclaimer, the term of this patent is extended or adjusted under 35 U.S.C. 154(b) by 1042 days.

(21) Appl. No.: 17/759,232

(22) PCT Filed: Jan. 22, 2021

(86) PCT No.: PCT/CN2021/073242

§ 371 (c)(1),
(2) Date: Jul. 21, 2022

(87) PCT Pub. No.: WO2021/147986

PCT Pub. Date: Jul. 29, 2021

(65) Prior Publication Data

US 2023/0121689 A1 Apr. 20, 2023

(30) Foreign Application Priority Data

Jan. 22, 2020 (CN) ........................ 202010073626.0
Feb. 28, 2020 (CN) ........................ 202010128371.3
Sep. 14, 2020 (CN) ........................ 202010961434.3
Oct. 10, 2020 (CN) ........................ 202011079522.7

(51) Int. Cl.

*C07D 501/46* (2006.01)
*A61K 9/00* (2006.01)
*A61K 31/546* (2006.01)
*A61P 31/04* (2006.01)

(52) U.S. Cl.

CPC .......... *C07D 501/46* (2013.01); *A61K 9/0019* (2013.01); *A61K 31/546* (2013.01); *A61P 31/04* (2018.01)

(58) Field of Classification Search

CPC ............................ A61K 9/0019; A61K 31/546
See application file for complete search history.

(56) References Cited

U.S. PATENT DOCUMENTS

| | | | |
|---|---|---|---|
| 8,883,773 B2 | 11/2014 | Yamawaki | |
| 9,145,425 B2 | 9/2015 | Hisakawa | |
| 9,238,657 B2 | 1/2016 | Nishitani et al. | |
| 9,340,556 B2 | 5/2016 | Liao | |
| 2015/0344502 A1 | 12/2015 | Yamawaki et al. | |
| 2021/0024543 A1 | 1/2021 | Shoji et al. | |

FOREIGN PATENT DOCUMENTS

| | | | |
|---|---|---|---|
| CN | 102203100 | * 9/2011 | ........... C07D 505/24 |
| CN | 102203100 A | 9/2011 | |
| CN | 102918047 A | 2/2013 | |
| CN | 102918048 A | 2/2013 | |
| CN | 104039152 A | 9/2014 | |
| CN | 105073759 | * 11/2015 | ........... C07D 505/24 |
| CN | 105073759 A | 11/2015 | |
| JP | 2015221788 A | 12/2015 | |
| JP | 2016079098 A | 5/2016 | |
| WO | 2010050468 A1 | 5/2010 | |
| WO | 2017216765 A1 | 12/2017 | |
| WO | 2019194306 A1 | 10/2019 | |

OTHER PUBLICATIONS

Euro. Jnal of Med. Chem, vol. 155, pp. 847-868.*
International Search Report issued Apr. 22, 2021 in PCT/CN2021/073242, 10 pages.
Written Opinion issued Apr. 22, 2021 in PCT/CN2021/073242, 14 pages.
Katsu, Kanemasa, et al., "In Vitro Antibacterial Activity of E-0702, a New Semisynthetic Cephalosporin," Antimicrobial Agents and Chemotherapy, vol. 22, No. 2, pp. 181-185, Aug. 1982.
Aoki, Toshiaki, et al., "Cefiderocol (S-649266), A New Siderophore Cephalosporin Exhibiting Potent Activities Against Pseudomonas aeruginosa and Other Gram-Negative Pathogens Including Multi-drug Resistant Bacteria: Structure Activitiy Relationship," Accepted Manuscript European Journal of Medicinal Chemistry, Accepted Jun. 4, 2018.
Xi et al., "Research Progress on Deuterated Drugs," Tianjin Pharmacy, 32(1), total 24 pages (2020).

* cited by examiner

*Primary Examiner* — Paul V Ward
(74) *Attorney, Agent, or Firm* — ICE MILLER LLP

(57) ABSTRACT

Provided are a cephalosporin compound represented by formula I-1, I-2, or I-3, a pharmaceutical composition comprising same, and use thereof as an antibacterial agent.

(I-1)

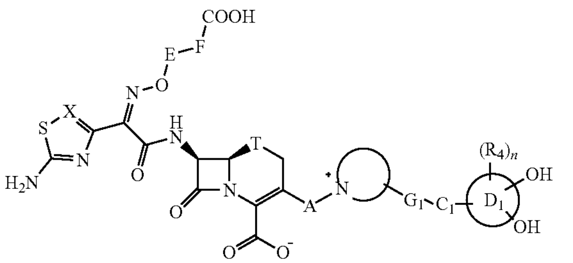

15 Claims, No Drawings

CEPHALOSPORIN ANTIBACTERIAL COMPOUND AND PHARMACEUTICAL APPLICATION THEREOF

CROSS-REFERENCE TO RELATED APPLICATION

This application is a Section 371 of International Application No. PCT/CN2021/073242 filed Jan. 22, 2021, which was published in the Chinese language Jul. 29, 2021, under International Publication No. WO 2021/147986 A1, which claims priority to CN 202010073626.0 filed Jan. 22, 2020; CN 202010128371.3 filed Feb. 28, 2020; CN 202010961434.3 filed Sep. 14, 2020; and CN 202011079522.7 filed Oct. 10, 2020, the disclosures of which are incorporated herein by reference in their entireties.

TECHNICAL FIELD

The present disclosure relates to the field of pharmaceutics, and particularly relates to a cephalosporin antibacterial compound and pharmaceutical use thereof.

BACKGROUND

The development of antibacterial treatment regimens has been an ongoing challenge for today's society. The antibacterial agents include various chemically synthesized drugs such as antibiotics, sulfonamides, imidazoles, nitroimidazoles, and quinolones, among which β-lactam antibiotics are a very important class. Up to now, a variety of β-lactamase inhibitors have been reported in literatures or marketed, and they have become extremely important antibacterial agents in clinic. However, resistance to β-lactamase inhibitors is a growing problem, and an increasing number of bacteria have acquired resistance by producing β-lactamases and degrading β-lactamase inhibitors. β-lactamases are mainly classified into 4 types according to the Ambler molecular classification, specifically including A type (TEM type, SHV type, CTX-M type, KPC type, etc.), B type (IMP type, VIM type, L-1 type, etc.), C type (AmpC type), and D type (OXA type, etc.). Among those types, A, C and D types mainly belong to serine-β-lactamases, and B type belongs to metallo-β-lactamases, both having their own different mechanisms in hydrolyzing β-lactamase inhibitors.

The emergence of gram-negative bacteria that become highly resistant to β-lactamase inhibitors (including cephalosporins and carbapenems) by producing A-type or D-type serine β-lactamases and B-type metallo-β-lactamases that extend their substrate spectrum poses a significant clinical problem. It is known that metallo-β-lactamase is one of the causes for gram-negative bacteria to acquire multi-drug resistance, however, the development of compounds with more effective antibacterial activity, especially cephalosporin compounds showing efficacy on gram-negative bacteria producing various β-lactamases, is a challenge in the research field of antibacterial agents today. It has been reported in the literature (*Antimicrob Agents Chemother.* 1982, 22(2), 181-185) that cephalosporin compounds containing a catechol group in the molecule have high activity against gram-negative bacteria. The mechanism of action is that the catechol group in the molecule forms a chelate with extracellular $Fe^{3+}$, so that the compound is effectively incorporated into the bacteria through an $Fe^{3+}$ transport system (tonB-dependent transport system) on the cell membrane. This Trojan horse strategy allows the compound to have higher concentration in the periplasmic space (the narrow space between the outer membrane and the cell wall), and to bind a receptor to inhibit the synthesis of the bacterial cell wall. Therefore, compounds having catechol or a similar structure in the 3-position side chain or 7-position side chain of a cephalosporin skeleton have been studied (EP0416410B1). Cefiderocol is a novel siderophore cephalosporin (WO2010050468, WO2017216765, *Eur. J Med. Chem.* 2018, 155, 847-868), and up to now, Fetroja (cefiderocol) from Shionogi Pharmaceutical has been approved by the FDA (U.S. Food and Drug Administration) for treating complicated urinary tract infection (cUTI) including kidney infections caused by sensitive gram-negative bacteria, in patients aged 18 or older.

SUMMARY

The present disclosure is intended to provide a cephalosporin antibacterial compound capable of exhibiting an effective antibacterial spectrum against gram-negative bacteria, particularly drug-resistant gram-negative bacteria.

In one aspect, the present disclosure provides a compound of formula (I-1) or a pharmaceutically acceptable salt, stereoisomer, rotamer, tautomer or deuterated compound thereof, (I-1)

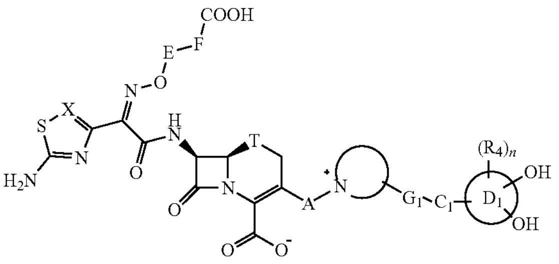

wherein,

X is selected from the group consisting of N, CH and C—Cl;

T is selected from the group consisting of S, S═O, $CH_2$ and O;

E is selected from the group consisting of

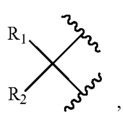

,

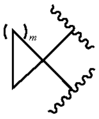

and

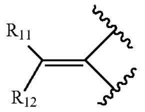

, wherein $R_1$ and $R_2$ are each independently selected from the group consisting of hydrogen, halogen, phenyl, alkylthio, and alkyl optionally substituted with carbamoyl (preferably $C_1$-$C_6$ alkyl, the same applies below); $R_{11}$ and $R_{12}$ are each independently selected from the group consisting of hydrogen, carboxyl, and alkyl optionally substituted with carbamoyl; and m is an integer from 1 to 5;

F is a single bond;

A is selected from the group consisting of alkylene (preferably $C_1$-$C_6$ alkylene, the same applies below), alkenylene (preferably $C_2$-$C_6$ alkenylene, the same applies below) and alkynylene (preferably $C_2$-$C_6$ alkynylene, the same applies below);

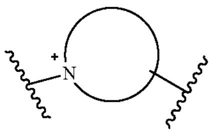

is a quaternary ammonium group containing one or more N atoms and selected from the group consisting of heterocyclyl (preferably 3- to 12-membered, and more preferably 3- to 6-membered, the same applies below), fused heterocyclyl (preferably 6- to 14-membered, and more preferably 7- to 10-membered, the same applies below), heteroaryl (preferably 5- to 12-membered, and more preferably 5- to 8-membered, the same applies below) and fused heteroaryl (preferably 5- to 14-membered, and more preferably 5- to 12-membered, the same applies below), wherein the heterocyclyl, fused heterocyclyl, heteroaryl and fused heteroaryl are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy (preferably $C_1$-$C_6$ alkoxy, the same applies below), alkylthio (preferably $C_1$-$C_6$ alkylthio, the same applies below), cycloalkyl (preferably 3- to 12-membered, and more preferably 3- to 6-membered, the same applies below), heterocyclyl, aryl (preferably 6- to 14-membered, and more preferably 6- to 10-membered, the same applies below), and heteroaryl;

$G_1$ is

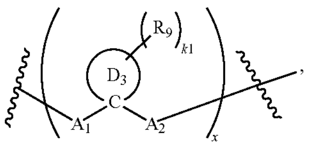

wherein x is an integer from 1 to 6;

$A_1$ is selected from the group consisting of a single bond, alkylene, alkenylene and alkynylene, wherein the alkylene, alkenylene and alkynylene are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

$A_2$ is selected from the group consisting of a single bond, alkylene, alkenylene and alkynylene, wherein the alkylene, alkenylene and alkynylene are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

ring $D_3$ is selected from the group consisting of cycloalkyl, fused cycloalkyl (preferably 6- to 14-membered, and more preferably 7- to 10-membered, the same applies below), heterocyclyl and fused heterocyclyl;

$R_9$ is selected from the group consisting of alkyl, halogen, hydroxy, mercapto, oxo, thio, —$NR_iR_j$, —$C(O)R_k$, —$C(O)OR_k$, nitro, cyano, alkoxy and alkylthio, wherein the alkyl, alkoxy and alkylthio are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy, alkylthio, cycloalkyl, heterocyclyl, aryl and heteroaryl;

k1 is an integer from 0 to 8;

$C_1$ is selected from the group consisting of —O—, —C(=O)—, —C(=O)—C(=O)—, —O—C(=O)—, —C(=O)—O—, —$NR_3$—, —$NR_3$—C(=O)—, —C(=O)—$NR_3$—, —C(=O)—C(=O)—$NR_3$—, —C(=N—$OR_{31}$)—C(=O)—$NR_3$—, —$NR_3$—C(=O)—C(=O)—, —$NR_3$—C(=O)—C(=N—$OR_{31}$)—, —$NR_3$—$NR_3$—C(=O)—, —C(=O)—$NR_3$—$NR_3$—, —N=N—C(=O)—, —C(=O)—N=N—, —C(=O)—$NR_3$—C(=O)—, —$NR_3$—C(=O)—$NR_3$—, —S—, —S(=O)—, —$SO_2$—, —$SO_2$—$NR_3$—, —$NR_3$—$SO_2$—, —$CH_2$—$NR_3$—C(=O)—, —$NR_3$—C(=NH)—, —C(=NH)—$NR_3$—, —$NR_3$—C(=S)—, —C(=S)—$NR_3$—, —$NR_3$—C(=S)—$NR_3$—, —$NR_3$—C(=NH)—$NR_3$—,

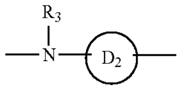

and —$NR_3$—, wherein each $R_3$ is independently selected from the group consisting of hydrogen, hydroxy, alkyl and alkoxy, wherein the alkyl and alkoxy are each independently optionally substituted with one or more substituents selected from the group consisting of alkyl, halogen, hydroxy, mercapto, —$NR_iR_j$,

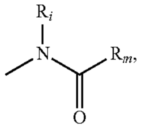

oxo, thio, —$C(O)R_k$, —$C(O)OR_k$, —$C(S)R_k$, nitro, cyano, alkoxy, alkylthio, cycloalkyl, heterocyclyl, aryl and heteroaryl; $R_m$ is selected from the group consisting of hydrogen, alkyl, hydroxy, aryl and heteroaryl, wherein the alkyl, aryl and heteroaryl are each independently optionally substituted with one or more substituents selected from the group consisting of alkyl, halogen, hydroxy, mercapto, —$NR_iR_j$, carboxyl, nitro, cyano, alkoxy, alkylthio, cycloalkyl, heterocyclyl, aryl and heteroaryl; $R_{31}$ is hydrogen or alkyl; and ring $D_2$ is heterocyclyl or heteroaryl;

ring $D_1$ is selected from the group consisting of aryl, fused cycloaryl (preferably 8- to 14-membered, and more preferably 8- to 12-membered, the same applies below), heterocyclyl, fused heterocyclyl, heteroaryl and fused heteroaryl;

each $R_4$ is independently selected from the group consisting of alkyl, halogen, hydroxy, mercapto, oxo, thio, —$NR_iR_j$, —$C(O)R_k$, —$C(O)OR_k$, nitro, cyano, alkoxy and alkylthio, wherein the alkyl, alkoxy and alkylthio are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy, alkylthio, cycloalkyl, heterocyclyl, aryl and heteroaryl;

n is an integer from 0 to 8;

$R_i$ and $R_j$ are each independently selected from the group consisting of hydrogen, hydroxy, $C_1$-$C_6$ alkyl and $C_1$-$C_6$ alkoxy; and each $R_k$ is independently selected from the group consisting of hydrogen, alkyl, haloalkyl, alkoxy, hydroxy and —$NR_iR_j$, wherein the alkyl, haloalkyl and alkoxy are each independently optionally substituted with one or more substituents selected from the group consisting of alkyl, halogen, hydroxy, mercapto, —$NR_iR_j$, oxo, thio, carboxyl, nitro, cyano, alkoxy, alkylthio, cycloalkyl, heterocyclyl, aryl and heteroaryl.

The "C" in the formula is a carbon atom.

In certain embodiments, E is

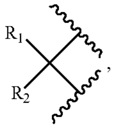

wherein $R_1$ and $R_2$ are each independently selected from the group consisting of hydrogen, halogen, and alkyl optionally substituted with carbamoyl.

In certain embodiments,

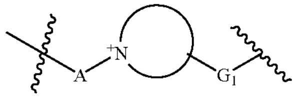

is selected from the group consisting of:

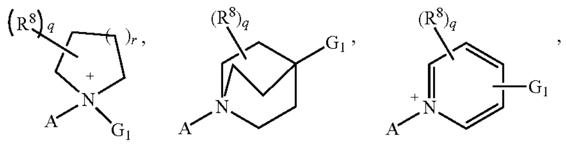

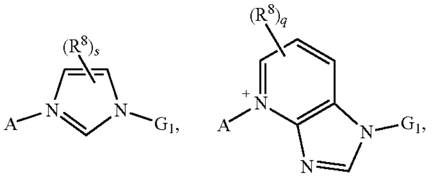

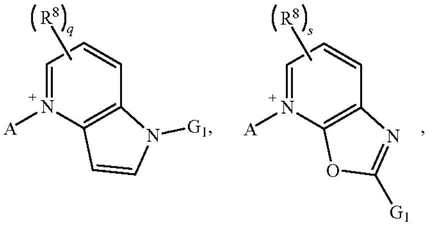

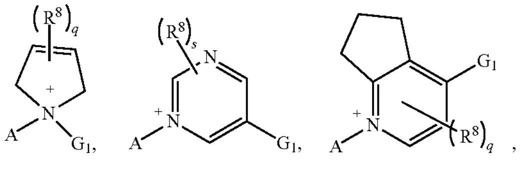

-continued

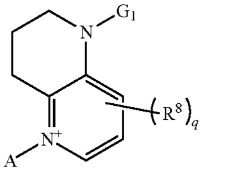

and

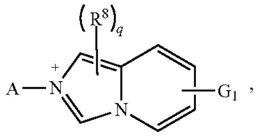

wherein each $R_8$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy;
each q is independently an integer from 0 to 5;
each r is independently an integer from 0 to 5; and
each s is independently an integer from 0 to 3.
In certain embodiments,

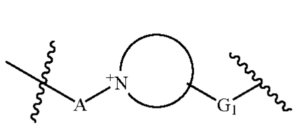

is

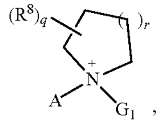

wherein each $R_8$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy, q is an integer from 0 to 5, and R is an integer from 0 to 5.

In certain embodiments $G_1$ is selected from the group consisting of:

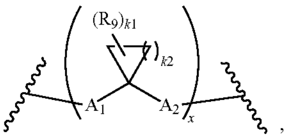

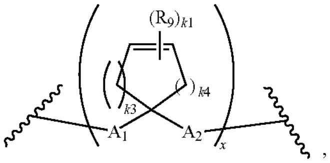

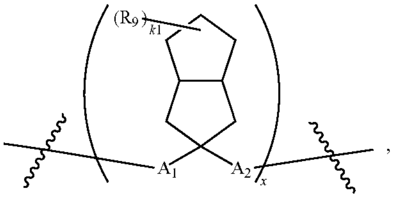

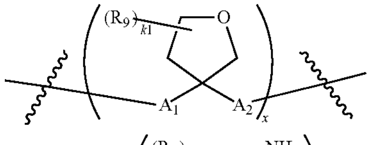

and

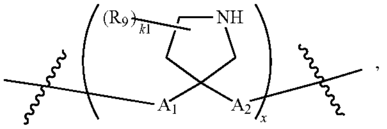

wherein each $R_9$ is independently selected from the group consisting of halogen, hydroxy, alkyl, alkoxy, haloalkyl and haloalkoxy;
each k2 is independently an integer from 1 to 6;
each k3 is independently an integer from 0 to 3; and
each k4 is independently an integer from 0 to 3.

In certain embodiments, each $R_9$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy;

$A_1$ is a single bond or $C_1$-$C_6$ alkylene, wherein the alkylene is optionally substituted with one or more substituents selected from the group consisting of $C_1$-$C_6$ alkyl, halogen, hydroxy, mercapto, —$NR_iR_j$, oxo, thio, —$C(O)R_k$, —$C(O)OR_k$, —$C(S)R_k$, nitro, cyano, $C_1$-$C_6$ alkoxy and $C_1$-$C_6$ alkylthio;

$A_2$ is a single bond or $C_1$-$C_6$ alkylene, wherein the alkylene is optionally substituted with one or more substituents selected from the group consisting of $C_1$-$C_6$ alkyl, halogen, hydroxy, mercapto, —$NR_iR_j$, oxo, thio, —$C(O)R_k$, —$C(O)OR_k$, —$C(S)R_k$, nitro, cyano, $C_1$-$C_6$ alkoxy and $C_1$-$C_6$ alkylthio;

each k2 is independently an integer from 1 to 6; each k3 is independently an integer from 0 to 3; each k4 is independently an integer from 0 to 3; and x is an integer from 1 to 3.

In certain embodiments, examples of ring $D_2$ include

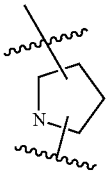 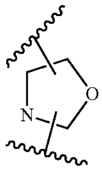 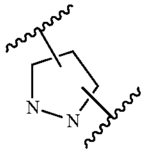
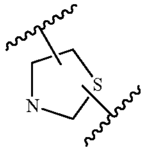 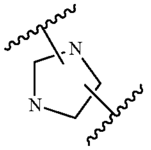 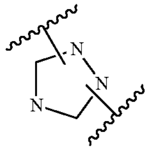
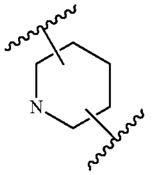 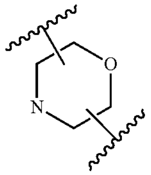 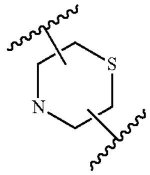
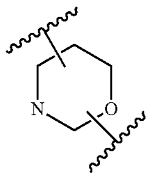, 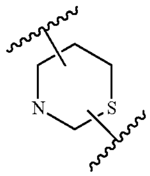 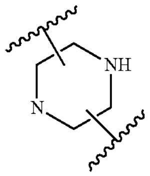
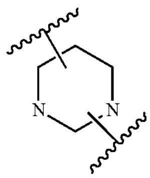 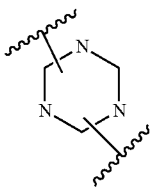 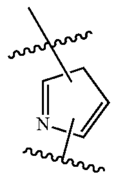
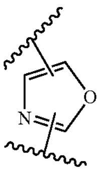 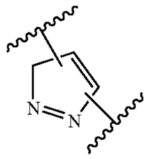 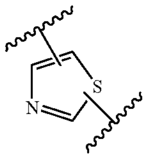

-continued

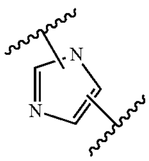 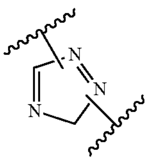 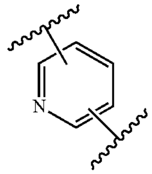
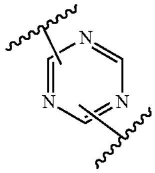 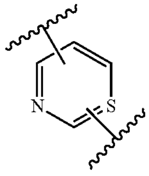 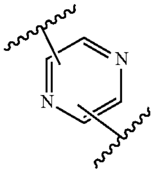
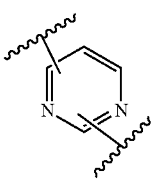 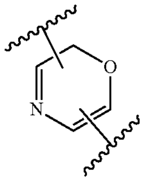
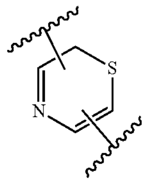 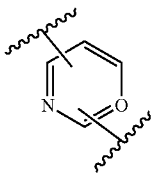.

In certain embodiments, $C_1$ is selected from the group consisting of —$NR_3$—, —$NR_3$—C(═O)—, —$NR_3$—C(═S)—, —$NR_3$—C(═NH)—, —$NR_3$—C(═NH)—$NR_3$—, —$NR_3$—C(═S)—$NR_3$— and

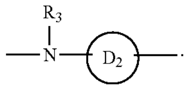.

In certain embodiments, $R_3$ is selected from the group consisting of hydrogen, hydroxy, $C_1$-$C_6$ alkyl and $C_1$-$C_6$ alkoxy, wherein the alkyl and alkoxy are each independently optionally substituted with one or more substituents selected from the group consisting of $C_1$-$C_6$ alkyl, halogen, hydroxy, —$NR_iR_j$,

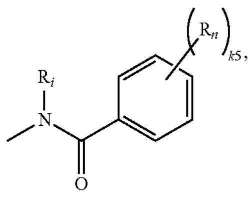

oxo, —$C(O)OR_k$ and cyano; each $R_n$ is independently selected from the group consisting of $C_1$-$C_6$ alkyl, hydroxy and halogen; and k5 is an integer from 0 to 5.

In certain embodiments, wherein

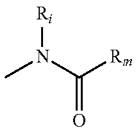 is 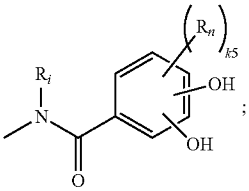 ;

each $R_n$ is independently selected from the group consisting of $C_1$-$C_6$ alkyl, hydroxy and halogen; and k5 is an integer from 0 to 3.

In certain embodiments, ring $D_1$ is phenyl or naphthyl.

In certain embodiments, the compound of formula I-1 is (II-1)

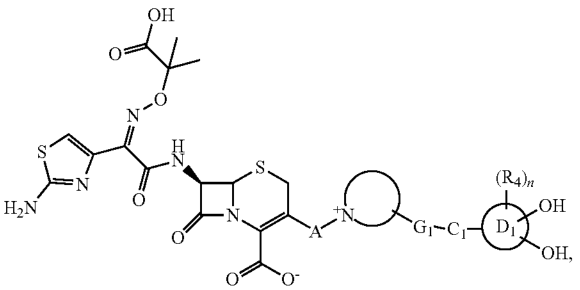

wherein A,

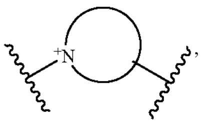

$G_1$, $C_1$, $D_1$, $R_4$ and n are as described above.

In one aspect, the present disclosure provides a compound of formula (I-2) or a pharmaceutically acceptable salt, stereoisomer, rotamer, tautomer or deuterated compound thereof, (I-2)

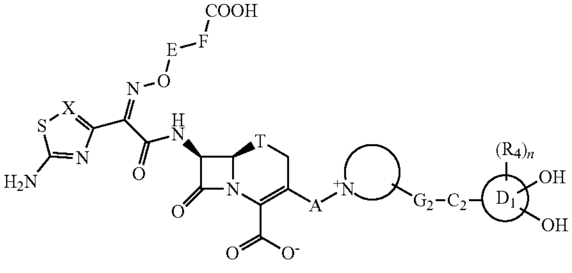

wherein,

X is selected from the group consisting of N, CH and C—Cl;

T is selected from the group consisting of S, S═O, $CH_2$ and O;

E is selected from the group consisting of

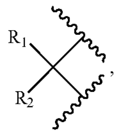 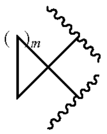 and 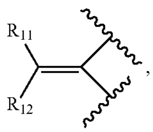

wherein $R_1$ and $R_2$ are each independently selected from the group consisting of hydrogen, halogen, phenyl, alkylthio, and alkyl optionally substituted with carbamoyl (preferably $C_1$-$C_6$ alkyl, the same applies below); $R_{11}$ and $R_{12}$ are each independently selected from the group consisting of hydrogen, carboxyl, and alkyl optionally substituted with carbamoyl; and m is an integer from 1 to 5;

F is a single bond;

A is selected from the group consisting of alkylene (preferably $C_1$-$C_6$ alkylene, the same applies below), alkenylene (preferably $C_2$-$C_6$ alkenylene, the same applies below) and alkynylene (preferably $C_2$-$C_6$ alkynylene, the same applies below);

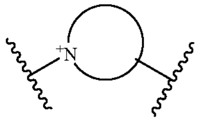

is a quaternary ammonium group containing one or more N atoms and selected from the group consisting of heterocyclyl (preferably 3- to 12-membered, and more preferably 3- to 6-membered, the same applies below), fused heterocyclyl (preferably 6- to 14-membered, and more preferably 7- to 10-membered, the same applies below), heteroaryl (preferably 5- to 12-membered, and more preferably 5- to 8-membered, the same applies below) and fused heteroaryl (preferably 5- to 14-membered, and more preferably 5- to 12-membered, the same applies below), wherein the heterocyclyl, fused heterocyclyl, heteroaryl and fused heteroaryl are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy (preferably $C_1$-$C_6$ alkoxy, the same applies below), alkylthio (preferably $C_1$-$C_6$ alkylthio, the same applies below), cycloalkyl (preferably 3- to 12-membered, and more preferably 3- to 6-membered, the same applies below), heterocyclyl, aryl (preferably 6- to 14-membered, and more preferably 6- to 10-membered, the same applies below), and heteroaryl;

$G_2$ is $G_1$ or alkylene, wherein the alkylene is optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio; and $G_1$ is as described above;

$C_2$ is selected from the group consisting of —$NR_{31}$—C(═O)—, —$NR_3$—C(═O)—$R_{33}$—, —C(═O)—$NR_{31}$—, —C(═O)—C(═O)—$NR_{31}$—, —C(═N—$OR_{32}$)—C(═O)—$NR_{31}$—, —$NR_{31}$—C(═O)—C(═O)—, —$NR_{31}$—C(═O)—C(═N—$OR_{32}$)—, —$NR_3$—C(═NH)—, —C(═NH)—$NR_3$—, —$NR_3$—C(═S)—, —C(═S)—$NR_3$—, —$NR_3$—C(═S)—$NR_3$—, —$NR_3$—C(═NH)—$NR_3$—, —$NR_3$— and

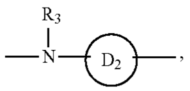

wherein each $R_3$ is independently selected from the group consisting of hydrogen, hydroxy, alkyl and alkoxy, wherein the alkyl and alkoxy are each independently optionally substituted with one or more substituents selected from the group consisting of alkyl, halogen, hydroxy, mercapto, —$NR_iR_j$,

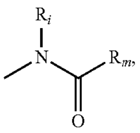

-oxo, thio, —$C(O)R_k$, —$C(O)OR_k$, —$C(S)R_k$, nitro, cyano, alkoxy, alkylthio, cycloalkyl, heterocyclyl, aryl and heteroaryl; $R_m$ is selected from the group consisting of hydrogen, alkyl, hydroxy, aryl and heteroaryl, wherein the alkyl, aryl and heteroaryl are each independently optionally substituted with one or more substituents selected from the group consisting of alkyl, halogen, hydroxy, mercapto, —$NR_iR_j$, carboxyl, nitro, cyano, alkoxy, alkylthio, cycloalkyl, heterocyclyl, aryl and heteroaryl; each $R_{31}$ is independently selected from the group consisting of hydroxy, alkyl and alkoxy, wherein the alkyl and alkoxy are each independently optionally substituted with one or more substituents selected from the group consisting of alkyl, halogen, hydroxy, mercapto, —$NR_iR_j$,

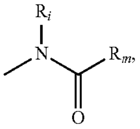

oxo, thio, —$C(O)R_k$, —$C(O)OR_k$, —$C(S)R_k$, nitro, cyano, alkoxy, alkylthio, cycloalkyl, heterocyclyl, aryl and heteroaryl; $R_{32}$ is hydrogen or alkyl; ring $D_2$ is as described above; and $R_{33}$ is selected from the group consisting of optionally substituted alkylene, optionally substituted alkenylene, and optionally substituted alkynylene;

ring $D_1$ is selected from the group consisting of aryl, fused cycloaryl (preferably 8- to 14-membered, and more preferably 8- to 12-membered, the same applies below), heterocyclyl, fused heterocyclyl, heteroaryl and fused heteroaryl;

each $R_4$ is independently selected from the group consisting of alkyl, halogen, hydroxy, mercapto, oxo, thio, —$NR_iR_j$, —$C(O)R_k$, —$C(O)OR_k$, nitro, cyano, alkoxy and alkylthio, wherein the alkyl, alkoxy and alkylthio are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy, alkylthio, cycloalkyl, heterocyclyl, aryl and heteroaryl;

n is an integer from 0 to 8;

$R_i$ and $R_j$ are each independently selected from the group consisting of hydrogen, hydroxy, $C_1$-$C_6$ alkyl and $C_1$-$C_6$ alkoxy; and each $R_k$ is independently selected from the group consisting of hydrogen, alkyl, haloalkyl, alkoxy, hydroxy and —$NR_iR_j$, wherein the alkyl, haloalkyl and alkoxy are each independently optionally substituted with one or more substituents selected from the group consisting of alkyl, halogen, hydroxy, mercapto, —$NR_iR_j$, oxo, thio, carboxyl, nitro, cyano, alkoxy, alkylthio, cycloalkyl, heterocyclyl, aryl and heteroaryl.

In certain embodiments, when $R_{31}$ is alkyl, it is substituted with one or more substituents selected from the group consisting of alkyl, halogen, hydroxy, mercapto, —$NR_iR_j$,

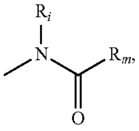

oxo, thio, —$C(O)R_k$, —$C(O)OR_k$, —$C(S)R_k$, nitro, cyano, alkoxy, alkylthio, cycloalkyl, heterocyclyl, aryl and heteroaryl.

In certain embodiments, E is

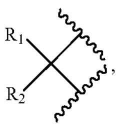

wherein $R_1$ and $R_2$ are each independently selected from the group consisting of hydrogen, halogen, and alkyl optionally substituted with carbamoyl.

In certain embodiments, wherein

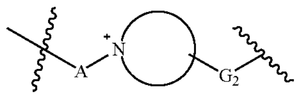

is selected from the group consisting of:

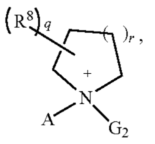,
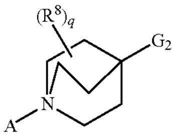,
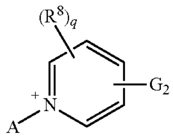,
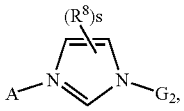,
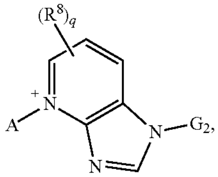,
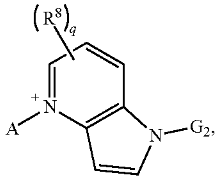,
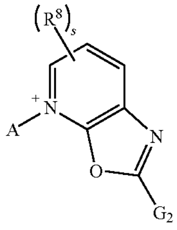, -continued

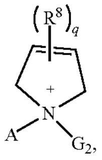

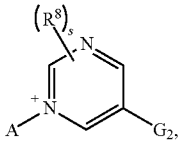

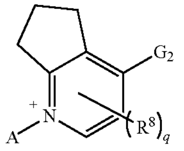

,

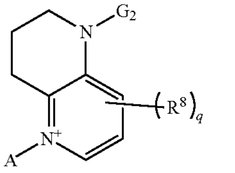

and

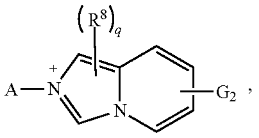

, wherein each $R_8$ is independently selected from the group consisting of hydrogen, halogen, hydroxy, alkyl, alkoxy, haloalkyl and haloalkoxy;

each q is independently an integer from 0 to 5;

each r is independently an integer from 0 to 5; and each s is independently an integer from 0 to 3.

In certain embodiments,

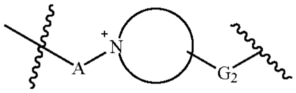

is

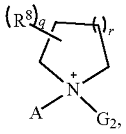

wherein each $R_8$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy, q is an integer from 0 to 5, and R is an integer from 0 to 5.

In certain embodiments, $G_2$ is selected from the group consisting of:

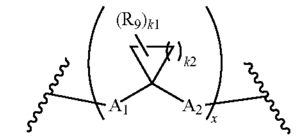

,

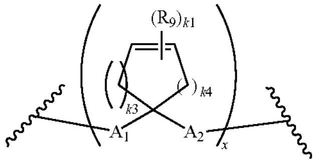

,

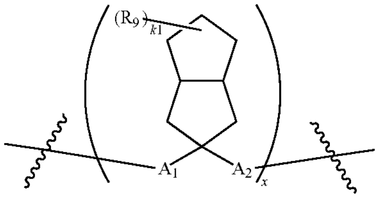

,

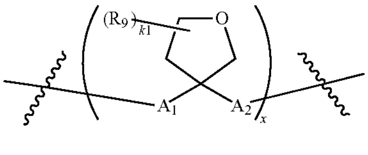

and

-continued

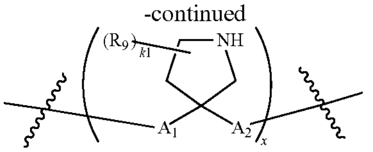

, wherein each $R_9$ is independently selected from the group consisting of halogen, hydroxy, alkyl, alkoxy, haloalkyl and haloalkoxy;

each k2 is independently an integer from 1 to 6;

each k3 is independently an integer from 0 to 3; and each k4 is independently an integer from 0 to 3.

In certain embodiments, each $R_9$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy;

$A_1$ is a single bond or $C_1$-$C_6$ alkylene, wherein the alkylene is optionally substituted with one or more substituents selected from the group consisting of $C_1$-$C_6$ alkyl, halogen, hydroxy, mercapto, —$NR_iR_j$, oxo, thio, —$C(O)R_k$, —$C(O)OR_k$, —$C(S)R_k$, nitro, cyano, $C_1$-$C_6$ alkoxy and $C_1$-$C_6$ alkylthio;

$A_2$ is a single bond or $C_1$-$C_6$ alkylene, wherein the alkylene is optionally substituted with one or more substituents selected from the group consisting of $C_1$-$C_6$ alkyl, halogen, hydroxy, mercapto, —$NR_iR_j$, oxo, thio, —$C(O)R_k$, —$C(O)OR_k$, —$C(S)R_k$, nitro, cyano, $C_1$-$C_6$ alkoxy and $C_1$-$C_6$ alkylthio;

each k2 is independently an integer from 1 to 6; each k3 is independently an integer from 0 to 3; each k4 is independently an integer from 0 to 3; and x is an integer from 1 to 3.

In certain embodiments, wherein $G_2$ is $C_1$-$C_6$ alkylene optionally substituted with one or more substituents selected from the group consisting of $C_1$-$C_6$ alkyl, halogen, hydroxy, mercapto, —$NR_iR_j$, oxo, thio, —$C(O)R_k$, —$C(O)OR_k$, —$C(S)R_k$, nitro, cyano, $C_1$-$C_6$ alkoxy and $C_1$-$C_6$ alkylthio.

In certain embodiments, $C_2$ is selected from the group consisting of —$NR_3$—, —$NR_{31}$—C(=O)—, —$NR_3$—C(=S)—, —$NR_3$—C(=NH)—, —$NR_3$—C(=NH)—$NR_3$—, —$NR_3$—C(=S)—$NR_3$— and

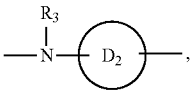

, preferably —$NR_{31}$—C(=O)— or —$NR_3$—C(=S)—.

In certain embodiments, $R_3$ is selected from the group consisting of hydrogen, hydroxy, alkyl and alkoxy, wherein the alkyl and alkoxy are each independently optionally substituted with one or more substituents selected from the group consisting of alkyl, halogen, hydroxy, —$NR_iR_j$,

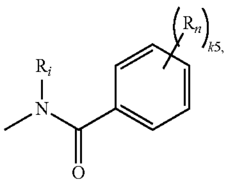

oxo, —$C(O)OR_k$ and cyano; each $R_n$ is independently selected from the group consisting of alkyl, hydroxy and halogen; and k5 is an integer from 0 to 5.

In certain embodiments, $R_{31}$ is selected from the group consisting of hydroxy, alkyl and alkoxy, wherein the alkyl and alkoxy are each independently optionally substituted with one or more substituents selected from the group consisting of alkyl, halogen, hydroxy, —$NR_iR_j$,

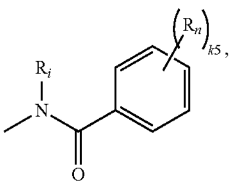

oxo, —$C(O)OR_k$ and cyano; each $R_n$ is independently selected from the group consisting of alkyl, hydroxy and halogen; and k5 is an integer from 0 to 5.

In certain embodiments, $R_{31}$ is selected from the group consisting of hydroxy, $C_1$-$C_6$ alkyl substituted with a substituent, and $C_1$-$C_6$ alkoxy optionally substituted with a substituent, wherein the substituent is selected from the group consisting of one or more of $C_1$-$C_6$ alkyl, halogen, hydroxy, —$NR_iR_j$,

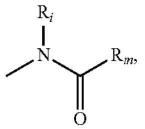

oxo, —$C(O)OR_k$ and cyano.

In certain embodiments, the compound of formula (I-2) is (II-2)

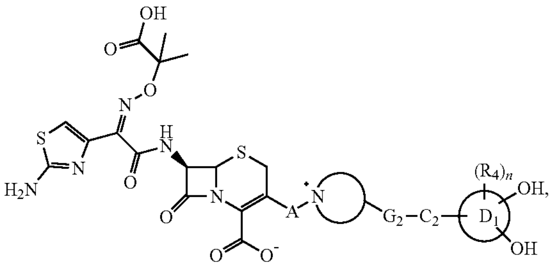

wherein A,

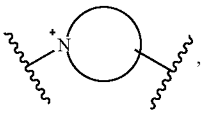

$G_2$, $C_2$, $D_1$, $R_4$ and n are as described above.

In one aspect, the present disclosure provides a compound of formula (I-3) or a pharmaceutically acceptable salt, stereoisomer, rotamer, tautomer or deuterated compound thereof, (I-3)

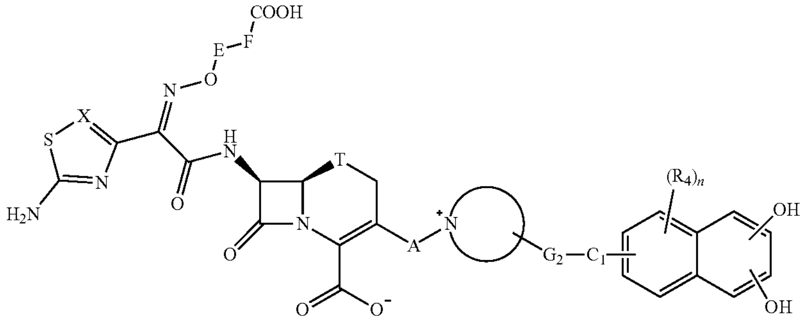

In certain embodiments, wherein

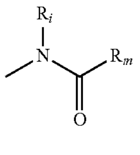

is

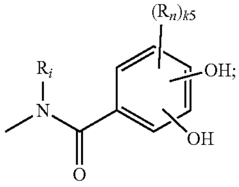

each $R_n$ is independently selected from the group consisting of $C_1$-$C_6$ alkyl, hydroxy and halogen; and k5 is an integer from 0 to 3.

In certain embodiments, ring $D_1$ is phenyl or naphthyl.

wherein,

X is selected from the group consisting of N, CH and C—Cl;

T is selected from the group consisting of S, S═O, $CH_2$ and O;

E is selected from the group consisting of

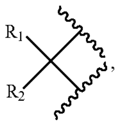

,

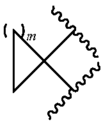

and

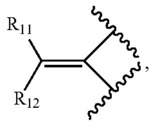

, wherein $R_1$ and $R_2$ are each independently selected from the group consisting of hydrogen, halogen, phenyl, alkylthio, and alkyl optionally substituted with carbamoyl (preferably $C_1$-$C_6$ alkyl, the same applies below); $R_{11}$ and $R_{12}$ are each independently selected from the group consisting of hydrogen, carboxyl, and alkyl optionally substituted with carbamoyl; and m is an integer from 1 to 5;

F is a single bond;

A is selected from the group consisting of alkylene (preferably $C_1$-$C_6$ alkylene, the same applies below), alkenylene (preferably $C_2$-$C_6$ alkenylene, the same applies below) and alkynylene (preferably $C_2$-$C_6$ alkynylene, the same applies below);

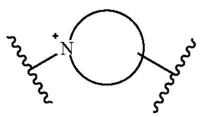

is a quaternary ammonium group containing one or more N atoms and selected from the group consisting of heterocyclyl (preferably 3- to 12-membered, and more preferably 3- to 6-membered, the same applies below), fused heterocyclyl (preferably 6- to 14-membered, and more preferably 7- to 10-membered, the same applies below), heteroaryl (preferably 5- to 12-membered, and more preferably 5- to 8-membered, the same applies below) and fused heteroaryl (preferably 5- to 14-membered, and more preferably 5- to 12-membered, the same applies below), wherein the heterocyclyl, fused heterocyclyl, heteroaryl and fused heteroaryl are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy (preferably $C_1$-$C_6$ alkoxy, the same applies below), alkylthio (preferably $C_1$-$C_6$ alkylthio, the same applies below), cycloalkyl (preferably 3- to 12-membered, and more preferably 3- to 6-membered, the same applies below), heterocyclyl, aryl (preferably 6- to 14-membered, and more preferably 6- to 10-membered, the same applies below), and heteroaryl;

$G_2$ is $G_1$ or alkylene, wherein the alkylene is optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

$G_1$ is

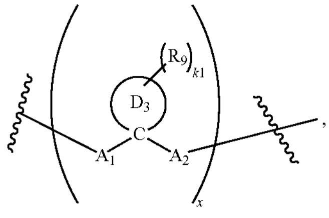, wherein each x is independently an integer from 1 to 6;

$A_1$ is selected from the group consisting of a single bond, alkylene, alkenylene and alkynylene, wherein the alkylene, alkenylene and alkynylene are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

$A_2$ is selected from the group consisting of a single bond, alkylene, alkenylene and alkynylene, wherein the alkylene, alkenylene and alkynylene are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

$D_3$ is selected from the group consisting of cycloalkyl, fused cycloalkyl, heterocyclyl and fused heterocyclyl;

$R_9$ is selected from the group consisting of alkyl, halogen, hydroxy, mercapto, oxo, thio, —$NR_iR_j$, —$C(O)R_k$, —$C(O)OR_k$, nitro, cyano, alkoxy and alkylthio, wherein the alkyl, alkoxy and alkylthio are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy, alkylthio, cycloalkyl, heterocyclyl, aryl and heteroaryl;

k1 is an integer from 0 to 8;

$C_1$ is selected from the group consisting of —O—, —C(=O)—, —C(=O)—C(=O)—, —O—C(=O)—, —C(=O)—O—, —$NR_3$—, —$NR_3$—C(=O)—, —C(=O)—$NR_3$—, —C(=O)—C(=O)—$NR_3$—, —C(=N—$OR_{31}$)—C(=O)—$NR_3$—, —$NR_3$—C(=O)—C(=O)—, —$NR_3$—C(=O)—C(=N—$OR_{31}$)—, —$NR_3$—$NR_3$—C(=O)—, —C(=O)—$NR_3$—$NR_3$—, —N=N—C(=O)—, —C(=O)—N=N—, —C(=O)—$NR_3$—C(=O)—, —$NR_3$—C(=O)—$NR_3$—, —S—, —S(=O)—, —$SO_2$—, —$SO_2$—$NR_3$—, —$NR_3$—$SO_2$—, —$CH_2$—$NR_3$—C(=O)—, —$NR_3$—C(=NH)—, —C(=NH)—$NR_3$—, —$NR_3$—C(=S)—, —C(=S)—$NR_3$—, —$NR_3$—C(=S)—$NR_3$—, —$NR_3$—C(=NH)—$NR_3$—,

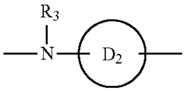

and —$NR_3$—, wherein each $R_3$ is independently selected from the group consisting of hydrogen, hydroxy, alkyl and alkoxy, wherein the alkyl and alkoxy are each independently optionally substituted with one or more substituents selected from the group consisting of alkyl, halogen, hydroxy, mercapto, —$NR_iR_j$,

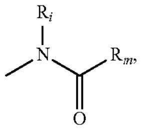

oxo, thio, —$C(O)R_k$, —$C(O)OR_k$, —$C(S)R_k$, nitro, cyano, alkoxy, alkylthio, cycloalkyl, heterocyclyl, aryl and heteroaryl; $R_m$ is selected from the group consisting of hydrogen, alkyl, hydroxy, aryl and heteroaryl, wherein the alkyl, aryl and heteroaryl are each independently optionally substituted with one or more substituents selected from the group consisting of alkyl, halogen, hydroxy, mercapto, —$NR_iR_j$, carboxyl, nitro, cyano, alkoxy, alkylthio, cycloalkyl, heterocyclyl, aryl and heteroaryl; $R_{31}$ is hydrogen or alkyl; and ring $D_2$ is as described above;

each $R_4$ is independently selected from the group consisting of alkyl, halogen, hydroxy, mercapto, oxo, thio, $—NR_iR_j$, $—C(O)R_k$, $—C(O)OR_k$, nitro, cyano, alkoxy and alkylthio, wherein the alkyl, alkoxy and alkylthio are each independently optionally substituted with one or more substituents selected from the group consisting of alkyl, halogen, hydroxy, mercapto, $—NR_iR_j$, oxo, thio, $—C(O)R_k$, $—C(O)OR_k$, $—C(S)R_k$, nitro, cyano, alkoxy, alkylthio, cycloalkyl, heterocyclyl, aryl and heteroaryl;

n is an integer from 0 to 5;

$R_i$ and $R_j$ are each independently selected from the group consisting of hydrogen, hydroxy, $C_1$-$C_6$ alkyl and $C_1$-$C_6$ alkoxy; and $R_k$ is selected from the group consisting of hydrogen, alkyl, haloalkyl, hydroxy and $—NR_iR_j$, wherein the alkyl and haloalkyl are each independently optionally substituted with one or more substituents selected from the group consisting of alkyl, halogen, hydroxy, mercapto, $—NR_iR_j$, oxo, thio, carboxyl, nitro, cyano, alkoxy, alkylthio, cycloalkyl, heterocyclyl, aryl and heteroaryl.

In certain embodiments, E is

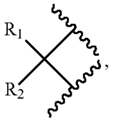

wherein $R_1$ and $R_2$ are each independently selected from the group consisting of hydrogen, halogen, and alkyl optionally substituted with carbamoyl.

In certain embodiments,

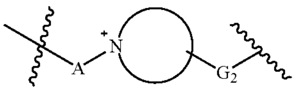

is selected from the group consisting of:

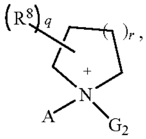 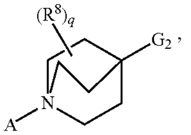 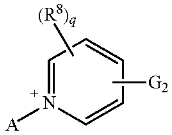,

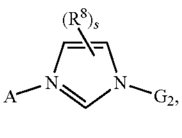 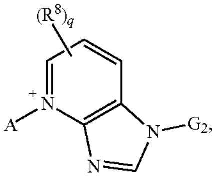

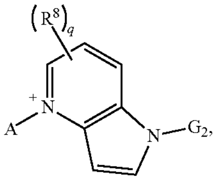 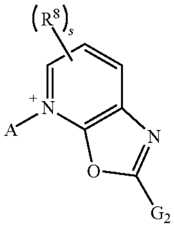,

-continued

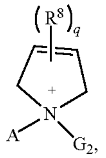 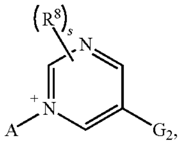 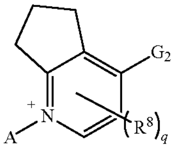,

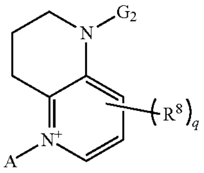 and 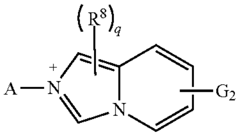, wherein each $R_8$ is independently selected from the group consisting of halogen, hydroxy, alkyl, alkoxy, haloalkyl and haloalkoxy;

each q is independently an integer from 0 to 5;

each r is independently an integer from 0 to 5; and each s is independently an integer from 0 to 3.

In certain embodiments,

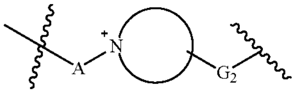 is 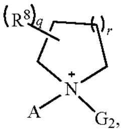

wherein each $R_8$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy, q is an integer from 0 to 5, and R is an integer from 0 to 5.

In certain embodiments, $G_2$ is selected from the group consisting of:

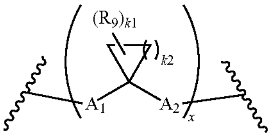,

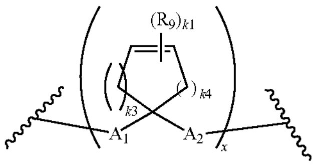,

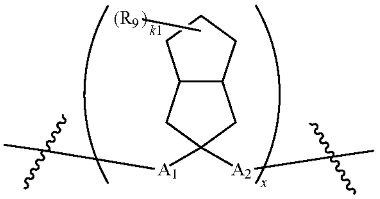,

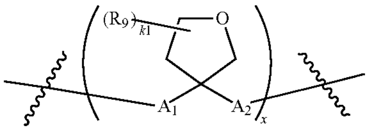 and

-continued

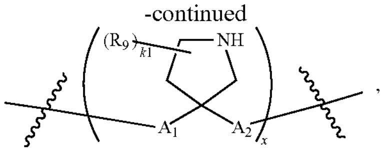

wherein each $R_9$ is independently selected from the group consisting of hydrogen, halogen, hydroxy, alkyl, alkoxy, haloalkyl and haloalkoxy;

each k2 is independently an integer from 1 to 6;

each k3 is independently an integer from 0 to 3; and each k4 is independently an integer from 0 to 3.

In certain embodiments, each $R_9$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy;

$A_1$ is a single bond or $C_1$-$C_6$ alkylene, wherein the alkylene is optionally substituted with one or more substituents selected from the group consisting of $C_1$-$C_6$ alkyl, halogen, hydroxy, mercapto, —$NR_iR_j$, oxo, thio, —C(O)$R_k$, —C(O)O$R_k$, —C(S)$R_k$, nitro, cyano, $C_1$-$C_6$ alkoxy and $C_1$-$C_6$ alkylthio;

$A_2$ is a single bond or $C_1$-$C_6$ alkylene, wherein the alkylene is optionally substituted with one or more substituents selected from the group consisting of $C_1$-$C_6$ alkyl, halogen, hydroxy, mercapto, —$NR_iR_j$, oxo, thio, —C(O)$R_k$, —C(O)O$R_k$, —C(S)$R_k$, nitro, cyano, $C_1$-$C_6$ alkoxy and $C_1$-$C_6$ alkylthio;

each k2 is independently an integer from 1 to 6; each k3 is independently an integer from 0 to 3; each k4 is independently an integer from 0 to 3; and x is an integer from 1 to 3.

In certain embodiments, $G_2$ is $C_1$-$C_6$ alkylene optionally substituted with one or more substituents selected from the group consisting of $C_1$-$C_6$ alkyl, halogen, hydroxy, mercapto, —$NR_iR_j$, oxo, thio, —C(O)$R_k$, —C(O)O$R_k$, —C(S)$R_k$, nitro, cyano, $C_1$-$C_6$ alkoxy and $C_1$-$C_6$ alkylthio.

In certain embodiments, $R_3$ is selected from the group consisting of hydrogen, hydroxy, alkyl and alkoxy, wherein the alkyl and alkoxy are each independently optionally substituted with one or more substituents selected from the group consisting of alkyl, halogen, hydroxy, —$NR_iR_j$,

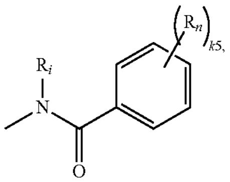

oxo, —C(O)O$R_k$ and cyano; each $R_n$ is independently selected from the group consisting of alkyl, hydroxy and halogen; and k5 is an integer from 0 to 5.

In certain embodiments, wherein

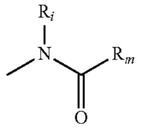

is

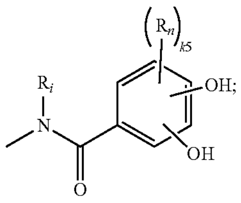

each $R_n$ is independently selected from the group consisting of $C_1$-$C_6$ alkyl, hydroxy and halogen; and k5 is an integer from 0 to 3.

In certain embodiments, the compound of formula (I-3) is (II-3)

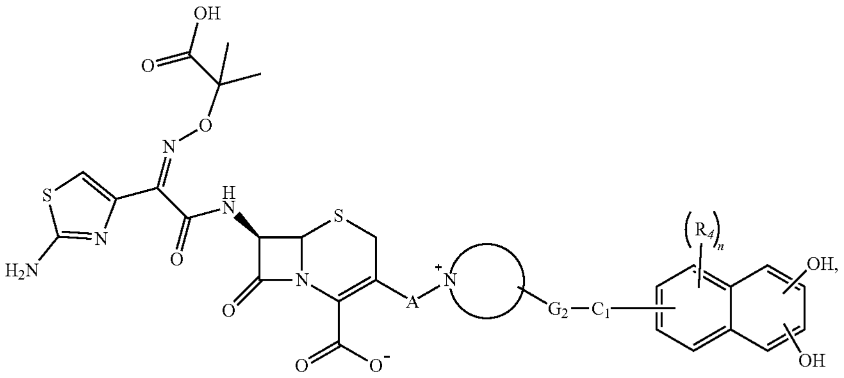

In certain embodiments, $C_1$ is selected from the group consisting of —$NR_3$—, —$NR_3$—C(═O)—, —$NR_3$—C(═S)—, —$NR_3$—C(═NH)—, —$NR_3$—C(═NH)—$NR_3$—, —$NR_3$—C(═S)—$NR_3$— and

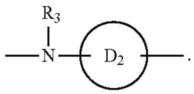

wherein A,

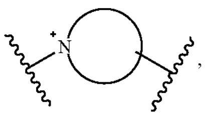

$G_2$, $C_1$, $R_4$ and n are as described above.

In one aspect, the present disclosure provides a compound of formula (I-4) or a pharmaceutically acceptable salt, stereoisomer, rotamer, tautomer or deuterated compound thereof, (I-4)

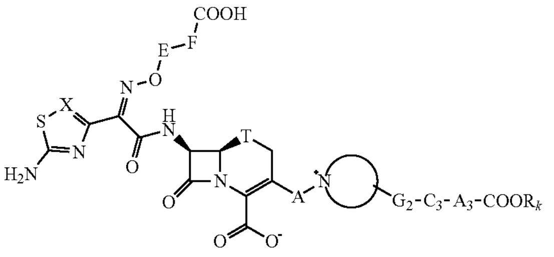

wherein,

X is selected from the group consisting of N, CH and C—Cl;

T is selected from the group consisting of S, S═O, $CH_2$ and O;

E is selected from the group consisting of

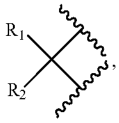,
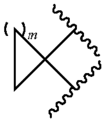
and
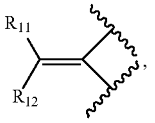, wherein $R_1$ and $R_2$ are each independently selected from the group consisting of hydrogen, halogen, phenyl, alkylthio, and alkyl optionally substituted with carbamoyl (preferably $C_1$-$C_6$ alkyl, the same applies below); $R_{11}$ and $R_{12}$ are each independently selected from the group consisting of hydrogen, carboxyl, and alkyl optionally substituted with carbamoyl; and m is an integer from 1 to 5;

F is a single bond;

A is selected from the group consisting of alkylene (preferably $C_1$-$C_6$ alkylene, the same applies below), alkenylene (preferably $C_2$-$C_6$ alkenylene, the same applies below) and alkynylene (preferably $C_2$-$C_6$ alkynylene, the same applies below);

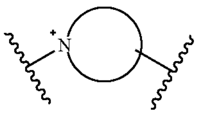

is a quaternary ammonium group containing one or more N atoms and selected from the group consisting of heterocyclyl (preferably 3- to 12-membered, and more preferably 3- to 6-membered, the same applies below), fused heterocyclyl (preferably 6- to 14-membered, and more preferably 7- to 10-membered, the same applies below), heteroaryl (preferably 5- to 12-membered, and more preferably 5- to 8-membered, the same applies below) and fused heteroaryl (preferably 5- to 14-membered, and more preferably 5- to 12-membered, the same applies below), wherein the heterocyclyl, fused heterocyclyl, heteroaryl and fused heteroaryl are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy (preferably $C_1$-$C_6$ alkoxy, the same applies below), alkylthio (preferably $C_1$-$C_6$ alkylthio, the same applies below), cycloalkyl (preferably 3- to 12-membered, and more preferably 3- to 6-membered, the same applies below), heterocyclyl, aryl (preferably 6- to 14-membered, and more preferably 6- to 10-membered, the same applies below), and heteroaryl;

$G_2$ is as described above;

$C_3$ is selected from the group consisting of a single bond, —O—, —C(═O)—, —C(═O)—C(═O)—, —O—C(═O)—, —C(═O)—O—, —$NR_3$—, —$NR_3$—C(═O)—, —C(═O)—$NR_3$—, —C(═O)—C(═O)—$NR_3$—, —C(═N—$OR_{31}$)—C(═O)—$NR_3$—, —$NR_3$—C(═O)—C(═O)—, —$NR_3$—C(═O)—C(═N—$OR_{31}$)—, —$NR_3$—$NR_3$—C(═O)—, —C(═O)—$NR_3$—$NR_3$—, —N═N—C(═O)—, —C(═O)—N═N—, —C(═O)—$NR_3$—C(═O)—, —$NR_3$—C(═O)—$NR_3$—, —O—, —S—, —S(═O)—, —$SO_2$—, —$SO_2$—$NR_3$—, —$NR_3$—$SO_2$—, —$CH_2$—$NR_3$—C(═O)—, —$NR_3$—C(═NH)—, —C(═NH)—$NR_3$—, —$NR_3$—C(═S)—, —C(═S)—$NR_3$—, —$NR_3$—C(═S)—$NR_3$—, —$NR_3$—C(═NH)—$NR_3$—,

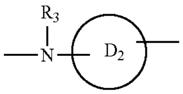

and —$NR_3$—, wherein each $R_3$ is independently selected from the group consisting of hydrogen, hydroxy, alkyl and alkoxy, wherein the alkyl and alkoxy are each independently optionally substituted with one or more substituents selected from the group consisting of alkyl, halogen, hydroxy, mercapto, —$NR_iR_j$,

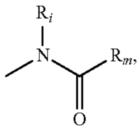

oxo, thio, —$C(O)R_k$, —$C(O)OR_k$, —$C(S)R_k$, nitro, cyano, alkoxy, alkylthio, cycloalkyl, heterocyclyl, aryl and heteroaryl; $R_m$ is selected from the group consisting of hydrogen, alkyl, hydroxy, aryl and heteroaryl, wherein the alkyl, aryl and heteroaryl are each independently optionally substituted with one or more substituents selected from the group consisting of alkyl, halogen, hydroxy, mercapto, —$NR_iR_j$, carboxyl, nitro, cyano, alkoxy, alkylthio, cycloalkyl, heterocyclyl, aryl and heteroaryl; $R_{31}$ is hydrogen or alkyl; and ring $D_2$ is as described above;

$A_3$ is selected from the group consisting of alkylene, alkenylene and alkynylene, wherein the alkylene, alkenylene and alkynylene are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

$R_i$ and $R_j$ are each independently hydrogen or $C_1$-$C_6$ alkyl; and each $R_k$ is independently selected from the group consisting of hydrogen, alkyl, haloalkyl, hydroxy and —$NR_iR_j$, wherein the alkyl and haloalkyl are each independently optionally substituted with one or more substituents selected from the group consisting of alkyl, halogen, hydroxy, mercapto, —$NR_iR_j$, oxo, thio, carboxyl, nitro, cyano, alkoxy, alkylthio, cycloalkyl, heterocyclyl, aryl and heteroaryl.

In certain embodiments, E is

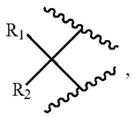

wherein $R_1$ and $R_2$ are each independently selected from the group consisting of hydrogen, halogen, and alkyl optionally substituted with carbamoyl.

In certain embodiments,

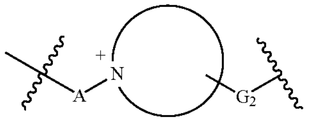

is selected from the group consisting of:

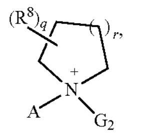

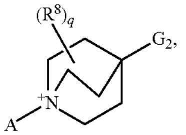

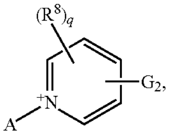

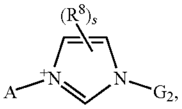

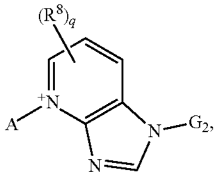

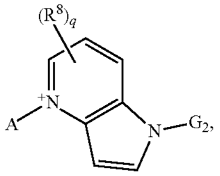

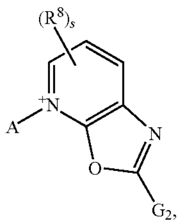

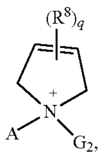

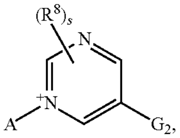

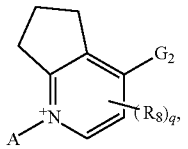

-continued

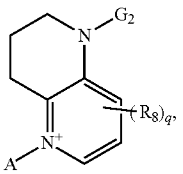

and

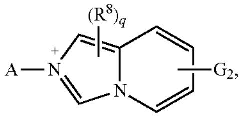

wherein each $R_8$ is independently selected from the group consisting of hydrogen, halogen, hydroxy, alkyl, alkoxy, haloalkyl and haloalkoxy;

each q is independently an integer from 0 to 5;

each r is independently an integer from 0 to 5; and each s is independently an integer from 0 to 3.

In certain embodiments, $C_3$ is selected from the group consisting of a single bond, —$NR_3$—, —$NR_3$—C(=O)—, —$NR_3$—C(=S)—, —$NR_3$—C(=NH)—, —$NR_3$—C(=NH)—$NR_3$—, —$NR_3$—C(=S)—$NR_3$—,

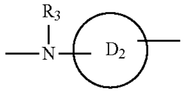

and —$NR_3$—.

In certain embodiments, $R_3$ is selected from the group consisting of hydrogen, hydroxy, alkyl and alkoxy, wherein the alkyl and alkoxy are each independently optionally substituted with one or more substituents selected from the group consisting of alkyl, halogen, hydroxy, —$N_iR_j$,

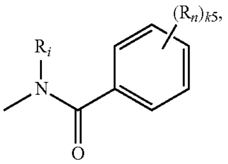

oxo, —C(O))$R_k$ and cyano; $R_n$ is selected from the group consisting of hydrogen, alkyl, hydroxy and halogen; and k5 is an integer from 0 to 5.

In certain embodiments, formula —$C_3$-$A_3$-$COOR_k$ is

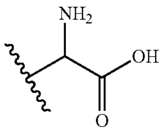

or

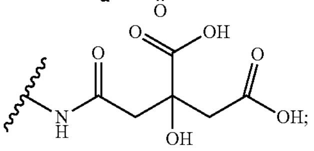

In certain embodiments, the compound of formula (I-4) is (II-4)

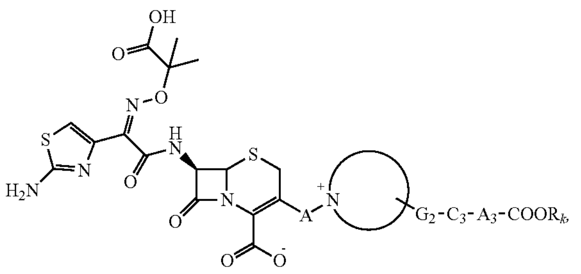

wherein A,

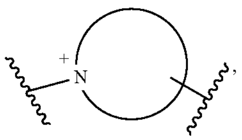

$G_2$, $C_3$, $A_3$ and $R_k$ are as described above.

In another aspect, the present disclosure provides a compound of formula (I-5), or a pharmaceutically acceptable salt, stereoisomer, rotamer, tautomer or deuterated compound thereof, (I-5)

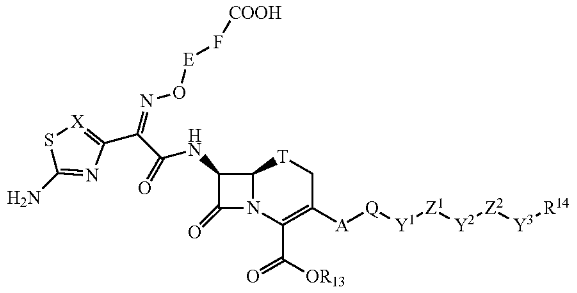

wherein,

X is selected from the group consisting of N, CH and C—Cl;

T is selected from the group consisting of S, S═O, $CH_2$ and O;

E is selected from the group consisting of

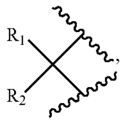

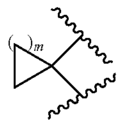

and

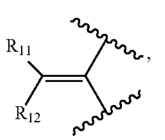

wherein $R_1$ and $R_2$ are each independently selected from the group consisting of hydrogen, halogen, phenyl, alkylthio, and alkyl optionally substituted with carbamoyl (preferably $C_1$-$C_6$ alkyl, the same applies below); $R_{11}$ and $R_{12}$ are each independently selected from the group consisting of hydrogen, carboxyl, and alkyl optionally substituted with carbamoyl; and m is an integer from 1 to 5;

F is a single bond;

$R_{13}$ is hydrogen or a carboxyl protecting group;

$R_{14}$ is optionally substituted aryl or optionally substituted heterocyclyl;

A is selected from the group consisting of alkylene, alkenylene and alkynylene;

Q is optionally substituted heterocyclyl (preferably heterocyclyl containing at least one N atom);

$Y_1$ is selected from the group consisting of optionally substituted alkylene, optionally substituted alkenylene, optionally substituted alkynylene, —N═CH—CH═N—, —N═CH—CH═N—O—, —N═CH—$CH_2$—, —N═CH(C═O)—, —N═CH(C═S)—, —$NR_{71}$—C(═O)—, —$NR_{71}$—C(═NH)—, —$NR_{71}$—C(═S)—, —$NR_{71}$—C(═O)$CH_2$—, —$NR_{71}$—C(═NH)$CH_2$—, —$NR_{71}$—C(═S)$CH_2$—, —$NR_{71}$C(═O)$NR_{71}$—, —$NR_{71}$C(═NH)$NR_{71}$—, —$NR_{71}$C(═S)$NR_{71}$—, —$NR_{71}$C(═O)$NR_{71}$—O—, —$NR_{71}$C(═NH)$NR_{71}$—O—, —$NR_{71}$C(═S)$NR_{71}$—O—, —$NR_{71}$C(═O)—C(═O)$NR_{71}$—, —$NR_{71}$C(═NH)—C(═O)$NR_{71}$—, —$NR_{71}$C(═S)—C(═O)$NR_{71}$—, —$NR_{71}$C(═NH)—C(═NH)$NR_{71}$—, —$NR_{71}$C(═S)—C(═S)$NR_{71}$—, —$NR_{71}CH_2$C(═O)—, —$NR_{71}CH_2$C(═S)—, —$NR_{71}$S(═O)$_2$$NR_{71}$C(═O)—, —$NR_{71}$S(═O)$_2$$NR_{71}$C(═NH)—, —$NR_{71}$S(═O)$_2$$NR_{71}$C(═S)—, —$NR_{71}$C(═O)$NR_{71}$S(═O)$_2$—, —$NR_{71}$C(═NH)$NR_{71}$S(═O)$_2$—, —$NR_{71}$C(═S)$NR_{71}$S(═O)$_2$— and a single bond;

each $R_{71}$ may be independently selected from the group consisting of hydrogen, hydroxy, alkyl and optionally substituted alkoxy;

$Y_2$ is selected from the group consisting of a single bond, optionally substituted alkylene, optionally substituted alkenylene and optionally substituted alkynylene;

$Y_3$ is selected from the group consisting of —C(═O)—, —C(═S)—, —C(═O)—C(═O)—, —C(═S)—C(═O)—, —C(═S)—C(═S)—, —C(═O)—C(═$NR_{15}$)—, —C(═S)—C(═$NR_{15}$)— and —N═$CR_{16}$—, wherein $R_{15}$ is selected from the group consisting of hydroxy, ureido and optionally substituted alkoxy; and $R_{16}$ is optionally substituted carbamoyl or carboxyl or a salt thereof optionally protected by a carboxyl protecting group;

$Z_1$ is selected from the group consisting of —$NR_{16}$—, —$N^+R_{17}R_{18}$—, —$NR_{19}$—C(═O)—$NR_{20}$—, —$NR_{19}$—C(═NH)—$NR_{20}$—, —$NR_{19}$—C(═S)—$NR_{20}$— and a single bond, wherein $R_{16}$ is selected from the group consisting of hydrogen, carbamoyl, optionally substituted alkyl and hydroxy optionally protected by a hydroxy protecting group; $R_{17}$ and $R_{18}$ are each independently selected from the group consisting of optionally substituted alkyl, optionally substituted alkylene and optionally substituted alkenylene; $R_{19}$ and $R_{20}$ are each independently selected from the group consisting of hydrogen, optionally substituted alkyl, hydroxy optionally protected by a hydroxy protecting group and optionally substituted heterocyclyl; and $Z_2$ is —$NR_{21}$— or a single bond, wherein $R_{21}$ is selected from the group consisting of hydrogen, optionally substituted alkyl and optionally protected hydroxy.

In certain embodiments, Q does not comprise a quaternary ammonium structure.

In certain embodiments, heterocyclyl in Q is selected from the group consisting of pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl and homopiperazinyl, wherein the heterocyclyl is optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio; preferred examples of Q include

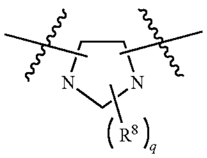
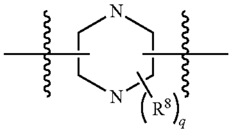
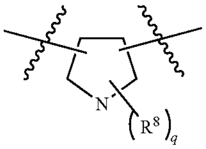
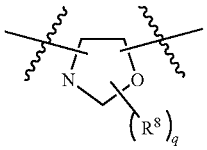
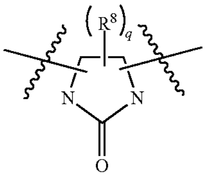
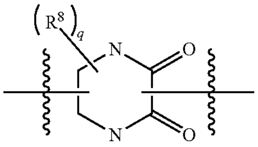
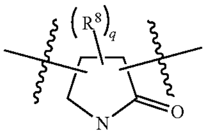
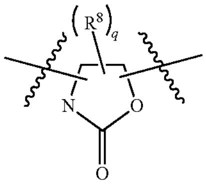
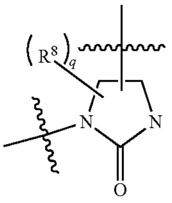
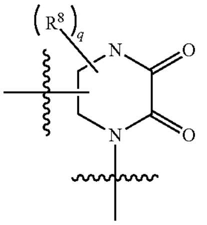
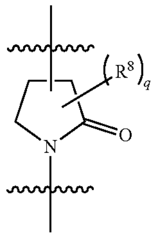
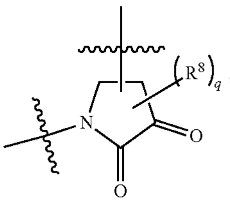, for example, may be

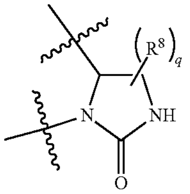
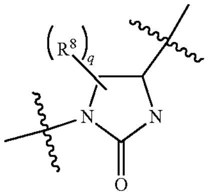
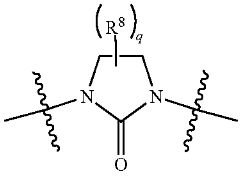
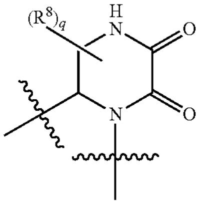
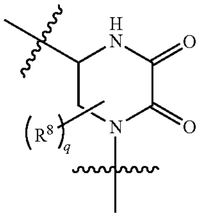
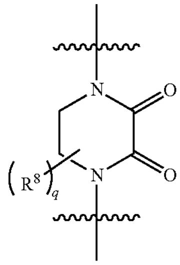
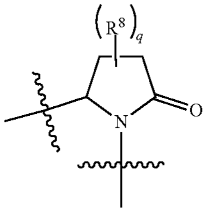
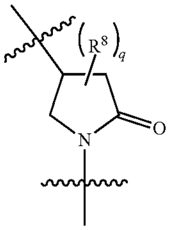
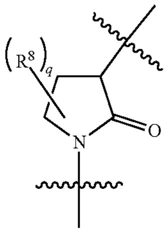
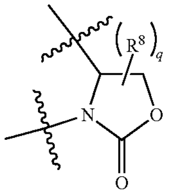
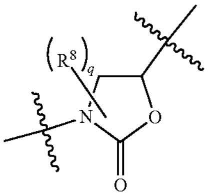, wherein each $R_8$ is independently selected from the group consisting of hydrogen, halogen, hydroxy, alkyl, alkoxy, haloalkyl, and haloalkoxy; and each q is independently an integer from 0 to 5.

In certain embodiments, $R_{14}$ is

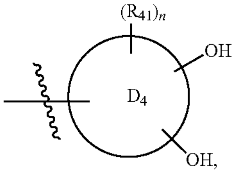

wherein $D_4$ is aryl or heterocyclyl, preferably phenyl or naphthyl, each $R_{41}$ is independently selected from the group consisting of alkyl, halogen, hydroxy, mercapto, oxo, thio, —$NR_iR_j$, —$C(O)R_k$, —$C(O)OR_k$, nitro, cyano, alkoxy and alkylthio, wherein the alkyl, alkoxy and alkylthio are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy, alkylthio, cycloalkyl, heterocyclyl, aryl and heteroaryl; and n is an integer from 0 to 8.

In certain embodiments, the compound of formula (I-5) is (II-5)

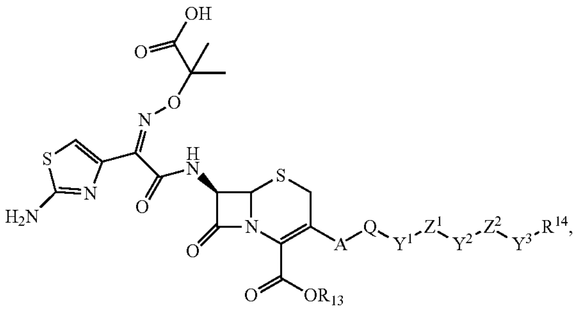

wherein A, Q, $Y_1$, $Z_1$, $Y_2$, $Z_2$, $Y_3$, $R_{13}$ and $R_{14}$ are as described above.

In certain embodiments, the compound is selected from the group consisting of:

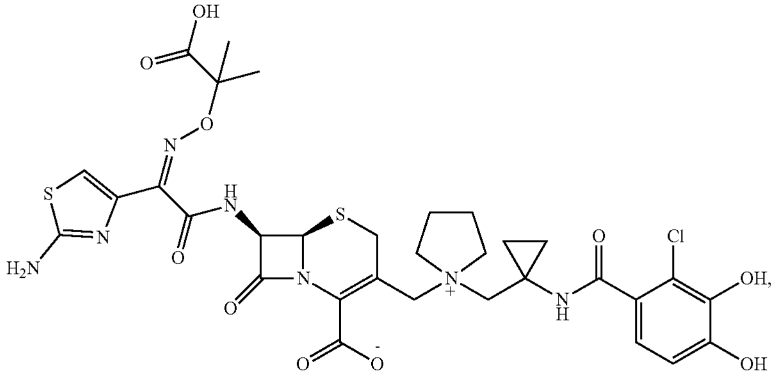

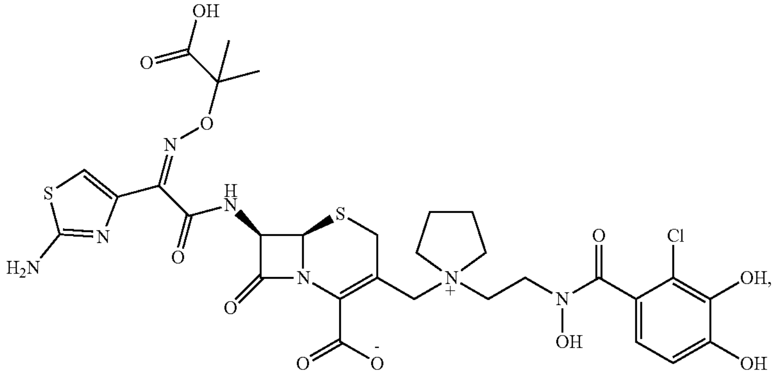

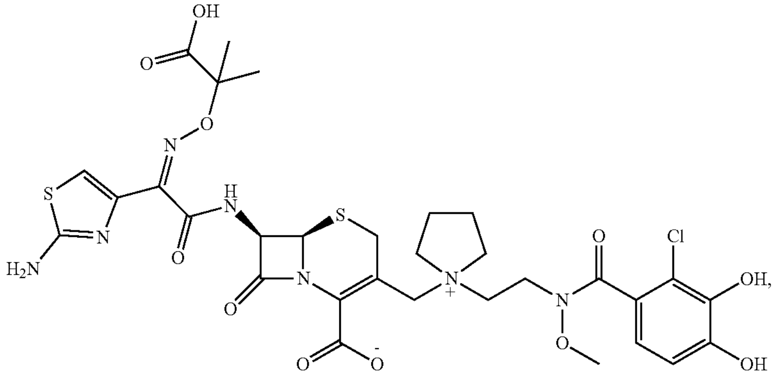

-continued
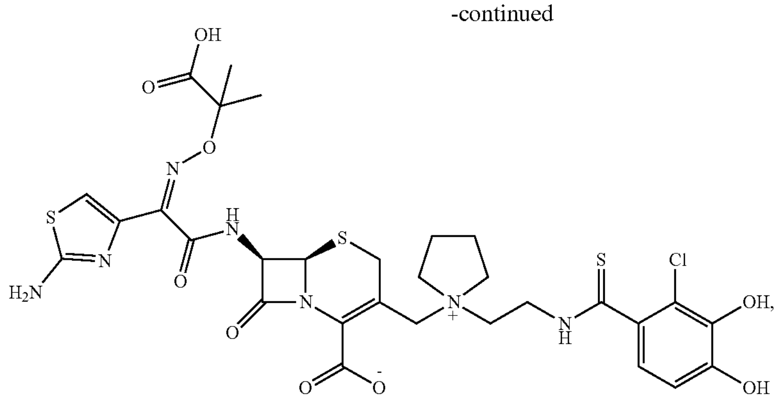
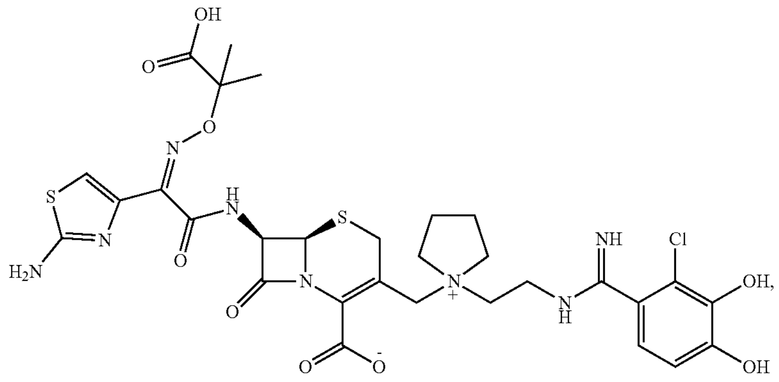
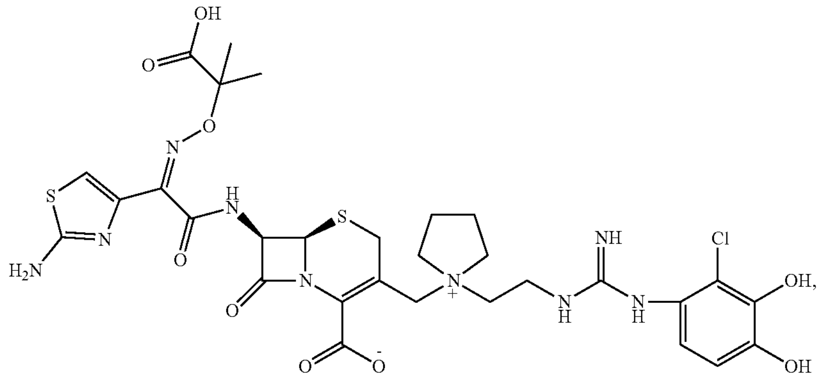
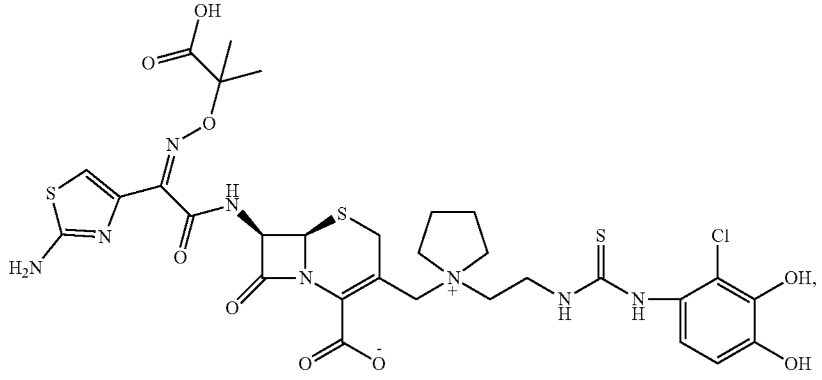

-continued
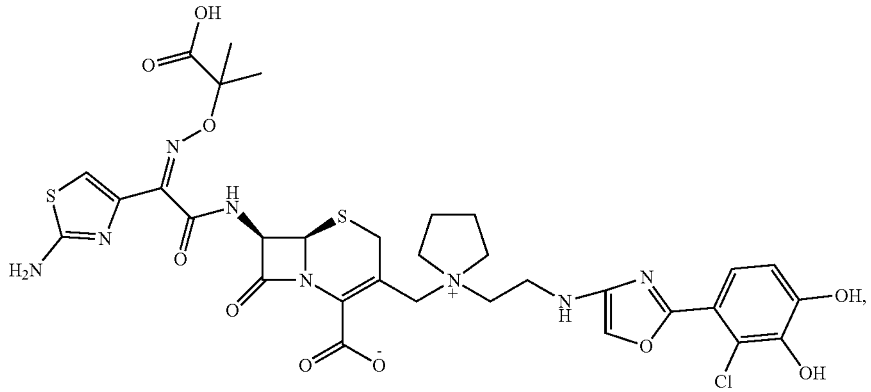
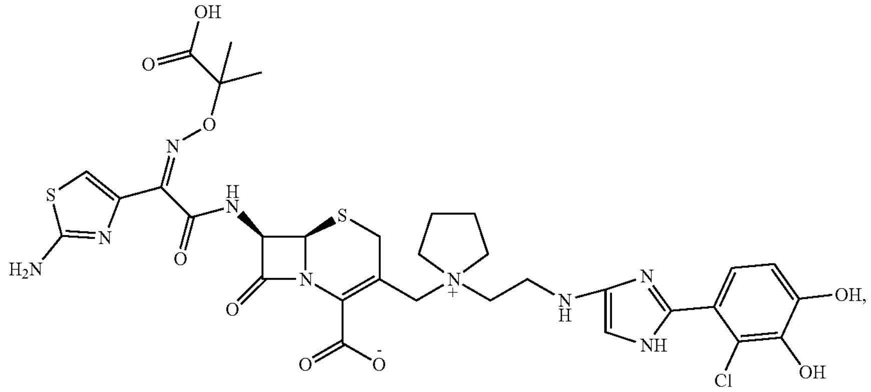
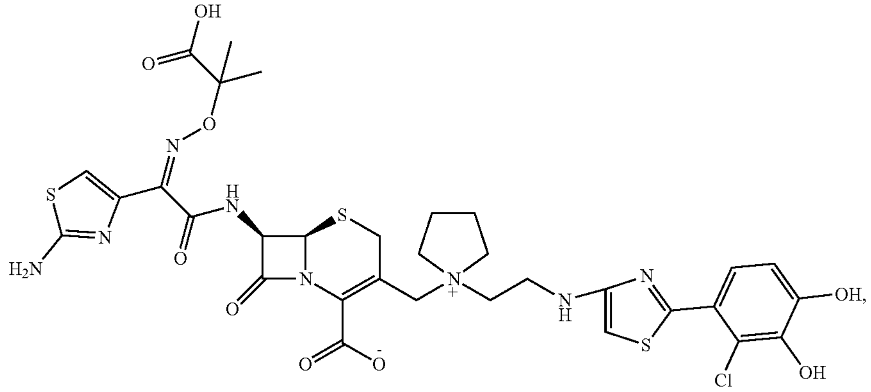
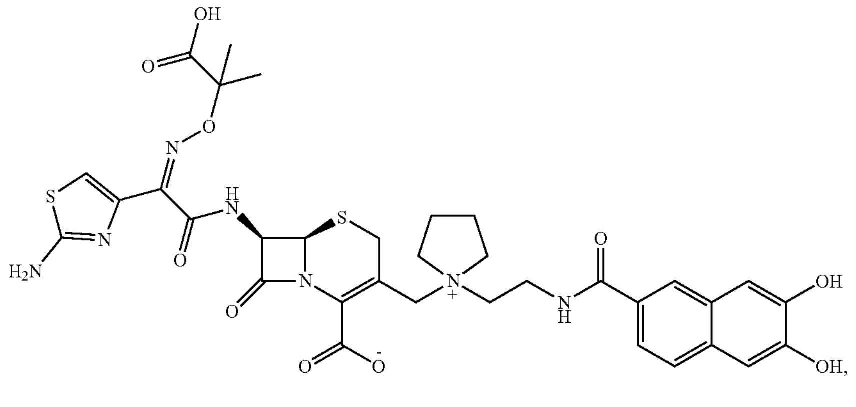

-continued
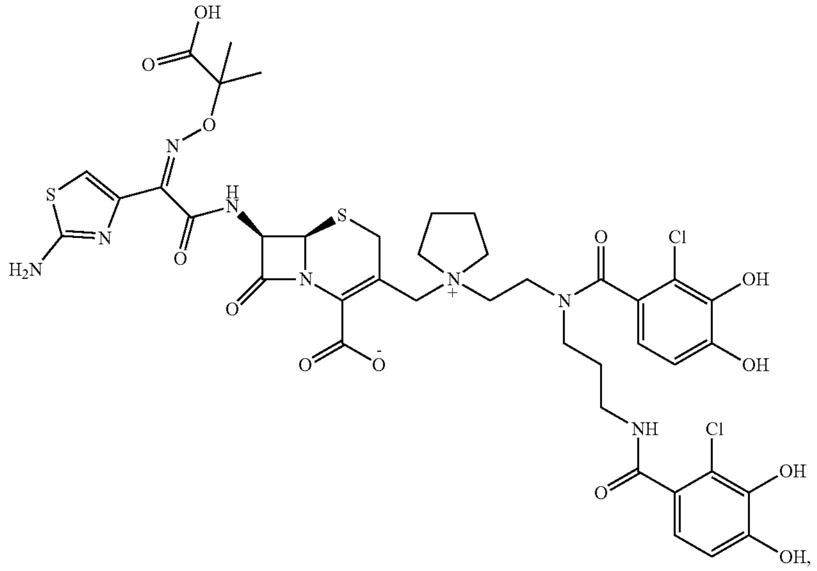
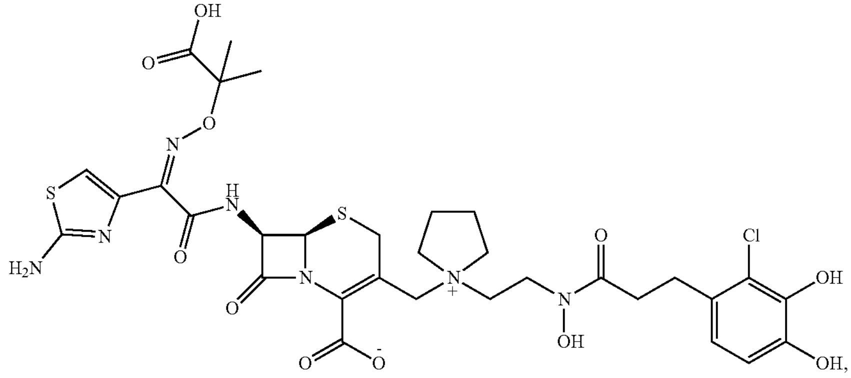
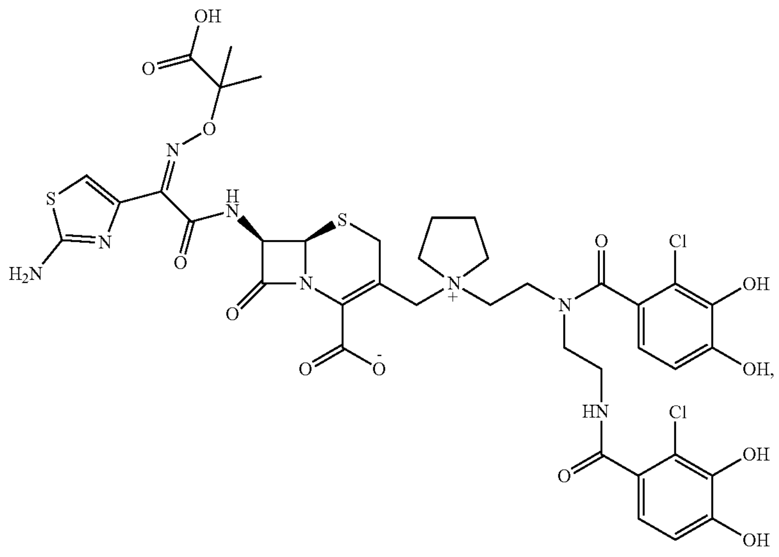

-continued

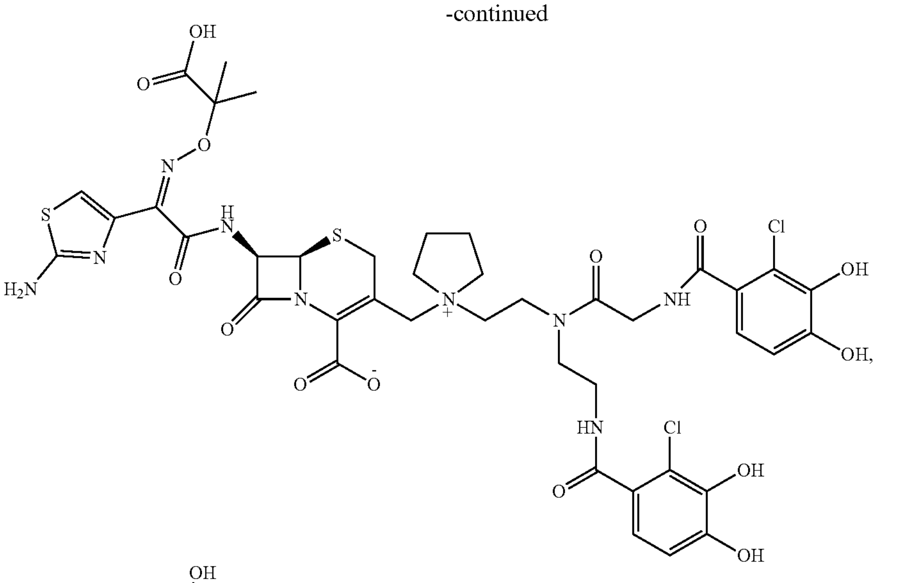

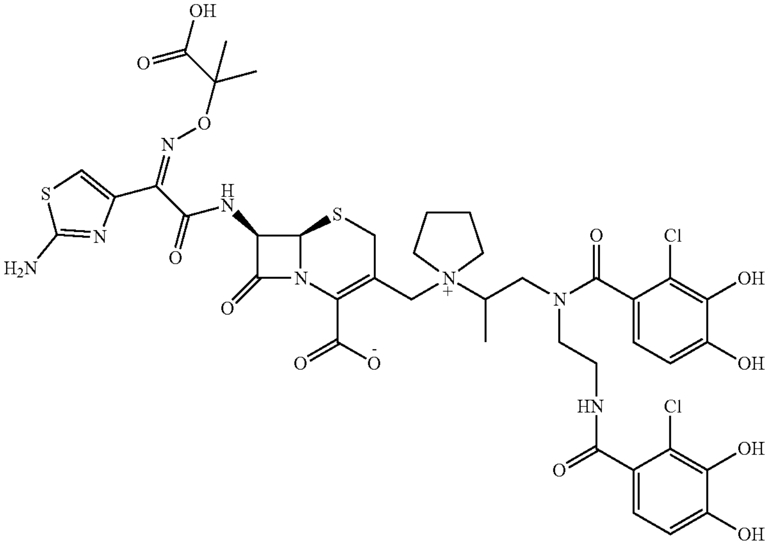

and

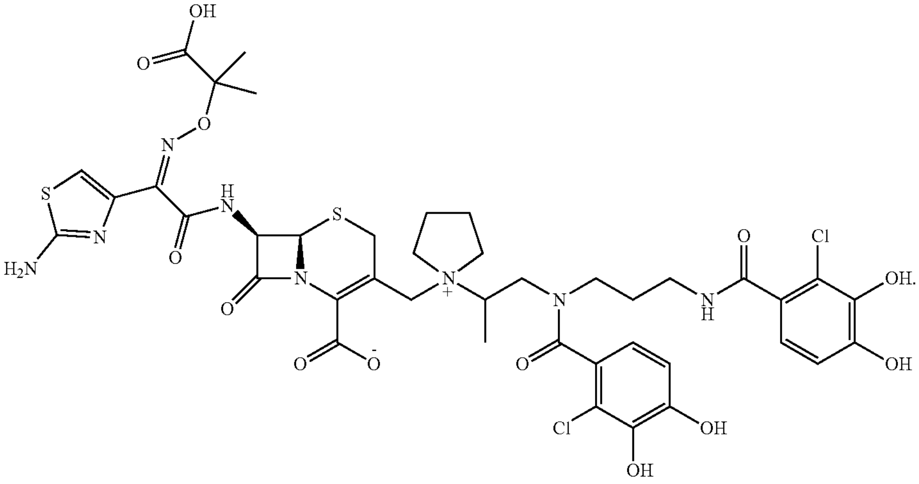 [SMILES: CC(CN(CCCNC(=O)c1ccc(O)c(O)c1Cl)C(=O)c1ccc(O)c(O)c1Cl)[N+]1(CC2=C(C(=O)O)N3C(=O)[C@@H](NC(=O)/C(=N\OC(C)(C)C(=O)O)c4csc(N)n4)[C@H]3SC2)CCCC1]

The "alkyl" described herein is preferably $C_1$-$C_6$ alkyl.

The "alkylene" described herein is preferably $C_1$-$C_6$ alkylene.

The "alkenylene" described herein is preferably $C_2$-$C_6$ alkenylene.

The "alkenylene" described herein is preferably $C_2$-$C_6$ alkynylene.

The "alkoxy" described herein is preferably $C_1$-$C_6$ alkoxy.

The "alkylthio" described herein is preferably $C_1$-$C_6$ alkylthio.

The "cycloalkyl" described herein is preferably 3- to 12-membered cycloalkyl, and more preferably 3- to 6-membered cycloalkyl.

The "fused cycloalkyl" described herein is preferably 6- to 14-membered fused cycloalkyl, and more preferably 7- to 10-membered fused cycloalkyl.

The "heterocyclyl" described herein is preferably 3- to 12-membered heterocyclyl, and more preferably 3- to 6-membered heterocyclyl.

The "fused heterocyclyl" described herein is preferably 6- to 14-membered fused heterocyclyl, and more preferably 7- to 10-membered fused heterocyclyl.

The "aryl" described herein is preferably 6- to 14-membered aryl, and more preferably 6- to 10-membered aryl.

The "fused cycloaryl" described herein is preferably 8- to 14-membered fused cycloaryl, and more preferably 8- to 12-membered fused cycloaryl.

The "heteroaryl" described herein is preferably 5- to 12-membered heteroaryl, and more preferably 5- to 8-membered heteroaryl.

The "fused heteroaryl" described herein is preferably 5- to 14-membered fused heteroaryl, and more preferably 5- to 12-membered fused heteroaryl.

The "optionally substituted" group described herein may be a group optionally substituted with one or more substituents selected from the group consisting of alkyl (preferably $C_1$-$C_6$ alkyl), halogen, deuterium, hydroxy, mercapto, —$NR_iR_j$, oxo, thio, —C(O)$R_k$, —C(O)O$R_k$, —S(O)$R_k$, —S(O)O$R_k$, —S(O)(O)$R_k$, —S(O)(O)O$R_k$, —C(S)$R_k$, nitro, cyano, alkoxy (preferably $C_1$-$C_6$ alkoxy), alkylthio (preferably $C_1$-$C_6$ alkylthio), alkenyl (preferably $C_2$-$C_6$ alkenyl), alkynyl (preferably $C_2$-$C_6$ alkynyl), cycloalkyl (preferably 3- to 6-membered cycloalkyl), heterocyclyl (preferably 3- to 6-membered heterocyclyl), fused cycloalkyl (preferably 7- to 10-membered cycloalkyl), fused heterocyclyl (preferably 7- to 10-membered fused heterocyclyl), aryl (preferably 6- to 10-membered aryl), heteroaryl (preferably 5- to 10-membered heteroaryl), fused cycloaryl (preferably 8- to 12-membered fused cycloaryl), and fused heteroaryl (preferably 5- to 12-membered fused heteroaryl). $R_i$, $R_j$ and $R_k$ are as described above. The set of optional substituents for each "optionally substituted" group may be identical or different.

In certain embodiments, the compound of the present disclosure is in the Z configuration.

The present disclosure also provides a pharmaceutical composition comprising at least one of the compounds or the pharmaceutically acceptable salt thereof, or the stereoisomer, rotamer, tautomer or deuterated compound thereof described above, and a pharmaceutically acceptable carrier, diluent or excipient.

In certain embodiments, the pharmaceutical composition is in unit dose of 0.001-1000 mg.

In certain embodiments, the pharmaceutical composition comprises 0.01%-99.99% of the above compounds based on the total weight of the composition. In certain embodiments, the pharmaceutical composition comprises 0.1%-99.9% of the above compounds. In certain embodiments, the pharmaceutical composition comprises 0.5%-99.5% of the above compounds. In certain embodiments, the pharmaceutical composition comprises 1%-99% of the above compounds. In certain embodiments, the pharmaceutical composition comprises 2%-98% of the above compounds.

In certain embodiments, the pharmaceutical composition comprises 0.01%-99.99% of a pharmaceutically acceptable carrier, diluent or excipient based on the total weight of the composition. In certain embodiments, the pharmaceutical composition comprises 0.1%-99.9% of a pharmaceutically acceptable carrier, diluent or excipient. In certain embodiments, the pharmaceutical composition comprises 0.5%-99.5% of a pharmaceutically acceptable carrier, diluent or excipient. In certain embodiments, the pharmaceutical composition comprises 1%-99% of a pharmaceutically acceptable carrier, diluent or excipient. In certain embodiments, the pharmaceutical composition comprises 2%-98% of a pharmaceutically acceptable carrier, diluent or excipient.

The present disclosure also relates to use of the compound or the pharmaceutically acceptable salt, stereoisomer, rotamer tautomer or deuterated compound thereof, or the pharmaceutical composition comprising the same described in the present disclosure in preparing a medicament for the prevention and treatment of a disease caused by pathogenic bacteria in a mammal, including human.

The present disclosure also relates to use of the compound or the pharmaceutically acceptable salt thereof, or the stereoisomer, rotamer or tautomer or deuterated compound thereof described in the present disclosure in preparing a medicament for the prevention and treatment of a disease caused by gram-negative bacteria.

The present disclosure also relates to the compound or the pharmaceutically acceptable salt, stereoisomer, rotamer, tautomer or deuterated compound thereof, or the pharmaceutical composition comprising the same described in the present disclosure for use as a medicament.

The present disclosure also relates to the compound or the pharmaceutically acceptable salt, stereoisomer, rotamer, tautomer or deuterated compound thereof, or the pharmaceutical composition comprising the same described in the present disclosure for use in preventing or treating a disease caused by pathogenic bacteria in a mammal, including human.

The present disclosure also relates to the compound or the pharmaceutically acceptable salt, stereoisomer, rotamer, tautomer or deuterated compound thereof, or the pharmaceutical composition comprising the same described in the present disclosure for use in preventing or treating a disease caused by gram-negative bacteria.

The present disclosure also relates to a method for preventing and treating a disease caused by pathogenic bacteria, which comprises administering to a patient in need thereof a therapeutically effective dose of the compound or the pharmaceutically acceptable salt, stereoisomer, rotamer, tautomer or deuterated compound thereof, or the pharmaceutical composition comprising the same described in the present disclosure.

The present disclosure also relates to a method for preventing and treating a disease caused by gram-negative bacteria, which comprises administering to a patient in need thereof a therapeutically effective dose of the compound or the pharmaceutically acceptable salt, stereoisomer, rotamer, tautomer or deuterated compound thereof, or the pharmaceutical composition comprising the same described in the present disclosure.

Herein, the disease caused by pathogenic bacteria or the disease caused by gram-negative bacteria includes, but is not limited to airway infectious diseases, urinary system infectious diseases, respiratory system infectious diseases, septicemia, nephritis, cholecystitis, oral infectious diseases, endocarditis, pneumonia, bone marrow membrane myelitis, otitis media, enteritis, empyema, traumatic infectious diseases, opportunistic infections, and the like.

Herein, the gram-negative bacteria are preferably gram-negative bacteria of intestinal bacteria (*E. coli, Klebsiella, Serratia, Enterobacter, Citrobacter, Morganella, Providencia, Proteus*, etc.), gram-negative bacteria residing in the respiratory system (*Haemophilus, Moraxella*, etc.), and glucose nonfermenting gram-negative bacteria (*Pseudomonas aeruginosa, Pseudomonas* other than *P. aeruginosa, Stenotrophomonas, Burkholderia, Acinetobacter*, etc).

The present disclosure also provides use of the compound or the pharmaceutically acceptable salt, stereoisomer, rotamer, tautomer or deuterated compound thereof described in the present disclosure in a medicament for the prevention and treatment of a disease caused by gram-positive bacteria.

Herein, the mammal may be a human or a non-human mammal.

The present disclosure further provides a kit comprising the compound or the pharmaceutically acceptable salt, stereoisomer, rotamer, tautomer or deuterated compound thereof, or the pharmaceutical composition described in the present disclosure.

According to the test method well known in the art (e.g., WO2010050468), the compounds of the present disclosure are determined to have inhibitory activity against gram-negative bacteria and have excellent efficacy.

TERMS AND DEFINITIONS

Unless otherwise stated, the terms used in the specification and claims have the following meanings.

The term "alkyl" refers to a saturated aliphatic hydrocarbon group which is a linear or branched group containing 1 to 20 carbon atoms, preferably an alkyl group containing 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various side-chain isomers thereof, etc. More preferably, the alkyl is an alkyl containing 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl may be substituted or unsubstituted, and when it is substituted, the substitution with a substituent may be performed at any available connection site, wherein the substituent is one or more of groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl and a carboxylate group.

The term "alkylene" refers to a saturated linear or branched aliphatic hydrocarbon group having 2 residues derived from the parent alkane by removal of two hydrogen atoms from the same carbon atom or two different carbon atoms. It is a linear or branched group containing 1 to 20 carbon atoms, preferably alkylene containing 1 to 12 carbon atoms, and more preferably alkylene containing 1 to 6 carbon atoms. Non-limiting examples of alkylene include, but are not limited to, methylene ($-CH_2-$), 1,1-ethylene ($-CH(CH_3)-$), 1,2-ethylene ($-CH_2CH_2-$), 1,1-propylene ($-CH(CH_2CH_3)-$), 1,2-propylene ($-CH_2CH(CH_3)-$), 1,3-propylene ($-CH_2CH_2CH_2-$), 1,4-butylene ($-CH_2CH_2CH_2CH_2-$), etc. The alkylene may be substituted or unsubstituted, and when it is substituted, the substitution with a substituent may be performed at any available connection site.

The term "alkenylene" refers to a linear alkenyl group containing 2 to 8 carbon atoms, preferably 2 to 6 carbon atoms, and more preferably 2 to 4 carbon atoms, and having at least one double bond at any positions, including, for example, ethenylene, allylene, propenylene, butenylene, prenylene, butadienylene, pentenylene, pentadienylene, hexenylene, hexadienylene, etc.

The term "alkynylene" refers to a linear alkynylene group containing 2 to 8 carbon atoms, preferably 2 to 6 carbon atoms, and more preferably 2 to 4 carbon atoms, and having at least one triple bond at any positions, including, for example, ethynylene, propynylene, butynelene, pentynylene, hexynylene, etc.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Non-limiting examples of polycyclic cycloalkyl include spiro cycloalkyl, fused cycloalkyl, and bridged cycloalkyl.

The term "spiro cycloalkyl" refers to a 5- to 20-membered polycyclic group in which monocyclic rings share one carbon atom (referred to as the spiro atom), wherein these rings may contain one or more double bonds, but none of them have a fully conjugated π-electron system. The spiro cycloalkyl is preferably 6- to 14-membered, and more preferably 7- to 10-membered. According to the number of the spiro atoms shared among the rings, the spiro cycloalkyl may be monospiro cycloalkyl, bispiro cycloalkyl or polyspiro cycloalkyl, preferably monospiro cycloalkyl and bispiro cycloalkyl, and more preferably 4-membered/4-membered, 4-membered/5-membered, 4-membered/6-membered, 5-membered/5-membered or 5-membered/6-membered monospiro cycloalkyl. Non-limiting examples of spiro cycloalkyl include:

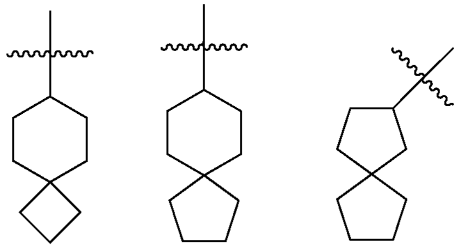

-continued

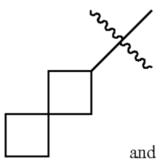

and

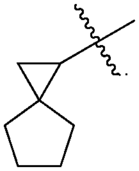

The term "fused cycloalkyl" refers to a 5- to 20-membered all-carbon polycyclic group in which each ring in the system shares a pair of adjacent carbon atoms with other rings in the system, wherein one or more of the rings may contain one or more double bonds, but none of them has a fully conjugated π-electron system. The fused cycloalkyl is preferably 6- to 14-membered, and more preferably 7- to 10-membered. According to the number of the formed rings, the fused cycloalkyl may be bicyclic, tricyclic, tetracyclic or polycyclic fused cycloalkyl, preferably bicyclic or tricyclic fused cycloalkyl, and more preferably 5-membered/5-membered or 5-membered/6-membered bicyclic fused heterocyclyl. Non-limiting examples of fused cycloalkyl include:

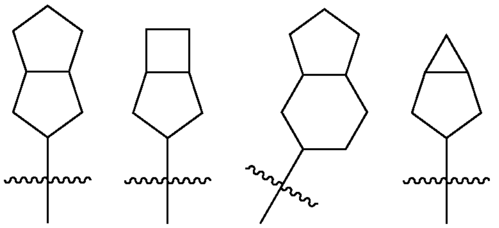

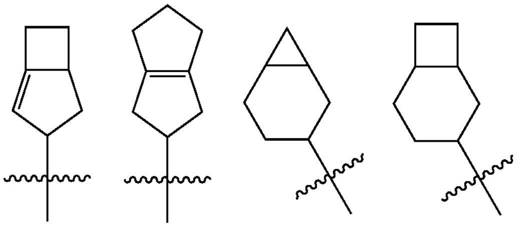

and

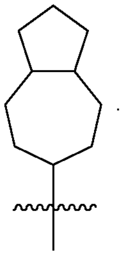

The term "bridged cycloalkyl" refers to a 5- to 20-membered all-carbon polycyclic group in which any two rings share two carbon atoms that are not directly connected to each other, wherein these rings may contain one or more double bonds, but none of them have a fully conjugated π-electron system. The bridged cycloalkyl is preferably 6- to 14-membered, and more preferably 7- to 10-membered. According to the number of the formed rings, the bridged cycloalkyl may be bicyclic, tricyclic, tetracyclic or polycyclic bridged cycloalkyl, preferably bicyclic, tricyclic or tetracyclic bridged cycloalkyl, and more preferably bicyclic or tricyclic bridged cycloalkyl. Non-limiting examples of bridged cycloalkyl include:

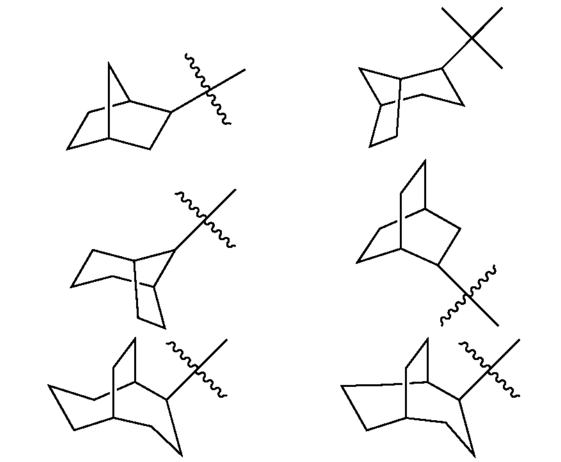

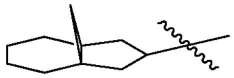

and

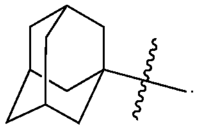

The cycloalkyl ring may be fused to an aryl, heteroaryl or heterocycloalkyl ring, wherein the ring attached to the parent structure is cycloalkyl. Non-limiting examples of cycloalkyl ring include, but are not limited to, indanyl, tetrahydronaphthyl, benzocycloheptyl, etc. The cycloalkyl may be optionally substituted or unsubstituted, and when it is substituted, the substituent is preferably one or more of groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl and a carboxylate group.

The term "heterocyclyl" refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen and $S(O)_m$ (where m is an integer from 0 to 2), excluding a ring moiety of —O—O—, —O—S— or —S—S—, and the remaining ring atoms are carbon atoms. The heterocyclyl preferably contains 3 to 12 ring atoms, of which 1 to 4 are heteroatoms; and more preferably contains 3 to 6 ring atoms. Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, and the like, preferably piperidinyl and pyrrolidinyl. Non-limiting examples of polycyclic heterocyclyl include spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more of the ring atoms are heteroatoms selected from the group consisting of nitrogen, oxygen and $S(O)_m$ (where m is an integer from 0 to 2), and the remaining ring atoms are carbon atoms. These rings may contain one or more double bonds, but none of them has a fully conjugated π-electron system. The spiro heterocyclyl is preferably 6- to 14-membered, and more preferably 7- to 10-membered. According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 4-membered/4-membered, 4-membered/5-membered, 4-membered/6-membered, 5-membered/5-membered or 5-membered/6-membered monospiro heterocyclyl. Non-limiting examples of spiro heterocyclyl include:

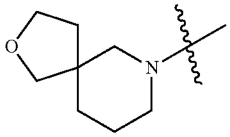
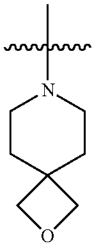
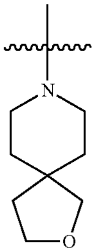
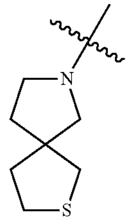
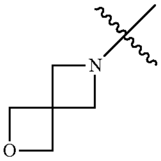
and
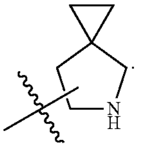
.

The term "fused heterocyclyl" refers to a 5- to 20-membered polycyclic heterocyclyl in which each ring shares a pair of adjacent atoms with the other rings in the system, wherein one or more of the rings may contain one or more double bonds, but none of them has a fully conjugated π-electron system, and one or more of the ring atoms are heteroatoms selected from the group consisting of nitrogen, oxygen or $S(O)_m$ (where m is an integer from 0 to 2), and the remaining ring atoms are carbon atoms. The fused heterocyclyl is preferably 6- to 14-membered, and more preferably 7- to 10-membered. According to the number of the formed rings, the fused heterocyclyl may be bicyclic, tricyclic, tetracyclic or polycyclic fused heterocyclyl, preferably bicyclic or tricyclic fused heterocyclyl, and more preferably 5-membered/5-membered or 5-membered/6-membered bicyclic fused heterocyclyl. Non-limiting examples of fused heterocyclyl include:

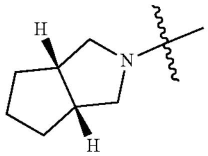
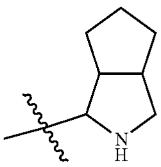
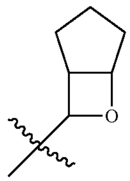
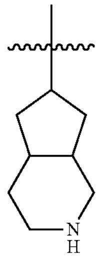
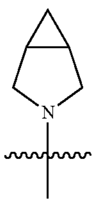
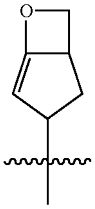
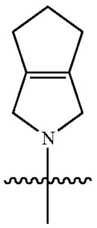

-continued

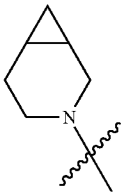
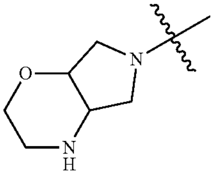
,
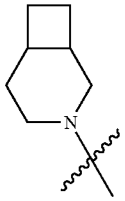
,
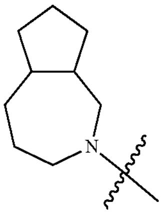
,
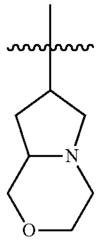
,
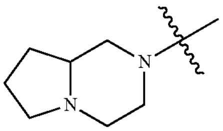
and
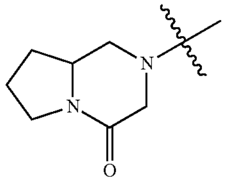
.

The term "bridged heterocyclyl" refers to a 5- to 14-membered polycyclic heterocyclyl in which any two rings share two carbon atoms that are not directly connected to each other, wherein these rings may contain one or more double bonds, but none of them has a fully conjugated π-electron system, and one or more of the ring atoms are heteroatoms selected from the group consisting of nitrogen, oxygen and $S(O)_m$ (where m is an integer from 0 to 2), and the remaining ring atoms are carbon atoms. The bridged heterocyclyl is preferably 6- to 14-membered, and more preferably 7- to 10-membered. According to the number of the formed rings, the bridged heterocyclyl may be bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. Non-limiting examples of bridged heterocyclyl include:

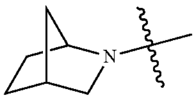
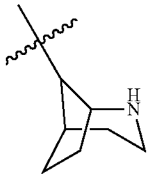
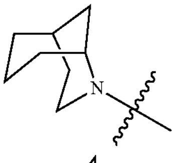
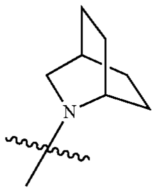
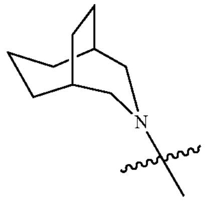
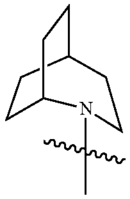
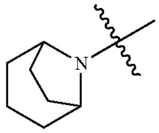
and
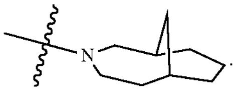
.

The heterocyclyl ring may be fused to an aryl, heteroaryl or cycloalkyl ring, wherein the ring connected to the parent structure is heterocyclyl. Non-limiting examples of heterocyclyl ring include, but are not limited to:

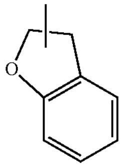 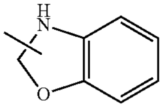 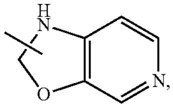,

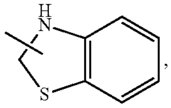, etc.

The heterocyclyl may be optionally substituted or unsubstituted, and when it is substituted, the substituent is preferably one or more of groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl and a carboxylate group.

The term "aryl" refers to a 6- to 14-membered, preferably 6- to 10-membered all-carbon monocyclic or fused polycyclic (i.e., rings that share a pair of adjacent carbon atoms) group having a conjugated π-electron system, such as phenyl and naphthyl. The aryl ring may be fused to a heteroaryl, heterocyclyl or cycloalkyl ring, wherein the ring connected to the parent structure is the aryl ring. Non-limiting examples of aryl ring include, but are not limited to:

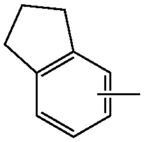, 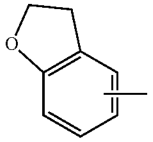, 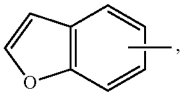,

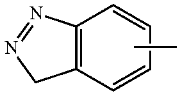, 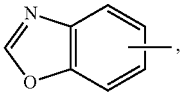,

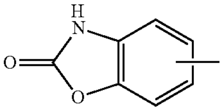, 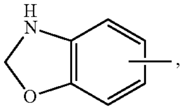,

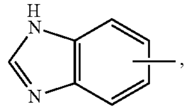, 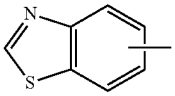,

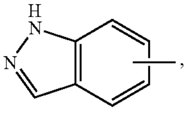, 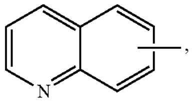,

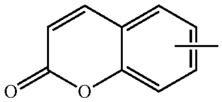 and 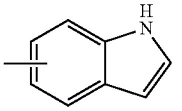;

the aryl ring may be optionally substituted or unsubstituted, and when it is substituted, the substituent is preferably one or more of groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and a carboxylate group, preferably phenyl.

The term "fused cycloaryl" may be an unsaturated aromatic fused ring structure containing 8 to 14 ring atoms, preferably 8 to 12 ring atoms, formed by connecting two or more ring structures that share two adjacent atoms with each other, for example, including all unsaturated fused cycloaryl groups such as naphthalene, phenanthrene, etc., and partially saturated fused cycloaryl groups such as benzo 3- to 8-membered saturated monocyclic cycloalkyl, benzo 3- to 8-membered partially saturated monocyclic cycloalkyl, specifically, 2,3-dihydro-1H-indenyl, 1H-indenyl, 1,2,3,4-tetrahydronaphthyl, 1,4-dihydronaphthyl, etc.

The term "heteroaryl" refers to a heteroaromatic system containing 1 to 4 heteroatoms and 5 to 14 ring atoms, wherein the heteroatoms are selected from the group consisting of oxygen, sulfur and nitrogen. The heteroaryl is preferably 5- to 12-membered, e.g., imidazolyl, furyl, thienyl, thiazolyl, pyrazolyl, oxazolyl, pyrrolyl, tetrazolyl, pyridyl, pyrimidinyl, thiadiazole, pyrazinyl and the like, preferably imidazolyl, pyrazolyl, pyrimidinyl or thiazolyl; and more preferably pyrazolyl or thiazolyl. The heteroaryl ring may be fused to an aryl, heterocyclyl or cycloalkyl ring, wherein the ring connected to the parent structure is heteroaryl. Non-limiting examples of heteroaryl ring include:

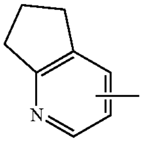, 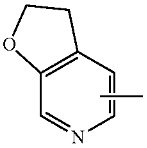, 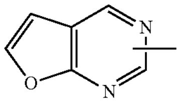,

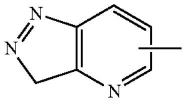, 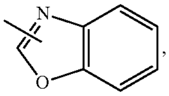, 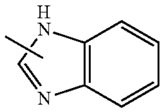,

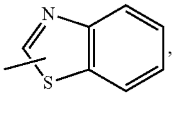, 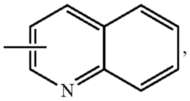,

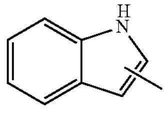 and 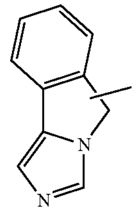.

The heteroaryl may be optionally substituted or unsubstituted, and when it is substituted, the substituent is preferably one or more of groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and a carboxylate group.

The term "fused heteroaryl" may be an unsaturated aromatic fused ring structure containing 5 to 14 ring atoms (at least one heteroatom) formed by connecting two or more ring structures that share two adjacent atoms with each other, including the case where a carbon atom, a nitrogen atom and a sulfur atom may be oxidized, preferably "5- to 12-membered fused heteroaryl", "7- to 12-membered fused heteroaryl", "9- to 12-membered fused heteroaryl group" and the like, for example, benzofuranyl, benzoisothiafuranyl, benzothienyl, indolyl, isoindolyl, benzoxazolyl, benzimidazolyl, indazolyl, benzotriazolyl, quinolyl, 2-quinolinone, 4-quinolinone, 1-isoquinolinone, isoquinolinyl, acridinyl, phenanthridinyl, benzopyridazinyl, phthalazinyl, quinazolinyl, quinoxalinyl, phenazinyl, pteridinyl, purinyl, naphthyridinyl, phenazine, phenothiazine and the like.

The fused heteroaryl may be optionally substituted or unsubstituted, and when it is substituted, the substituent is preferably one or more of groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and a carboxylate group.

The term "alkoxy" refers to —O-(alkyl) and —O-(unsubstituted cycloalkyl), wherein the alkyl is as defined above. Non-limiting examples of alkoxy include methoxy, ethoxy, propoxy, butoxy, cyclopropyloxy, cyclobutoxy, cyclopentyloxy, and cyclohexyloxy. The alkoxy may be optionally substituted or unsubstituted, and when it is substituted, the substituent is preferably one or more of groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and a carboxylate group.

The term "alkylthio" refers to —S-(alkyl) and —S-(unsubstituted cycloalkyl), wherein the alkyl is as defined above. Non-limiting examples of the alkylthio include: methylthio, ethylthio, propylthio, butylthio, cyclopropylthio, cyclobutylthio, cyclopentylthio and cyclohexylthio. The alkylthio may be optionally substituted or unsubstituted, and when it is substituted, the substituent is preferably one or more of groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "hydroxyalkyl" refers to an alkyl group substituted with hydroxy, wherein the alkyl group is as defined above.

The term "haloalkyl" refers to an alkyl group substituted with halogen, wherein the alkyl group is as defined above.

The term "deuterated alkyl" refers to an alkyl group substituted with a deuterium atom, wherein the alkyl group is as defined above.

The term "hydroxy" refers to —OH.

The term "oxo" refers to =O. For example, a carbon atom is connected to an oxygen atom via a double bond to form a ketone or aldehyde group.

The term "thio" refers to =S. For example, the carbon atom is connected to a sulfur atom via a double bond to form thiocarbonyl-C(S)—.

The term "halogen" refers to fluorine, chlorine, bromine or iodine.

The term "amino" refers to —$NH_2$.

The term "cyano" refers to —CN.

The term "nitro" refers to —$NO_2$.

The term "carboxyl" refers to —C(O)OH.

The term "aldehyde" refers to —CHO.

The term "carboxylate" refers to —C(O)O(alkyl) or —C(O)O(cycloalkyl), wherein the alkyl and cycloalkyl are as defined above.

The term "acyl halide" refers to a compound containing a —C(O)-halogen group.

The "carboxyl protecting group" is a suitable group known in the art for carboxyl protection, referring to the literature ("Protective Groups in Organic Synthesis", $5^{Th}$ Ed. T. W. Greene & P. G. M. Wuts) for the carboxyl protecting groups. As an example, preferably, the carboxyl protecting group may be a substituted or unsubstituted $C_{1-10}$ linear or branched alkyl, substituted or unsubstituted $C_{2-10}$ linear or branched alkenyl or alkynyl, substituted or unsubstituted $C_{3-8}$ cyclic alkyl, substituted or unsubstituted $C_{5-10}$ aryl or heteroaryl, or ($C_{1-8}$ alkyl or aryl)$_3$ silyl; preferably $C_{1-6}$ linear or branched alkyl, and more preferably $C_{1-4}$ linear or branched alkyl. For example, the carboxyl protecting group may be methyl, ethyl, allyl, isopentenyl, trimethylsilylethyl, or the like.

The "amino protecting group" is a suitable group known in the art for amino protection, referring to the literature ("Protective Groups in Organic Synthesis", $5^{Th}$. Ed. T. W. Greene & P. G. M. Wuts) for the amino protecting groups. Preferably, the amino protecting group may be ($C_{1-10}$ alkyl or aryl)acyl, e.g., formyl, acetyl, benzoyl or the like; ($C_{1-6}$ alkyl or $C_{6-10}$ aryl)sulfonyl; ($C_{1-6}$ alkoxy or $C_{6-10}$ aryloxy) carbonyl, e.g., Boc or Cbz; or substituted or unsubstituted alkyl, e.g., trityl (Tr), 2,4-dimethoxybenzyl (DMB), p-methoxybenzyl (PMB) or benzyl (Bn).

The "hydroxy protecting group" is a suitable group known in the art for hydroxy protection, referring to the literature ("Protective Groups in Organic Synthesis", $5^{Th}$ Ed. T. W. Greene & P. G. M. Wuts) for the hydroxy protecting groups. As an example, preferably, the hydroxy protecting group may be ($C_{1-10}$alkyl or aryl)$_3$silyl, e.g., triethylsilyl, triisopropylsilyl, tert-butyldimethylsilyl, tert-butyldiphenylsilyl, or the like; $C_{1-10}$ alkyl or substituted alkyl, preferably alkoxy or aryl-substituted alkyl, and more preferably $C_{1-6}$ alkoxy-substituted $C_{1-6}$ alkyl or phenyl-substituted $C_{1-6}$ alkyl, and most preferably $C_{1-4}$ alkoxy-substituted $C_{1-4}$ alkyl, e.g., methyl, tert-butyl, allyl, benzyl, methoxymethyl (MOM), ethoxyethyl, 2-tetrahydropyranyl (THP), or the like; ($C_{1-10}$ alkyl or aryl)acyl, e.g., formyl, acetyl, benzoyl, or the like; ($C_{1-6}$ alkyl or $C_{6-10}$ aryl)sulfonyl; or ($C_{1-6}$ alkoxy or $C_{6-10}$ aryloxy)carbonyl.

The term "leaving group" refers to an atom or a functional group that is detached from a larger molecule in a chemical reaction. Representative leaving groups include halogen, substituted sulfonyloxy, phosphoryloxy, amino, $R_iR_jN$—, cyano, $R_mS$—, etc.

The substituted sulfonyloxy may be $C_1$-$C_6$ alkylsulfonyloxy, perfluoro $C_1$-$C_6$ alkylsulfonyloxy, arylsulfonyloxy, aralkylsulfonyloxy or the like.

Specific examples of the $C_1$-$C_6$ alkylsulfonyloxy include $C_1$-$C_6$ linear or branched alkylsulfonyloxy, e.g., methylsulfonyloxy, ethylsulfonyloxy, n-propylsulfonyloxy, isopropylsulfonyloxy, n-butylsulfonyloxy, tert-butylsulfonyloxy, n-pentylsulfonyloxy and n-hexylsulfonyloxy.

Specific examples of perfluoro $C_1$-$C_6$ alkylsulfonyloxy include $C_1$-$C_6$ linear or branched perfluoroalkylsulfonyloxy, e.g., trifluoromethylsulfonyloxy, 1,1,2,2,2-pentafluoro-1-ethylsulfonyloxy, 1,1,2,2,3,3,3-heptafluoro-1-propylsulfonyloxy, and 1,1,2,2,3,3,4,4,4-nonafluoro-1-butylsulfonyloxy.

Examples of arylsulfonyloxy include: phenylsulfonyloxy and naphthylsulfonyloxy optionally having 1 to 3 substituents on the phenyl ring selected from the group consisting of $C_1$-$C_6$ linear or branched alkyl, $C_1$-$C_6$ linear or branched alkyl, nitro and halogen atoms. Specific examples of the phenylsulfonyloxy having a substituent include phenylsulfonyloxy, 4-methylphenylsulfonyloxy, 2-methylphenylsulfonyloxy, 4-nitrophenylsulfonyloxy, 4-tolylsulfonyloxy, 2-nitrophenylsulfonyloxy, 3-chlorophenylsulfonyloxy, etc. Specific examples of the naphthylsulfonyloxy group include α-naphthylsulfonyloxy, 0-naphthylsulfonyloxy, etc.

Examples of the aralkylsulfonyloxy include: $C_1$-$C_6$ linear or branched alkylsulfonyloxy substituted with phenyl (which optionally has 1 to 3 substituents on the phenyl ring selected from the group consisting of $C_1$-$C_6$ linear or branched alkyl, $C_1$-$C_6$ linear or branched alkyl, nitro and halogen atoms); and $C_1$-$C_6$ linear or branched alkyl sulfonyl oxy substituted with naphthyl. Specific examples of the alkylsulfonyloxy substituted with phenyl include benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methylbenzylsulfonyloxy, 3-chlorobenzylsulfonyloxy, etc. Specific examples of the alkylsulfonyloxy substituted with naphthyl include α-naphthylmethylsulfonyloxy, β-naphthylmethylsulfonyloxy, etc.

The term “optional” or “optionally” means that the event or circumstance subsequently described may, but not necessarily, occur, and that the description includes instances where the event or circumstance occurs or does not occur. For example, “heterocyclyl optionally substituted with alkyl” means that alkyl may be, but not necessarily, present, and that the description includes instances where the heterocyclyl is or is not substituted with the alkyl.

The term “substituted” means that one or more, preferably up to 5, and more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue efforts.

In the chemical structure of the compound described herein, a “” bond is not specified with a configuration, that is, a “” bond may be “” or “”, or includes both “” and “” configurations. In the chemical structure of the compound described herein, a “” bond is not specified with a configuration, that is it may be in a Z configuration or an E configuration, or includes both configurations.

Tautomers are structural isomers of organic compounds that readily interconvert by a chemical reaction called tautomerization. This reaction often results in the formal migration of hydrogen atoms or protons accompanied by the conversion of a single bond to an adjacent double bond. Some common tautomeric pairs include: keto-enol and lactam-lactim. An example of a lactam-lactim equilibrium is present between A and B as shown below.

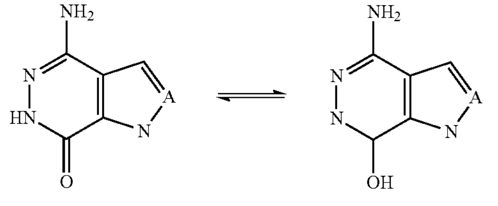

A B

All compounds in the present disclosure can be drawn as form A or form B. All tautomeric forms are within the scope of the present disclosure. The nomenclature of the compounds does not exclude any tautomers.

“Each independently” or “independently” means that substituents having the same selection range can be identical or different groups at their respective occurrences, and the selection of a substituent at each occurrence is not affected by the selection of that substituent (or substituents in the same range) at other occurrences.

Any isotopically-labeled derivative of the compound described herein, or a pharmaceutically acceptable salt thereof, or an isomer thereof, is encompassed by the present disclosure. Atoms that can be isotopically labeled include, but are not limited to, hydrogen, carbon, nitrogen, oxygen, phosphorus, fluorine, chlorine, iodine, etc. They may be separately replaced by the isotopes $^{2}H$ (D), $^{3}H$, $^{11}C$, $^{13}C$, $^{14}C$, $^{15}N$, $^{18}F$, $^{31}P$, $^{32}P$, $^{35}S$, $^{36}Cl$ and $^{125}I$, etc. Unless otherwise stated, when a position is specifically designated as deuterium (D), that position shall be understood to be deuterium having an abundance that is at least 3000 times greater than the natural abundance of deuterium (which is 0.015%) (i.e., incorporating at least 45% deuterium).

DETAILED DESCRIPTION

The preparation of the compound described herein and a pharmaceutically acceptable salt thereof is further described below in conjunction with the examples, which are not intended to limit the scope of the present disclosure.

Experimental procedures without conditions specified in the examples of the present disclosure, are generally conducted according to conventional conditions, or according to conditions recommended by the manufacturer of the starting materials or commercial products. Reagents without specific origins indicated are commercially available conventional reagents.

The structures of the compounds are determined by nuclear magnetic resonance (NMR) spectroscopy and/or mass spectrometry (LCMS). NMR shift (δ) is given in a unit of $10^{-6}$ (ppm). NMR spectra are measured using a Bruker AVANCE-400 nuclear magnetic resonance instrument, with deuterated dimethyl sulfoxide (DMSO-$d_6$), deuterated chloroform ($CDCl_3$) and deuterated methanol ($CD_3OD$) as determination solvents, and tetramethylsilane (TMS) as an internal standard. The spatial configurations of the optical isomers (isomers) of the compounds can be further confirmed by determining single crystal parameters.

HPLC analysis is performed using a Waters ACQUITY ultra high performance LC, Shimadzu LC-20A systems, Shimadzu LC-2010HT series, or Agilent 1200 LC high performance liquid chromatograph (ACQUITY UPLC BEH C18 1.7 μm 2.1×50 mm column, Ultimate XB-C18 3.0×150 mm column, or Xtimate C18 2.1×30 mm column).

MS analysis is performed by Waters SQD2 mass spectrometer in positive/negative ion mode with a mass scan range of 100 to 1200.

Chiral HPLC analytical determination is performed using a Chiralpak IC-3 100×4.6 mm I.D., 3 μm, Chiralpak AD-3 150×4.6 mm I.D., 3 μm, Chiralpak AD-3 50×4.6 mm I.D., 3 μm, Chiralpak AS-3 150×4.6 mm I.D., 3 μm, Chiralpak AS-3 100×4.6 mm I.D., 3 μm, ChiralCel OD-3 150×4.6 mm I.D., 3 μm, ChiralCel OD-3 100×4.6 mm I.D., 3 μm, ChiralCel OJ-H 150×4.6 mm I.D., 5 μm, or ChiralCel OJ-3 150×4.6 mm I.D., 3 μm chromatographic column.

Yantai Huanghai HSGF254 or Qingdao GF254 silica gel plate is adopted as a thin layer chromatography (TLC) silica gel plate. The specification of the silica gel plate is 0.15-0.2 mm for the thin layer chromatography (TLC), and 0.4-0.5 mm for the separation and purification of products by the TLC.

The flash column purification is performed using a Combiflash Rf150 (TELEDYNE ISCO) or Isolara one (Biotage) system.

The forward column chromatography is generally performed using 100-200 mesh, 200-300 mesh or 300-400 mesh Yantai Huanghai silica gel as a carrier, or using a Changzhou Santai pre-fill ultrapure forward phase silica gel column (40-63 μm, 60 g, 12 g, 25 g, 40 g, 80 g or other specifications).

Reverse phase column chromatography is generally performed using a Changzhou Santai pre-fill ultrapure C18 silica gel column (20-45 μm, 100 Å, 40 g, 80 g, 120 g, 220 g or other specifications).

The high pressure column purification is performed using a Waters AutoP system in combination with Waters XBridge BEH C18 OBD Prep Column, 130 Å, 5 μm, 19×150 mm or Atlantis T3 OBD Prep Column, 100 Å, 5 μm, 19×150 mm.

The chiral preparation is performed using a DAICEL CHIRALPAK IC (250×30 mm, 10 μm) or Phenomenex-Amylose-1 (250×30 mm, 5 μm) column.

Starting materials known in the present disclosure may be synthesized using or according to methods known in the art, or may be purchased from Shanghai Titan Scientific, ABCR GmbH & Co. KG, Acros Organics, Aldrich Chemical Company, Accela ChemBio Inc., Darui Chemicals, and other companies.

In the example, all reactions can be performed under nitrogen atmosphere unless otherwise specified.

An argon atmosphere or a nitrogen atmosphere means that the reaction flask is connected to a balloon containing about 1 L of argon or nitrogen.

A hydrogen atmosphere means that the reaction flask is connected to a balloon containing about 1 L of hydrogen.

The pressurized hydrogenation reaction is performed using a Parr 3916EKX hydrogenator, a Qinglan QL-500 hydrogenator or a HC2-SS hydrogenator.

The hydrogenation reaction usually involves 3 cycles of vacuumization and hydrogen purge.

The microwave reaction is performed in a CEM Discover-S 908860 microwave reactor.

In the examples, a solution refers to an aqueous solution unless otherwise specified.

In the examples, the reaction temperature was room temperature, i.e., 20 °C to 30 °C, unless otherwise specified.

The reaction progress in the examples is monitored by thin layer chromatography (TLC). The developing solvent for reactions, the eluent system for column chromatography purification and the developing solvent system for thin layer chromatography include: A: dichloromethane/methanol system, B: n-hexane/ethyl acetate system, C: petroleum ether/ethyl acetate system, D: petroleum ether/ethyl acetate/methanol system, and E: petroleum ether/tetrahydrofuran system. The volume ratio of the solvents is adjusted according to the polarity of the compound, or by adding a small amount of basic or acidic reagents such as triethylamine and acetic acid.

Example 1

Step 1

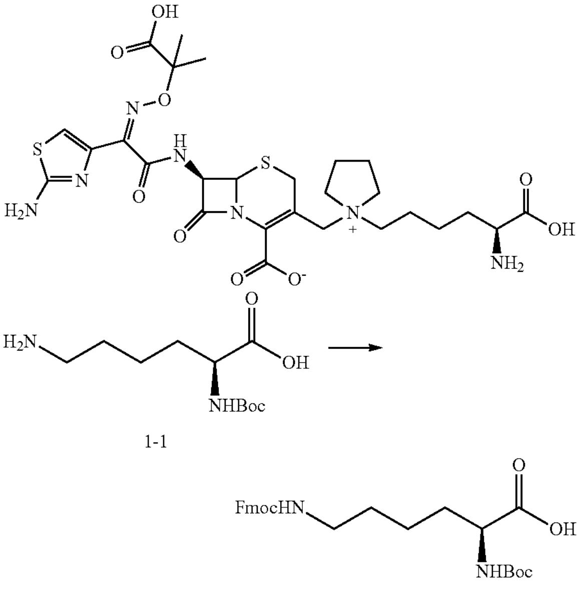

1-1

1-2

Compound 1-1 (2.46 g, 10 mmol) was dissolved in 5% aqueous sodium bicarbonate solution (86 mL), and the solution was stirred until it was clarified, followed by the addition of Fmoc-OSu (3.37 g, 10 mmol, dissolved in 24 mL of dioxane). After the addition, the mixture was reacted overnight. The reaction mixture was concentrated under reduced pressure to remove most of the dioxane, added with hydrochloric acid to adjust the pH, extracted with ethyl acetate for liquid separation, dried over magnesium sulfate, filtered and evaporated to dryness to give compound 1-2 (5.2 g), which was directly used in the next step.

LC/MS (ESI): m/z 469.1 $[M+H]^+$

Step 2

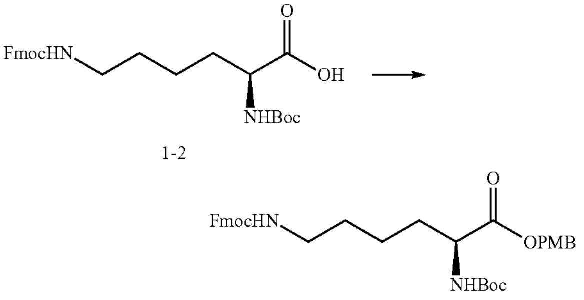

1-2

1-3

Compound 1-2 (2.08 g, 4 mmol), EDCI (1.15 g, 6 mmol) and DMAP (49 mg, 0.4 mmol) were dissolved in dichloromethane (20 mL), followed by the addition of p-methoxybenzyl alcohol (828 mg, 6 mmol), and the mixture was stirred. After the reaction was completed, the reaction mixture was concentrated under reduced pressure, slurried with methyl tert-butyl ether, filtered, and concentrated in vacuum to remove the solvent to give compound 1-3 (1.31 g, 2.23 mmol, yield 56%).

LC/MS (ESI): m/z 589.1 [M+H]+

Step 3

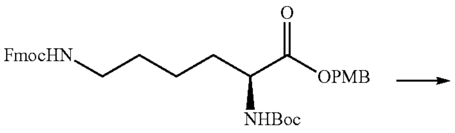

1-3

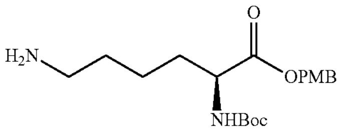

1-4

Compound 1-3 (945 mg, 1.6 mmol) were dissolved with dichloromethane (10 mL), followed by the addition of DBU (243 mg, 1.6 mmol), and the mixture was stirred. After the reaction was completed, the reaction was quenched with aqueous citric acid solution, and the reaction mixture was diluted with MTBE for liquid separation. The aqueous phase was adjusted to pH 8 with 1 N NaOH solution, extracted with dichloromethane, dried, filtered and concentrated to give compound 1-4 (562 mg, yield 96%).

LC/MS (ESI): m/z 367.1 [M+H]+

Step 4

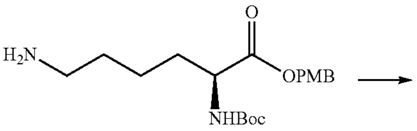

1-4

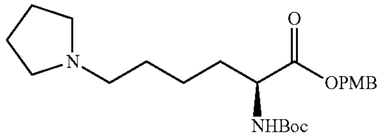

1-5

Compound 1-4 (534 mg, 1.46 mmol) was dissolved with acetonitrile (20 mL), followed by the addition of 1,4-dibromobutane (330 mg, 1.53 mmol) and N,N-diisopropylethylamine (395 mg, 3.06 mmol), and the mixture was heated to reflux for 6 h. After the reaction was completed, the reaction was quenched with aqueous citric acid solution, and the reaction mixture was diluted with methyl tert-butyl ether for liquid separation. The aqueous phase was extracted with dichloromethane, evaporated to dryness under reduced pressure, adjusted to pH 8 with saturated aqueous sodium bicarbonate solution, and extracted with methyl tert-butyl ether. The organic phases were combined, dried over anhydrous $MgSO_4$, filtered and concentrated to give compound 1-5 (400 mg, yield 66%).

LC/MS (ESI): m/z 421.1 [M+H]+

Step 5

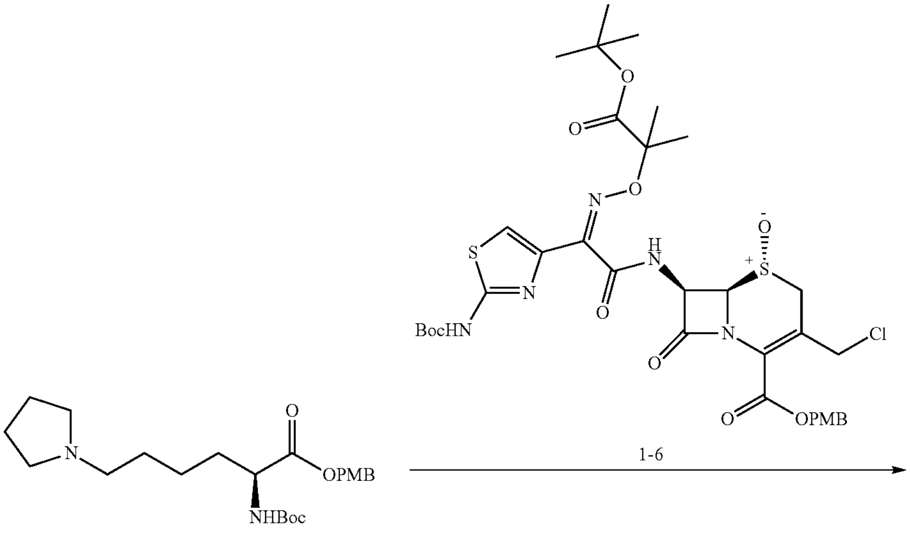

1-6

1-5

-continued

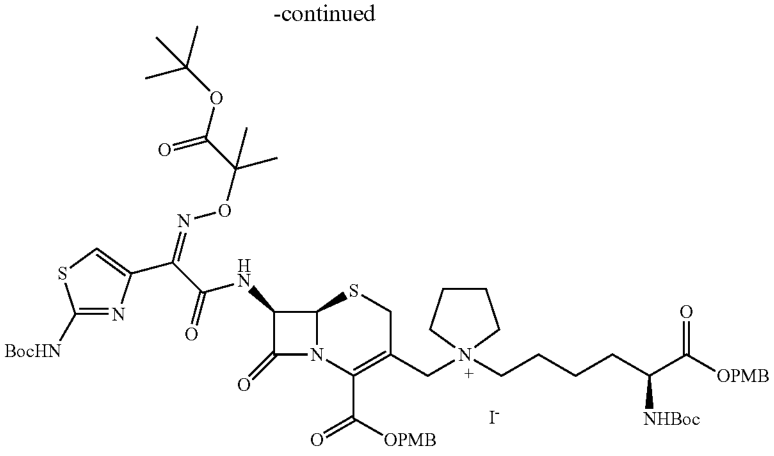

1-7

Compound 1-5 (211 mg, 0.5 mmol), compound 1-6 (synthesized by the method described in the patent WO2016035847, 360 mg, 0.45 mmol) and sodium iodide (225 mg, 1.5 mmol) were dissolved with N,N-dimethylformamide (0.8 mL), and the solution was stirred. After the reaction was completed, the reaction mixture was cooled to 0 °C, added with potassium iodide (523 mg, 3.15 mmol), N,N-dimethylformamide (1.6 mL) and acetyl chloride (177 mg, 2.25 mmol), and stirred. After the reaction was completed, the reaction mixture was added to a 5% aqueous $Na_2S_2O_5$, stirred, filtered, and concentrated under reduced pressure to remove the solvent to give compound 1-7 (540 mg).

LC/MS (ESI): m/z 1164.2 $[M]^+$

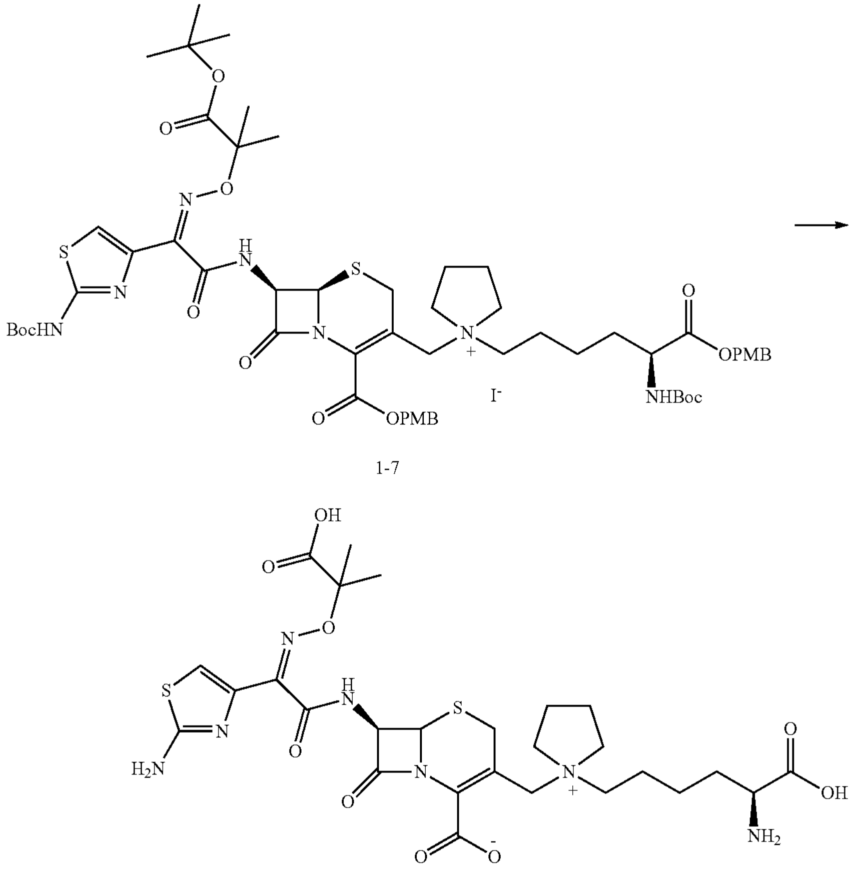

1-7

1

Compound 1-7 (233 mg) was dissolved with anisole (0.5 mL) and trifluoroacetic acid (2 mL), and the solution was stirred. After the reaction was completed, the reaction solution was concentrated under reduced pressure, and the residue was dissolved with methyl tert-butyl ether, and washed with dilute hydrochloric acid. The aqueous phases were combined and concentrated under reduced pressure to give a crude product (110 mg), which was purified by HPLC to give compound 1 (4 mg).

LC/MS (ESI): m/z 668.0 $[M+H]^+$ $^1$H-NMR (400 MHz, DMSO-$d_6$) δ: 1.27-1.38 (m, 1H), 1.44 (s, 3H), 1.45 (s, 3H), 1.56-1.80 (m, 4H), 1.82-1.96 (m, 1H), 1.97-2.15 (m, 4H), 3.04-3.20 (m, 3H), 3.27-3.71 (m, 5H), 3.92 (d, 1H), 3.96-4.10 (m, 2H), 4.65-4.88 (m, 1H), 5.27 (d, 1H), 5.90-5.93 (m, 1H), 6.71 (s, 1H), 7.32 (s, 2H), 8.06-8.56 (m, 2H), 9.50 (d, 1H), 12.62 (brs, 1H).

Example 2

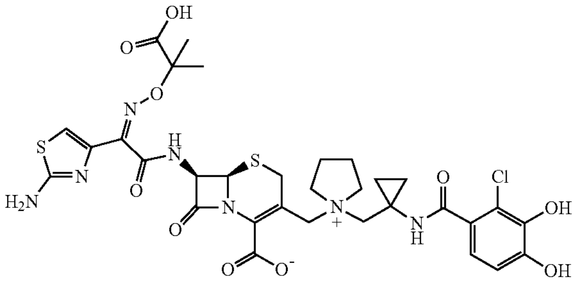

Step 1

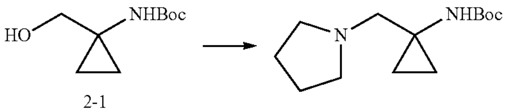

2-1

2-2

Compound 2-1 (2.0 g, 10.69 mmol, 1 eq) was dissolved with dichloromethane (10 mL), and triethylamine (3.24 g, 32.07 mmol, 3 eq) was added, followed by the dropwise addition of methanesulfonyl chloride (2.43 g, 21.38 mmol, 2 eq). The mixture was reacted at room temperature. After the reaction was completed, the reaction mixture was diluted with dichloromethane, washed with water, dried, filtered and concentrating to give a crude product. The crude product (2.6 g, about 8.96 mmol) was dissolved in acetonitrile (20 mL), followed by the addition of potassium carbonate (2.76 g, 20 mmol, 2.23 eq), tetrahydropyrrole (1.06 g, 15 mmol, 1.67 eq), and the mixture was stirred at 40 °C overnight. After the reaction was completed, the reaction mixture was concentrated under reduced pressure to remove the solvent, dissolved with dichloromethane, washed with water, dried, filtered and concentrated under reduced pressure, and the residue was separated by column chromatography to give compound 2-2 (1.7 g, yield 79%).

Step 2

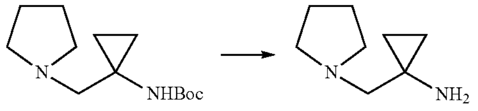

2-2

2-3

Compound 2-2 (300 mg, 1.25 mmol) was dissolved with dichloromethane (4 mL), followed by the addition of trifluoroacetic acid (1 mL), and the mixture was stirred. After the reaction was completed, the reaction mixture was concentrated under reduced pressure, diluted with methanol, neutralized with potassium carbonate, filtered and concentrated to give crude compound 2-3, which was directly used in the next step.

LC/MS (ESI): m/z 141.1 $[M+H]^+$

Step 3

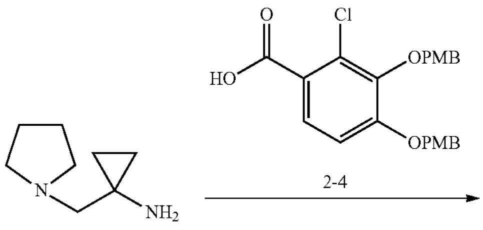

2-4

2-3

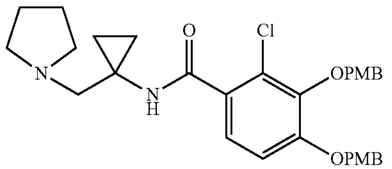

2-5

The crude compound 2-3 obtained from the previous step, compound 2-4 (synthesized by the method described in the patent CN106661052A, 1.07 g, 2.5 mmol) and HATU (1.43 g, 3.75 mmol) were dissolved in N,N-dimethylformamide (10 mL), followed by the addition of DIPEA (1.1 mL, 6.25 mmol), and the reaction mixture was stirred overnight. After the reaction was completed, the reaction mixture was added with aqueous sodium hydroxide, stirred and filtered, and the filter cake was washed with water and concentrated in vacuum to remove the solvent to give a crude product, which was separated by column chromatography to give compound 2-5 (600 mg, 1.09 mmol, yield 87% over two steps).

LC/MS (ESI): m/z 555.1 $[M+H]^+$

Step 4

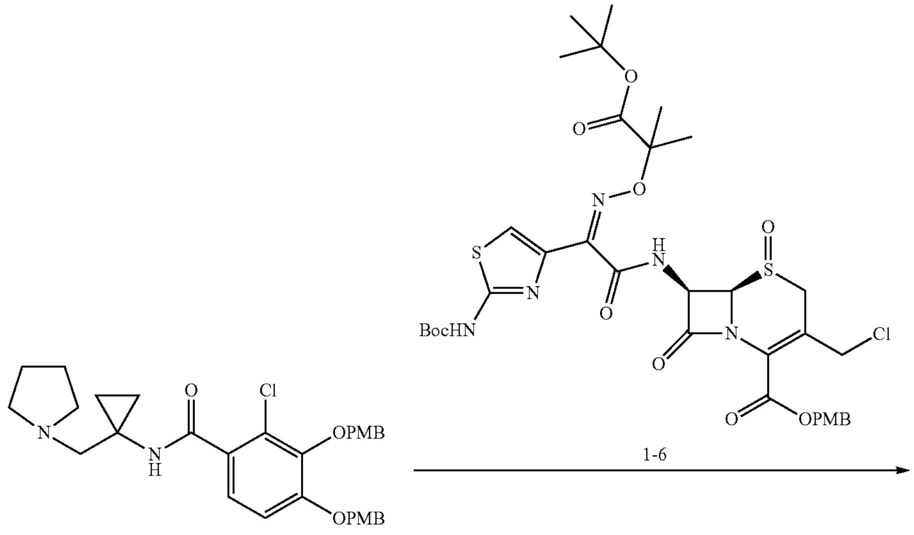

2-5

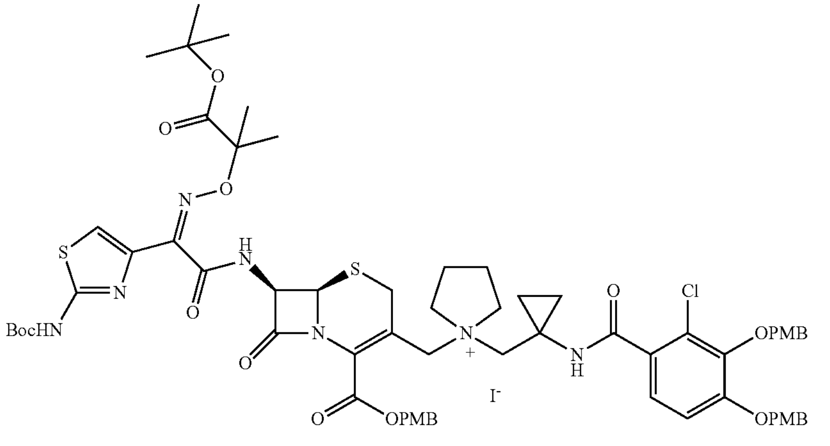

2-6

Compound 2-5 (219 mg, 0.4 mmol), compound 1-6 (398 mg, 0.5 mmol), sodium iodide (180 mg, 1.2 mmol) and boric acid (7.5 mg, 0.12 mmol) were dissolved with N-methylpyrrolidone (1 mL), and the solution was stirred. After the reaction was completed, the reaction mixture was cooled with ice water, added with KI (465 mg, 2.8 mmol), N-methylpyrrolidone (2 mL) and acetyl chloride (188 mg, 2.4 mmol), and stirred. After the reaction was completed, the reaction mixture was directly added into a large amount of aqueous sodium metabisulfite solution in an ice bath, stirred and filtered, and the filter cake was washed with water and concentrated in vacuum to remove the solvent to give compound 2-6 (635 mg).

LC/MS (ESI): m/z 1294.4 $[M]^+$

Step 5

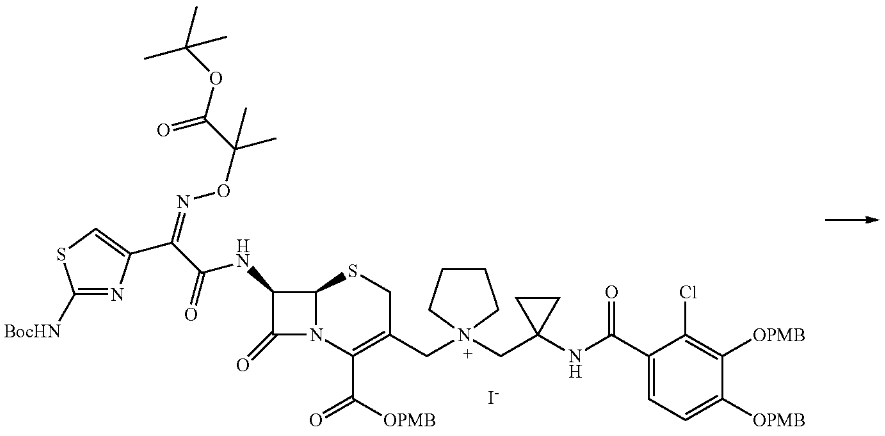

2-6

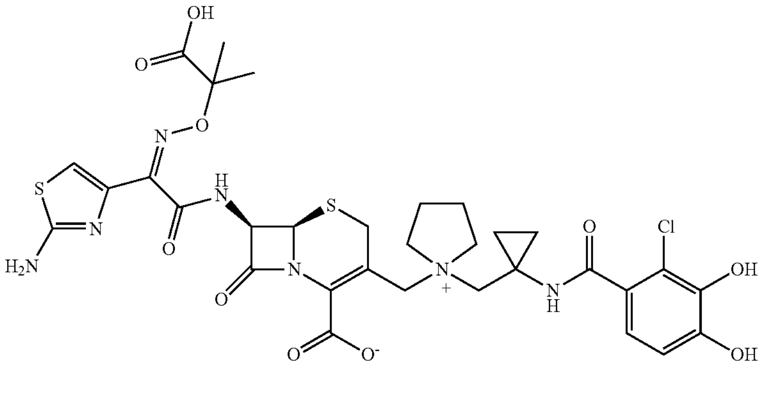

2

Compound 2-6 (200 mg) was dissolved with anisole (0.4 mL) and trifluoroacetic acid (1.6 mL), and the solution was stirred. After the reaction was completed, the reaction mixture was added with MTBE (4 mL) to precipitate a solid and filtered, and the solid was rinsed with MTBE, and dried to give a crude product (170 mg), which was purified by HPLC to give compound 2 (4.2 mg).

LC/MS (ESI): m/z 777.9 $[M+H]^+$ $^1$H-NMR (400 MHz, DMSO-$d_6$) δ: 1.00-1.08 (m, 4H), 1.44 (s, 3H), 1.45 (s, 3H), 1.91-2.14 (m, 4H), 3.36-3.44 (m, 2H), 3.48-3.60 (m, 3H), 3.60-3.74 (m, 3H), 3.80 (d, 1H), 4.18 (d, 1H), 5.01 (d, 1H), 5.18-5.24 (m, 1H), 5.67-5.82 (m, 1H), 6.66-6.84 (m, 3H), 7.29 (s, 2H), 8.76 (s, 1H), 9.24-9.55 (m, 2H), 10.26 (br s, 1H).

Example 3

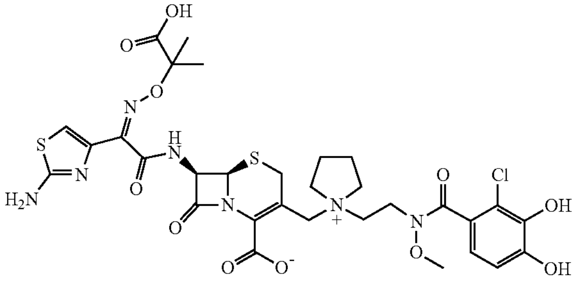

Step 1

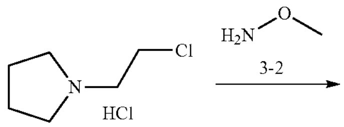

3-2

3-1

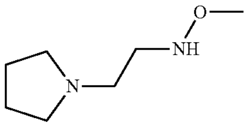

3-3

Compound 3-1 (5 g, 29.40 mmol) and compound 3-2 (3.68 g, 44.10 mmol) were dissolved in methanol (30 mL) and water (15 mL), and the solution was stirred. After potassium carbonate (14.22 g, 102.89 mmol) was added, the mixture was heated to reflux. After the reaction was completed, the reaction mixture was cooled to room temperature and added with MTBE and aqueous NaOH solution for liquid separation, and the aqueous phase was extracted with MTBE. The organic phases were combined, dried over anhydrous sodium sulfate, filtered and concentrated to dryness to give compound 3-3 (0.7 g).

LC/MS (ESI): m/z 145.1 $[M+H]^+$

Step 2

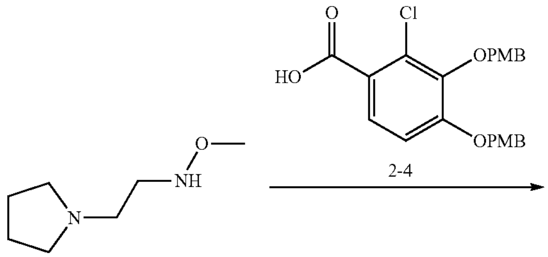

2-4

3-3

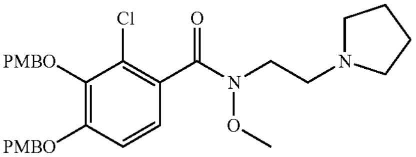

3-4

Compound 2-4 (1.9 g, 4.43 mmol) was added to tetrahydrofuran (30 mL) and stirred in an ice water bath, and triethylamine (0.98 mL, 7.09 mmol) was added, followed by the dropwise addition of methanesulfonyl chloride (0.45 mL, 5.80 mmol). After the addition, the mixture was reacted in an ice water bath. Compound 3-3 was dissolved in THE (10 mL), and the solution was added dropwise to the above reaction mixture. After the addition, the resulting reaction mixture was heated to room temperature and reacted. Ethyl acetate was added, and the organic phase was washed with saturated brine, dried over anhydrous sodium sulfate, filtered, and concentrated to dryness to give a crude product. The crude product was purified by HPLC to give compound 3-4 (220 mg).

LC/MS (ESI): m/z 555.1 $[M+H]^+$

Step 3

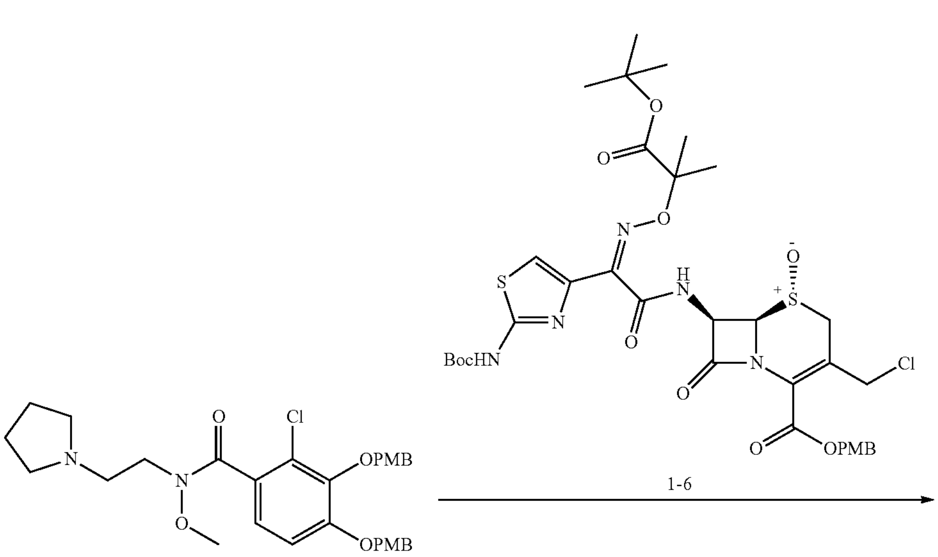

1-6

3-4

-continued

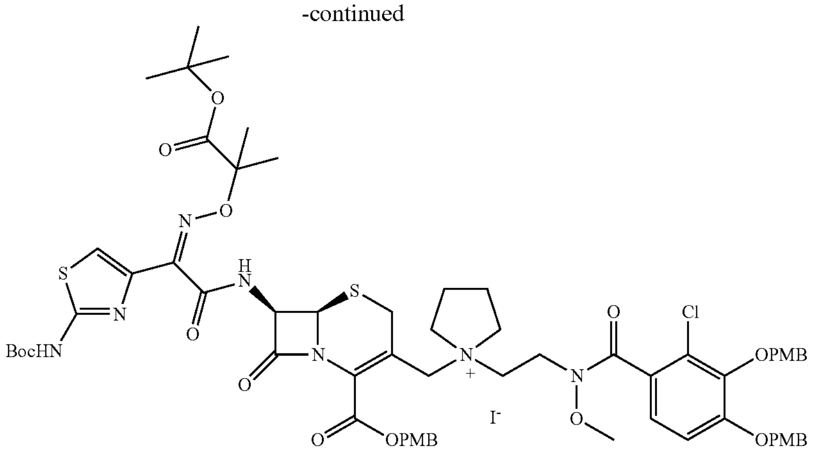

3-5

Compound 1-6 (315 mg, 0.395 mmol), compound 3-4 (220 mg, 0.395 mmol) and sodium iodide (178 mg, 1.19 mmol) were added to N,N-dimethylformamide (0.9 mL), and the mixture was stirred. After the reaction was completed, the flask was cooled in an ice water bath, followed by the addition of $PBr_3$ (751 mg, 2.77 mmol), and the mixture was stirred. After the reaction was completed, the reaction mixture was added dropwise to aqueous $NaHSO_3$ solution and filtered, and the filter cake was washed with clear water and dried in vacuum to obtain crude compound 3-5 (623 mg).

LC/MS (ESI): m/z 1298.1 $[M]^+$

Step 4

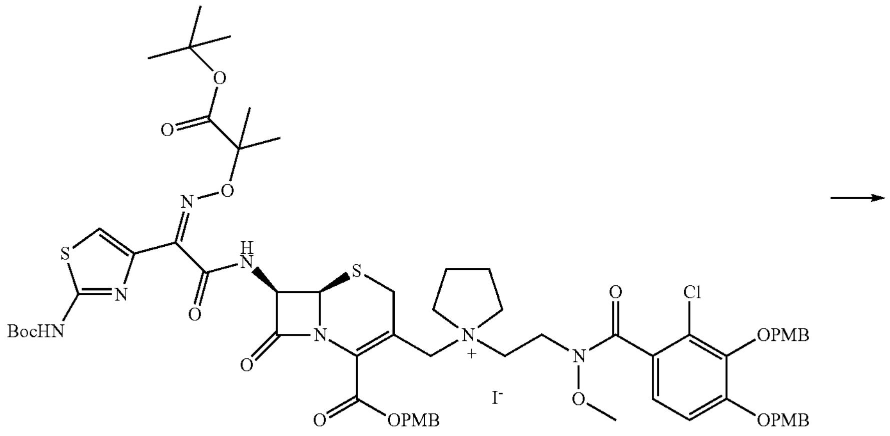

3-5

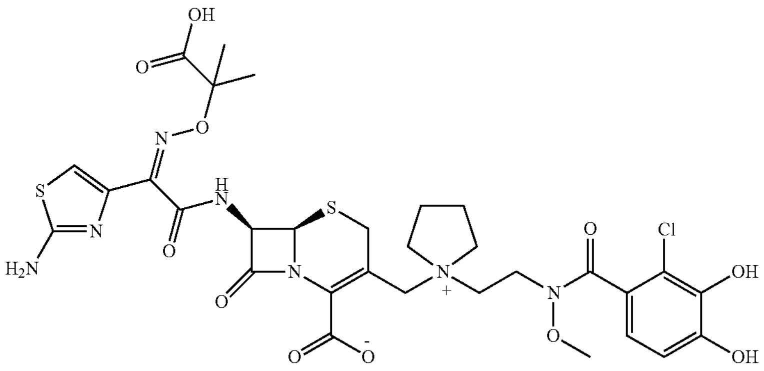

3

Compound 3-5 (200 mg, 0.154 mmol) was added to anisole (0.4 mL) and trifluoroacetic acid (1.6 mL), and the mixture was reacted at room temperature. The reaction mixture was added with methyl tert-butyl ether, stirred and filtered. The filter cake was rinsed with MTBE and dried to give a crude product (112 mg). The crude product was purified by HPLC to give compound 3 (7.1 mg).

LC/MS (ESI): m/z 781.9 $[M+H]^+$ $^1$H-NMR (400 MHz, DMSO-$d_6$) δ: 1.43 (s, 3H), 1.46 (s, 3H), 1.94-2.09 (m, 3H), 2.10-2.21 (m, 1H), 3.43-3.56 (m, 8H), 3.57-3.67 (m, 3H), 3.67-3.83 (m, 2H), 3.92-4.06 (m, 1H), 4.07-4.36 (m, 3H), 5.03-5.11 (m, 1H), 5.15 (d, 1H), 5.69-5.75 (m, 1H), 6.71-6.82 (m, 3H), 7.27 (s, 2H), 8.15 (s, 1H).

Example 4

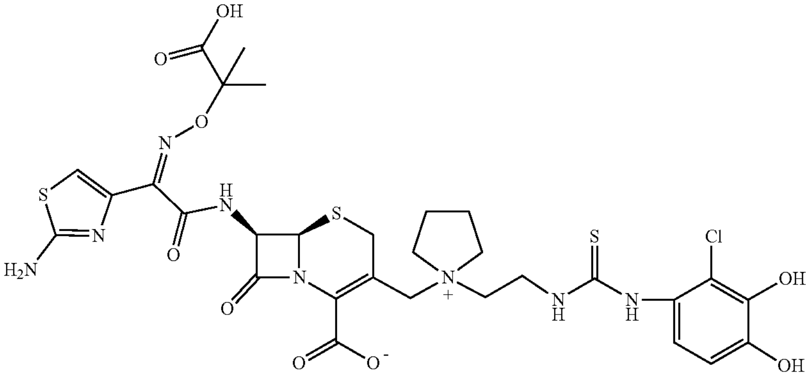

Step 1

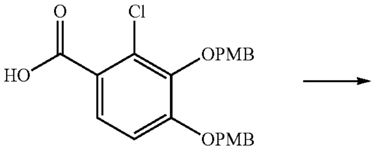

2-4

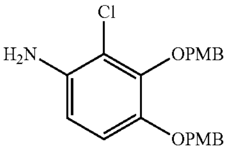

4-1

Compound 2-4 (3.0 g, 7.0 mmol) and triethylamine (0.85 g, 8.39 mmol) were added to toluene (50 mL), and diphenyl phosphoryl azide (2.31 g, 8.39 mmol) was slowly added dropwise. After the addition, the mixture was stirred overnight, heated to 110 °C and reacted, added with 9-fluorenylmethanol (2.06 g, 10.49 mmol), and reacted at 110 °C. After the reaction was completed, the reaction mixture was cooled to room temperature, added with piperidine (2.98 g, 34.97 mmol) and stirred overnight. The heating was stopped, and the reaction mixture was concentrated to remove toluene, added with dichloromethane and water, and stirred for liquid separation. The aqueous phase was extracted with dichloromethane, and the organic phases were combined, dried, filtered and concentrated to give a crude product. The crude product was directly purified by column chromatography to give compound 4-1 (462 mg, yield 17%).

LC/MS(ESI): m/z 400.0 $[M+H]^+$

Step 2

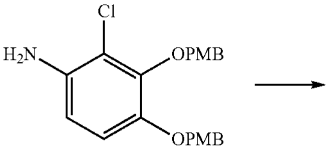

4-1

-continued

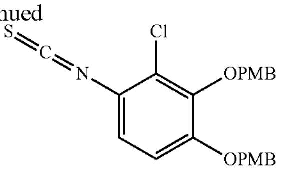

4-2

Compound 4-1 (0.46 g, 1.15 mmol) was dissolved with dichloromethane (8 mL), and thiophosgene (0.40 g, 3.45 mmol) was added, followed by the addition of DMAP (0.70 g, 5.73 mmol) at 0 °C. The mixture was heated to room temperature and stirred. After the reaction was completed, the reaction was directly purified by column chromatography to give compound 4-2 (432 mg, yield 85%).

Step 3

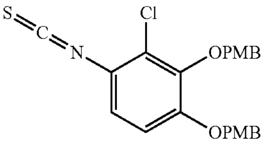

4-2

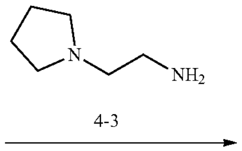

4-3

-continued

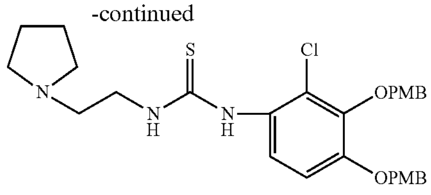

4-4

Compound 4-2 (0.43 g, 1.01 mmol), compound 4-3 (0.13 g, 1.1 mmol) and DMAP (0.61 g, 5.0 mmol) were added to a reaction flask, followed by the addition of DMF (0.5 mL). The mixture was stirred at room temperature overnight. The reaction mixture was added with water to precipitate a solid and filtered, and the filter cake was collected purified by column chromatography to give compound 4-4 (467 mg, yield 83%).

LC/MS(ESI):m/z 556.0 $[M+H]^+$

Step 4

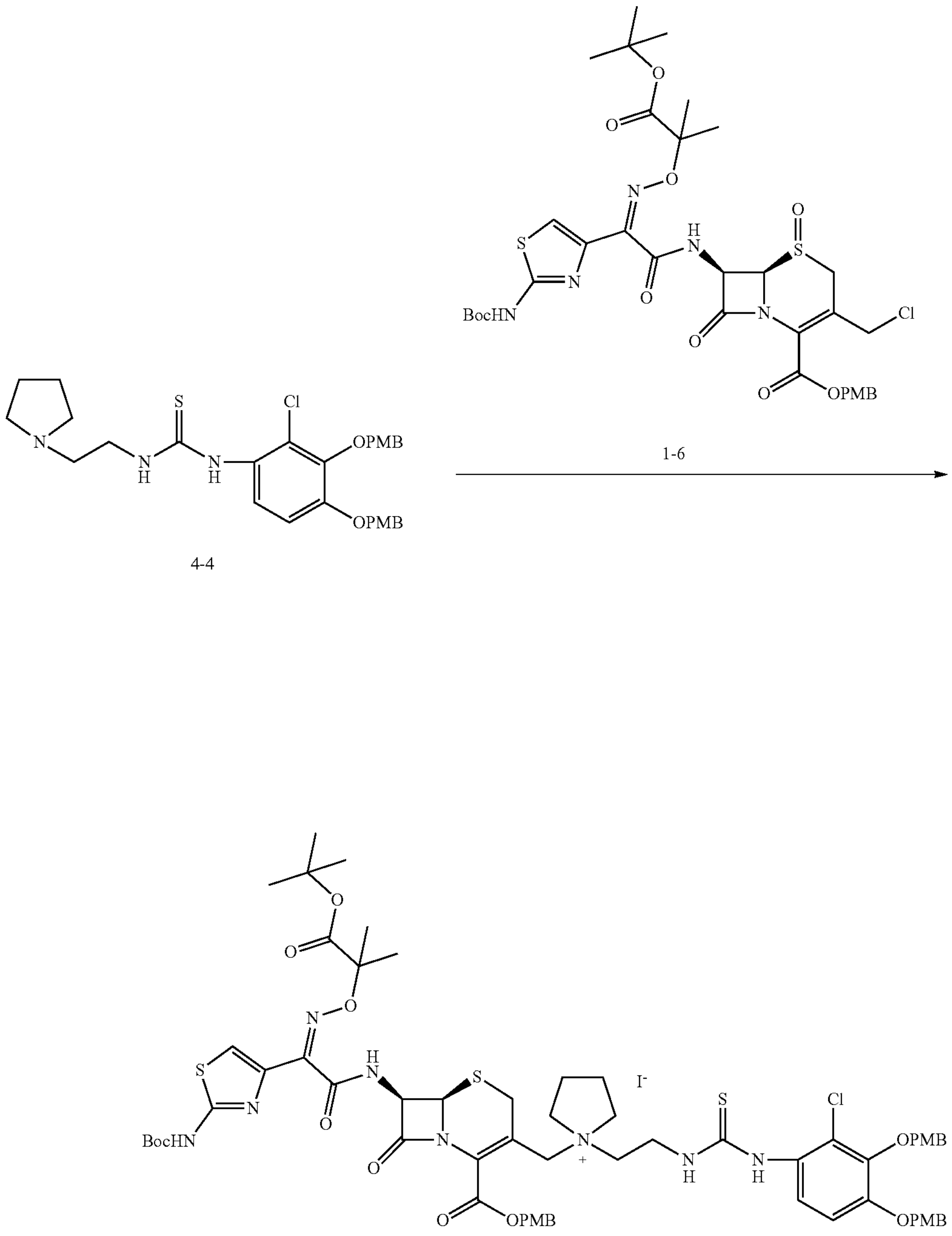

4-4

4-5

Compound 4-4 (200 mg, 0.36 mmol), compound 1-6 (315 mg, 0.4 mmol) and sodium iodide (180 mg, 1.2 mmol) were dissolved with NMP (0.9 mL), and the mixture was stirred. After the reaction was completed, the reaction mixture was cooled to 0 °C, added with $PBr_3$ (650 mg, 2.4 mmol) and stirred. After the reaction was completed, the reaction solution was added to aqueous $Na_2S_2O_5$ solution in an ice bath, stirred and filtered, and the filter cake was with water and concentrated in vacuum to remove the solvent to give compound 4-5 (515 mg).

LC/MS (ESI): m/z 1299.0 $[M]^+$

Step 5

Compound 4-5 (200 mg, 0.154 mmol) was added to a reaction flask, followed by the addition of anisole (0.4 mL) and trifluoroacetic acid (1.6 mL), and the mixture was stirred. After the reaction was completed, the reaction mixture was added with MTBE and filtered, and the filter cake was rinsed with MTBE and dried to give a crude product (68 mg). The crude product was purified by HPLC to give compound 4 (4.4 mg).

LC/MS (ESI): m/z 782.9 $[M+H]^+$ $^1$H-NMR (400 MHz, DMSO-$d_6$) δ: 1.43 (s, 3H), 1.44 (s, 3H), 1.46-1.57 (m, 1H), 1.78-2.11 (m, 4H), 2.96 (d, 1H), 3.41 (d, 2H), 3.48-3.93 (m, 9H), 4.57 (s, 1H), 5.26 (s, 1H), 5.38-5.45 (m, 1H), 6.57 (d, 1H), 6.64 (d, 1H), 6.88 (s, 1H), 7.22-7.51 (m, 2H), 9.05 (s, 1H), 9.22-9.34 (m, 1H), 9.36 (s, 1H), 9.77 (brs, 1H).

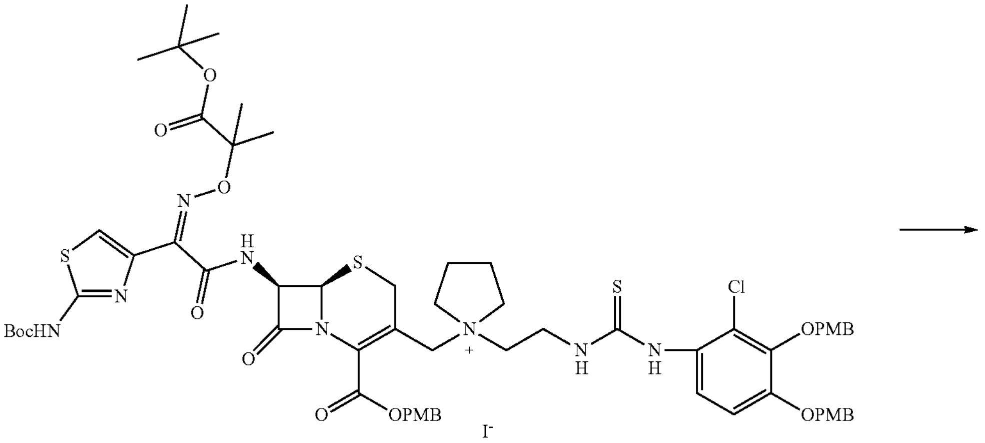

4-5

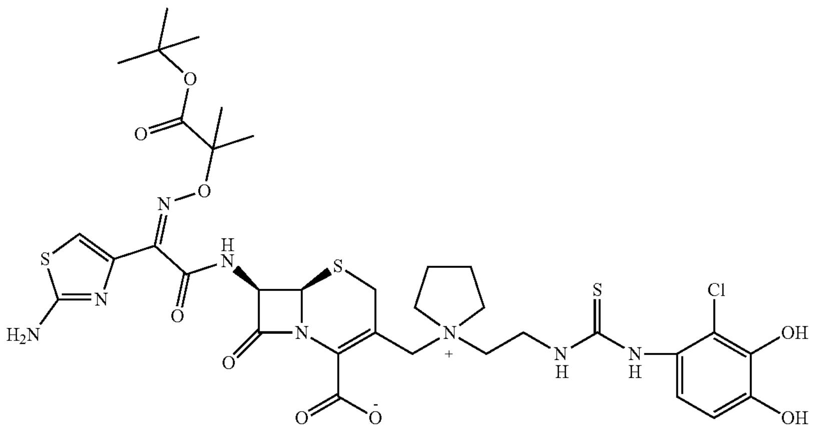

4

Example 5

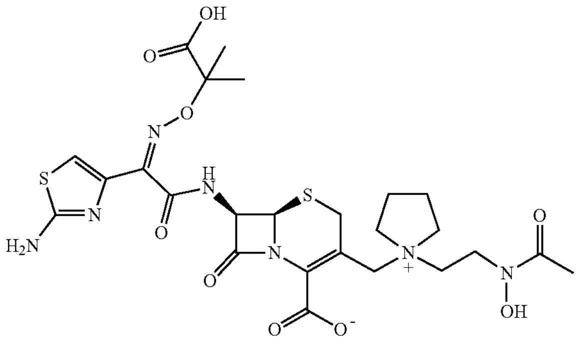

Step 1

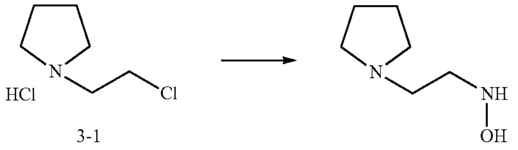

3-1

5-1

Compound 3-1 (50.0 g, 0.294 mol), hydroxylamine hydrochloride (40.8 g, 0.59 mol), sodium carbonate (62.3 g, 0.59 mol), ethanol (300 mL) and water (150 mL) were added to a three-necked flask. The mixture was reacted in an oil bath at 50 °C. After the reaction was completed, the reaction mixture was concentrated, added with isopropyl ether and water and stirred for liquid separation. The organic phase was washed with saturated brine, dried and concentrated to give a crude product, which was distilled under reduced pressure to give compound 5-1 (12.5 g, yield 33%).

LC/MS (ESI): m/z 131.1 $[M+H]^+$

Step 2

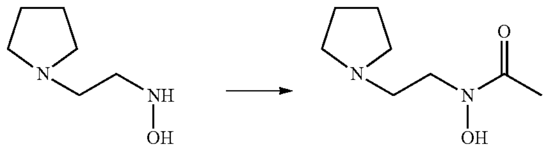

5-1

5-2

Compound 5-1 (1.0 g, 7.7 mmol), acetonitrile (10 mL) and sodium bicarbonate (1.3 g, 15.4 mmol) were added to a single-necked flask, and the mixture was cooled in an ice water bath, added dropwise with acetyl chloride (0.66 g, 8.5 mmol), and reacted in an ice water bath. After the reaction was completed, the reaction mixture was added with dichloromethane and water for liquid separation. The aqueous phase was extracted with dichloromethane, dried and concentrated to give compound 5-2 (0.9 g, yield 68%).

LC/MS (ESI): m/z 173.1 $[M+H]^+$

Step 3

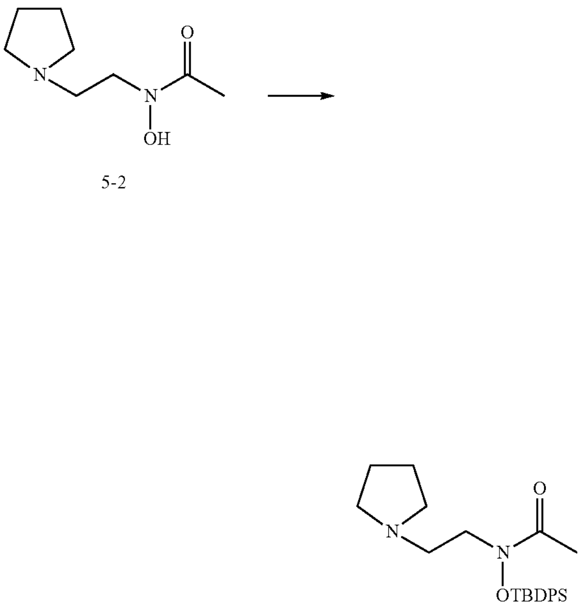

5-2

5-3

Compound 5-2 (510 g, 3 mmol), DCM (10 mL) and imidazole (410 mg, 6 mmol) were added to a single-necked flask, followed by the dropwise addition of tert-butyldiphenylchlorosilane (910 mg, 3.3 mmol). After the reaction was completed, the reaction was added with DCM and $H_2O$ and stirred for liquid separation. The aqueous phase was extracted with DCM. The organic phase was washed with saturated brine, dried, concentrated and purified by column chromatography to give compound 5-3 (1.1 g, yield 92%).

LC/MS (ESI): m/z 411.1 $[M+H]^+$

Step 4

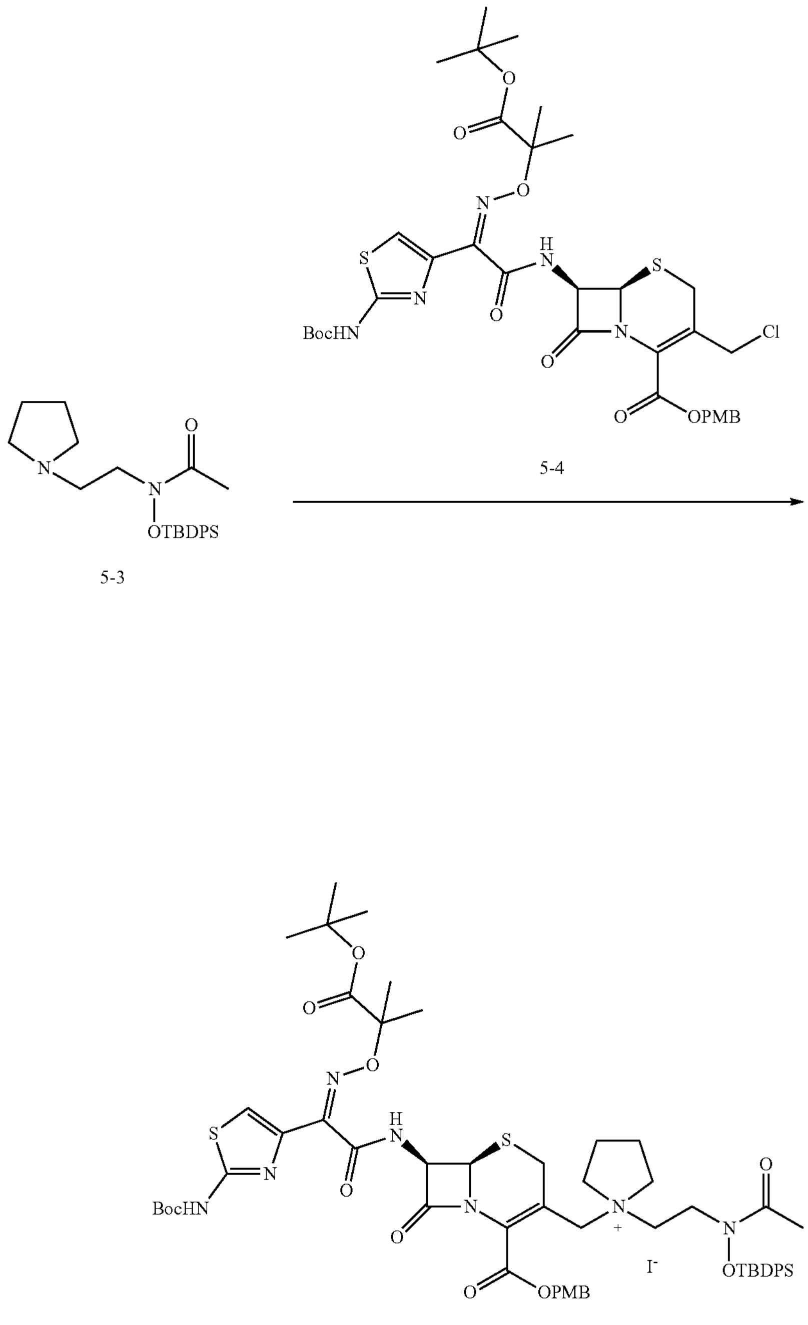

5-4

5-3

5-5

Compound 5-4 (synthesized by the method described in the patent WO2016035847, 330 mg, 0.43 mmol), compound 5-3 (210 mg, 0.5 mmol), sodium iodide (194 mg, 1.3 mmol) and NMP (1.0 mL) were added to a single-necked flask, and the mixture was reacted at room temperature. After the reaction was completed, the reaction mixture was added dropwise to a 5% aqueous sodium bisulfite solution and filtered, and the filter cake was washed with water and concentrated in vacuum to remove the solvent to give compound 5-5 (230 mg).

LC/MS (ESI): m/z 1154.1 $[M]^+$

Step 5

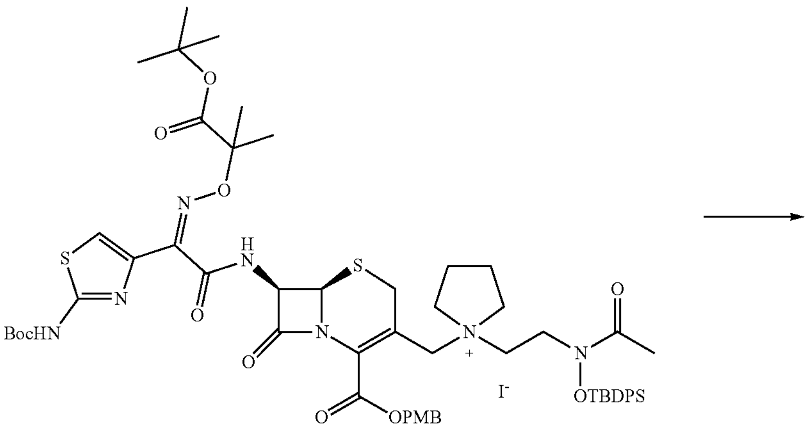

5-5

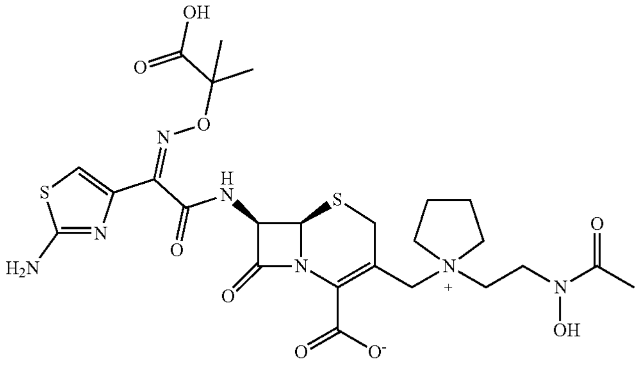

5

Compound 5-5 (200 mg, 0.164 mmol) was dissolved with anisole (0.4 mL) and trifluoroacetic acid (1.6 mL), and the solution was stirred. After the reaction was completed, the reaction mixture was added with MTBE and filtered, and the filter cake was rinsed with MTBE and dried to give a crude product (66 mg). The crude product was purified by HPLC to give compound 5 (1.9 mg).

LC/MS (ESI): m/z 640.0 $[M+H]^+$ $^1$H-NMR (400 MHz, DMSO-$d_6$) δ: 1.39 (s, 3H), 1.45 (s, 3H), 1.89-2.16 (m, 4H), 2.00 (s, 3H), 3.41-3.90 (m, 12H), 3.93-4.25 (m, 2H), 5.13-5.17 (m, 1H), 5.70-5.80 (m, 1H), 6.73 (s, 1H), 7.22 (s, 2H), 8.20 (s, 1H).

Example 6

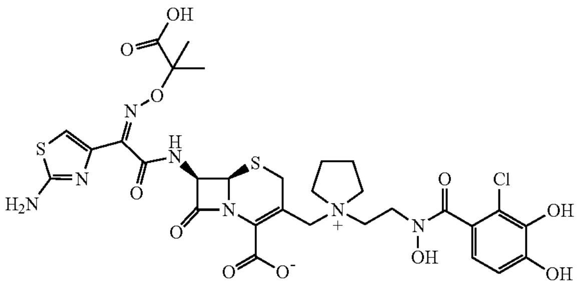

Step 1

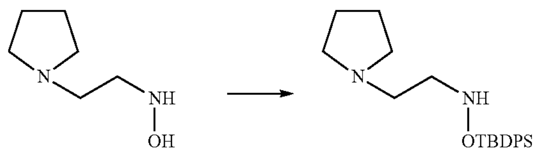

5-1 6-1

Compound 5-1 (0.5 g, 3.8 mmol), dichloromethane and imidazole (0.8 g, 11.5 mmol) were added to a reaction flask, and the mixture was cooled in an ice water bath, added dropwise with tert-butyldiphenylchlorosilane (1.15 g, 4.3 mmol), and stirred. After the reaction was completed, the reaction mixture was added with dichloromethane and water and stirred for liquid separation, and the aqueous phase was extracted with dichloromethane. The organic phases were combined, dried, concentrated and purified by column chromatography to give compound 6-1 (1.2 g, yield 85%).

LC/MS (ESI): m/z 369.1 $[M+H]^+$

Step 2

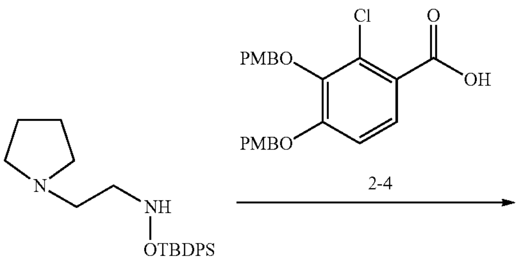

6-1 2-4

-continued

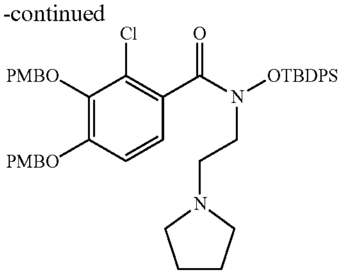

6-2

Compound 2-4 (428 mg, 1.0 mmol) and N,N-dimethylacetamide (4 mL) were added to a three-necked flask, and the mixture was cooled in an ice salt bath, added dropwise with MsCl (126 mg, 1.1 mmol) and TEA (111 mg, 1.1 mmol), and stirred. Compound 6-1 (410 mg, 1.0 mmol) was added and N-methylmorpholine (172 mg, 1.7 mmol) was added dropwise. After the reaction was completed, the reaction was quenched and the aqueous phase was extracted with EA. The organic phases were combined, dried, concentrated and purified by column chromatography to give compound 6-2 (240 mg, yield 30.8%).

LC/MS (ESI): m/z 779.0 $[M+H]^+$

Step 3

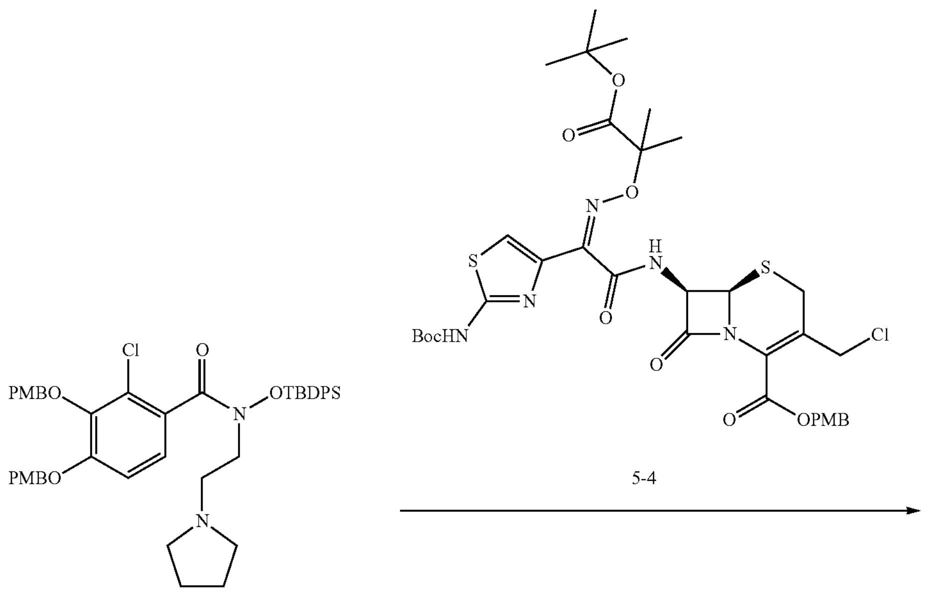

6-2 5-4

-continued
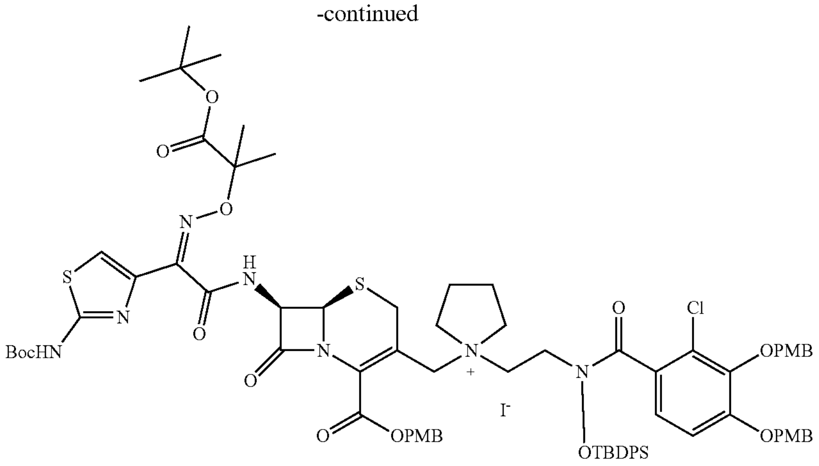
6-3
Compound 5-4 (270 mg, 0.35 mmol), compound 6-2 (240 mg, 0.31 mmol), sodium iodide (157 mg, 1.05 mmol) and NMP (0.81 mL) were added to a single-necked flask, and the mixture was reacted at room temperature overnight. The reaction mixture was added dropwise to a 5% aqueous sodium metabisulfite solution, filtered, and concentrated in vacuum to remove the solvent to give compound 6-3 (501 mg).
LC/MS (ESI): m/z 1523.1 $[M]^+$
Step 4
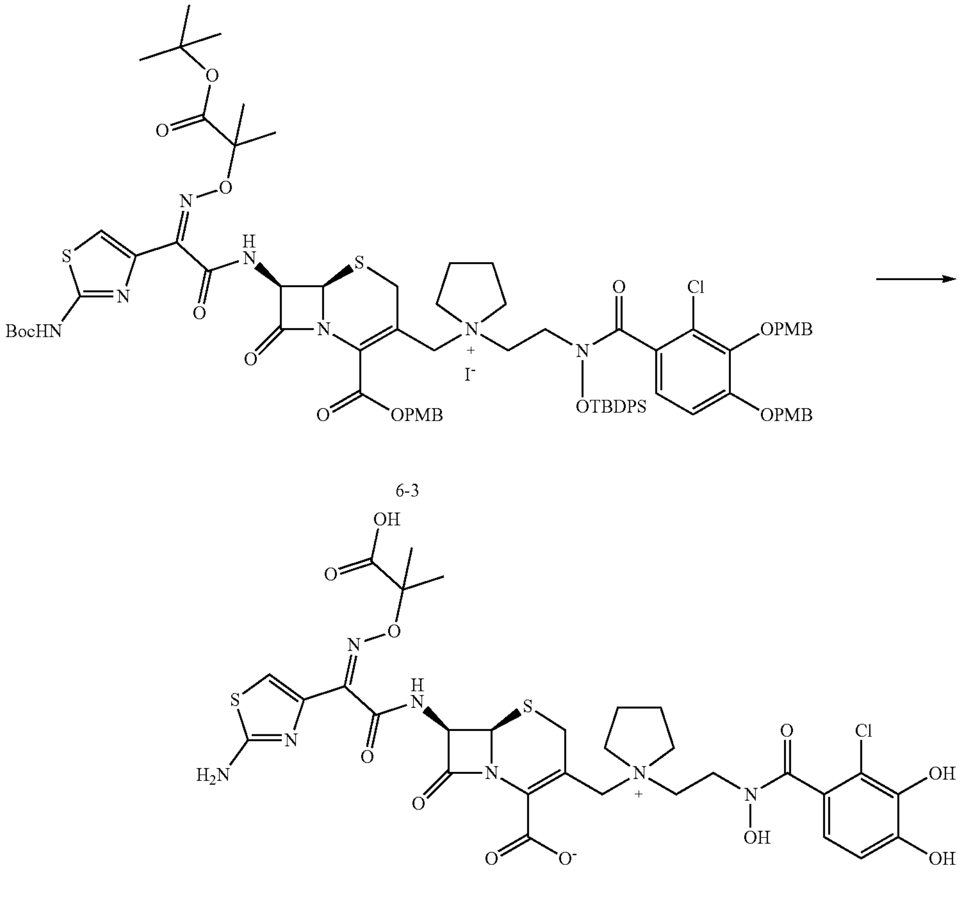
6-3
6

Compound 6-3 (501 mg) was added to a reaction flask, followed by the addition of TFA (4 mL) and anisole (1 mL), and the mixture was stirred. After the reaction was completed, the reaction mixture was added dropwise with MTBE and filtered, and the filter cake was washed with MTBE to give a crude product (210 mg), which was purified by reverse phase column chromatography to give compound 6 (10 mg).

LC/MS (ESI): m/z 767.8 $[M+H]^+$ $^1$H-NMR (400 MHz, DMSO-$d_6$) δ: 1.42 (s, 3H), 1.48 (s, 3H), 1.85-2.25 (m, 4H), 3.40-3.86 (m, 11H), 3.88-4.07 (m, 2H), 4.17-4.39 (m, 1H), 4.91-5.06 (m, 1H), 5.14-5.20 (m, 1H), 5.74-5.83 (m, 1H), 6.58-6.91 (m, 3H), 7.22 (s, 2H), 10.65 (br s, 1H), 11.60 (br s, 1H).

Example 7

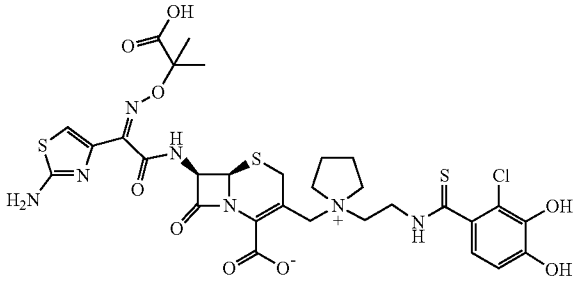

Step 1

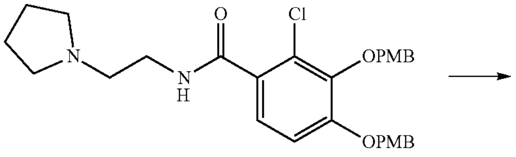

7-1

-continued

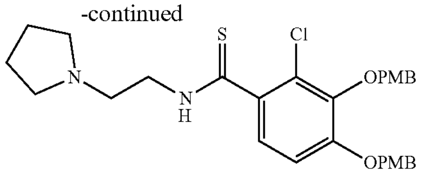

7-2

Compound 7-1 (0.40 g, 0.76 mmol) was weighed in a reaction flask (synthesized according to known document European Journal of Medicinal Chemistry, 2018, 155, 847-868), and under nitrogen atmosphere, anhydrous dichloromethane (4 mL) was added. The mixture was cooled to −40 °C, added dropwise with pyridine (0.20 g, 2.5 mmol) and trifluoromethanesulfonic anhydride (0.28 g, 0.99 mmol), heated to −5 °C and reacted for 2 h. Then the reaction mixture was reacted at room temperature for 2 h, cooled to −5 °C, added dropwise with ammonium sulfide, and reacted at room temperature. After the reaction, the reaction mixture was diluted with dichloromethane, washed with water, dried over anhydrous sodium sulfate, filtered, and concentrated under reduced pressure to remove the solvent, and the residue was separated and purified by silica gel column chromatography to give compound 7-2 (0.35 g, 0.65 mmol, yield 85%).

LC/MS (ESI): m/z 541.0 $[M+H]^+$

Step 2

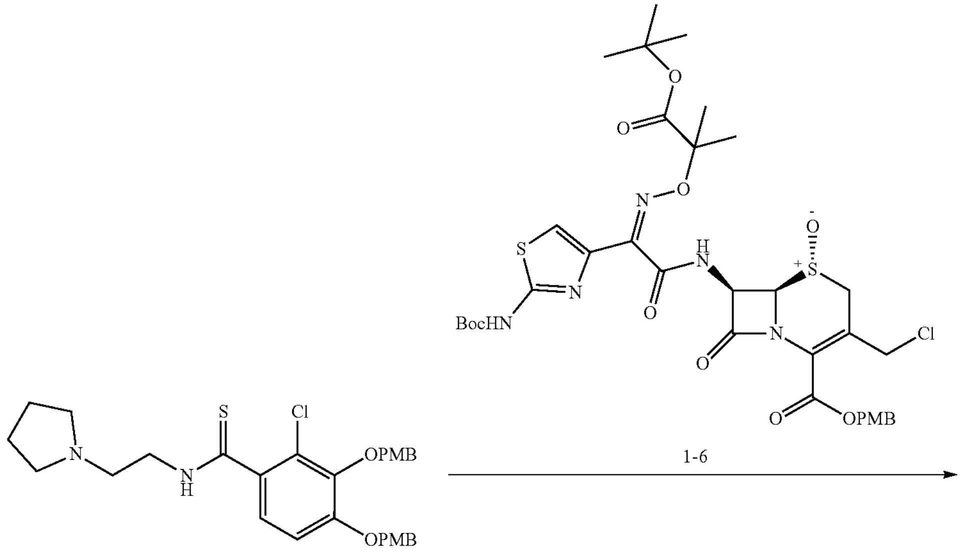

1-6

7-2

-continued

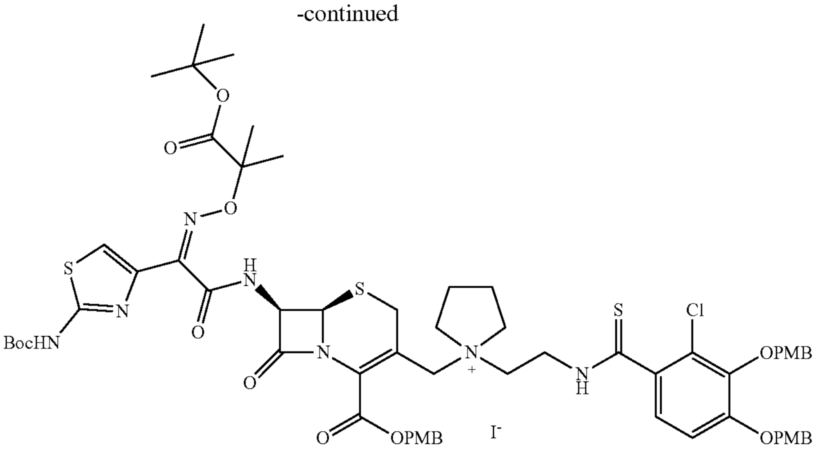

7-3

Compound 7-2 (350 mg, 0.65 mmol), compound 1-6 (647 mg, 0.81 mmol) and sodium iodide (369 mg, 2.46 mmol) were added to N,N-dimethylformamide (2 mL), and the mixture was stirred. After the reaction was completed, the flask was cooled in an ice water bath, followed by the addition of $PBr_3$ (360 mg, 1.33 mmol), and the mixture was stirred. After the reaction was completed, the reaction mixture was added dropwise to aqueous $NaHSO_3$ solution and filtered, and the filter cake was washed with clear water and dried in vacuum to give crude compound 7-3 (1.1 g).

Step 3

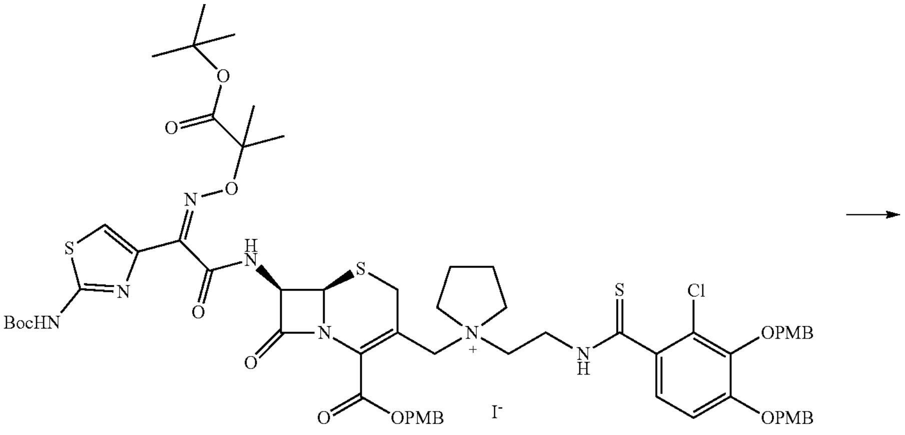

7-3

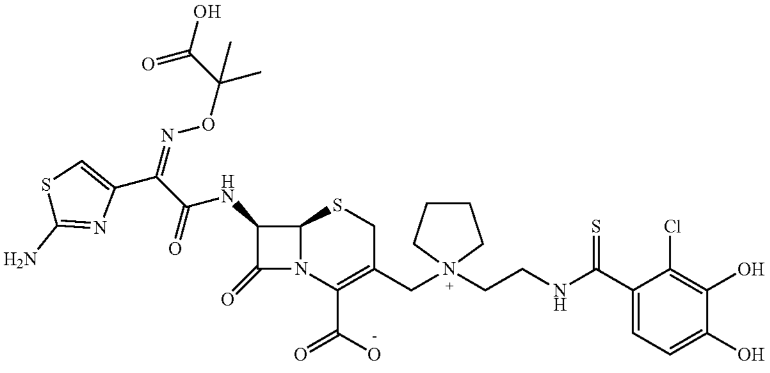

7

Compound 7-3 (1.06 g, 0.824 mmol) was added to anisole (2 mL) and trifluoroacetic acid (8 mL), and the mixture was reacted at room temperature. The reaction mixture was added with methyl tert-butyl ether, stirred and filtered. The filter cake was rinsed with MTBE and dried to give a crude product (550 mg). 50 mg of the crude product was purified by HPLC to give compound 7 (4.8 mg).

HRMS: 768.1334 $[M+H]^+$

Example 8

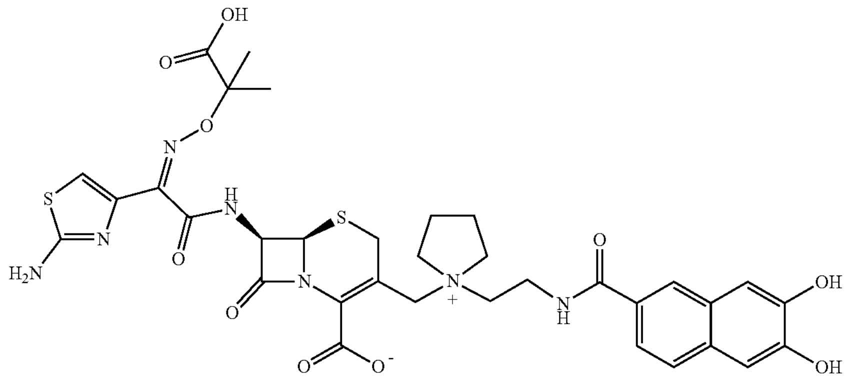

Step 1

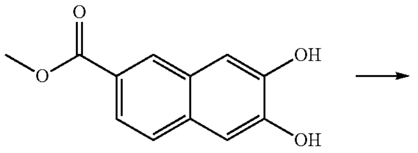

8-1

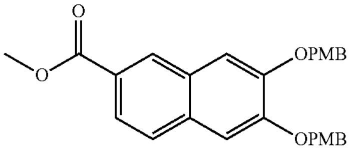

8-2

To a solution of compound 8-1 (200 mg, 0.92 mmol) (synthesized according to known document *J. Med. Chem.* 1997, 40, 1186-1194) in DMF (10 mL) were added PMBCl (503 mg, 3.21 mmol), $K_2CO_3$ (509 mg, 3.68 mmol) and NaI (138 mg, 0.92 mmol). The mixture was heated to 50 °C and stirred. The reaction mixture was added with water and extracted with ethyl acetate. The organic phase was washed with water and saturated brine sequentially, dried over anhydrous sodium sulfate, filtered and evaporated to dryness to give a crude product. The crude product was purified by reverse phase silica gel column chromatography to give compound 8-2 (105 mg, yield 25%).

$^1H$-NMR (400 MHz, DMSO-d6) δ: 3.76 (s, 6H), 3.18 (s, 3H), 5.18 (s, 2H), 5.19 (s, 2H), 6.96 (d, 4H), 7.44 (d, 4H), 7.53 (s, 1H), 7.67 (s, 1H), 7.81 (s, 2H), 8.44 (s, 1H).

Step 2

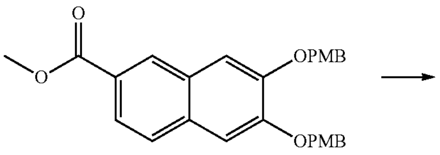

8-2

-continued

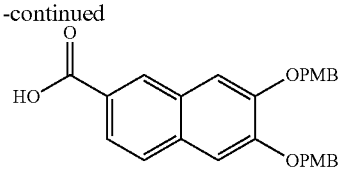

8-3

To a mixed solution of compound 8-2 (105 mg, 0.23 mmol) in THF (3 mL) and MeOH (1.5 mL) was added a solution of $LiOH \cdot H_2O$ (20 mg, 0.46 mmol) in $H_2O$ (1.5 mL). The mixture was stirred at room temperature. The reaction mixture was cooled to room temperature in an ice bath, adjusted to neutrality with 2 M HCl, and extracted with ethyl acetate. The organic phase was washed with water and saturated brine sequentially, dried over anhydrous sodium sulfate, filtered and evaporated to dryness to give crude compound 8-3 (100 mg).

$^1H$-NMR (400 MHz, DMSO-d6) δ: 3.76 (s, 6H), 5.18 (s, 2H), 5.19 (s, 2H), 6.96 (d, 4H), 7.44 (d, 4H), 7.52 (s, 1H), 7.64 (s, 1H), 7.79 (s, 2H), 8.40 (s, 1H), 12.85 (br s, 1H).

Step 3

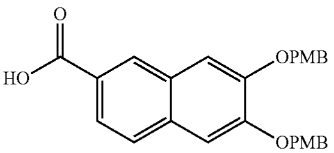

8-3

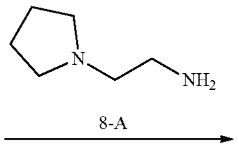

8-A

-continued

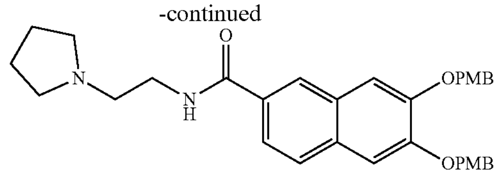

8-4

A solution of compound 8-3 (100 mg, 0.23 mmol) in THE (3 mL) was cooled in an ice water bath, and under argon atmosphere, MsCl (53 mg, 0.46 mmol) and $Et_3N$ (70 mg, 0.69 mmol) were added. The mixture was stirred at this temperature. A solution of compound 8-A (40 mg, 0.35 mmol) in THE (1 mL) was added to the above mixture, and the resulting mixture was heated to room temperature and stirred. The reaction mixture was added with water and extracted with EA. The organic phase was washed with water and saturated brine sequentially, dried over anhydrous sodium sulfate, filtered and evaporated to dryness to give a crude product. The crude product was purified by flash silica gel column chromatography to give compound 8-4 (70 mg, yield 57%).

LC/MS (ESI): m/z 541.1 [M+H]+

Step 4

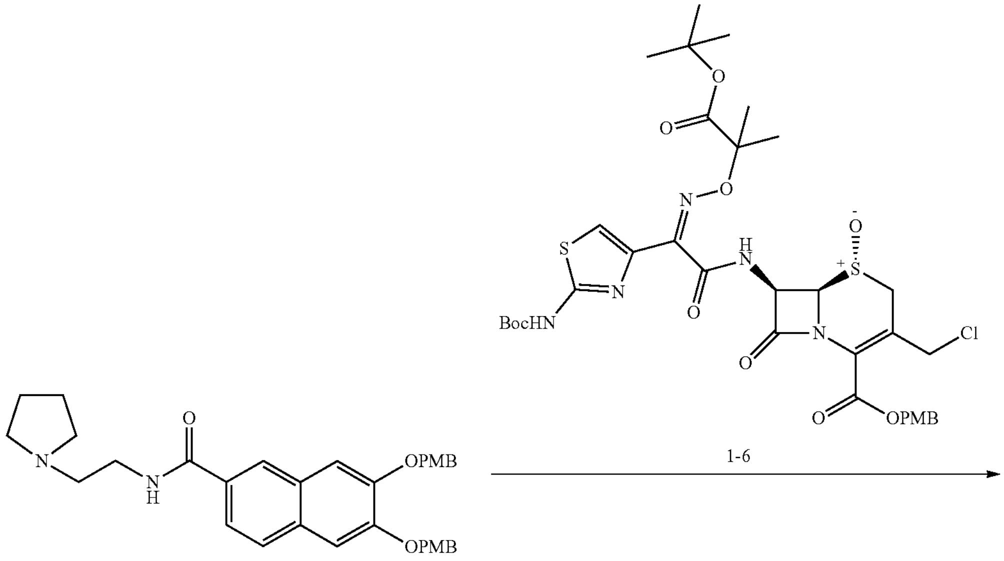

8-4

1-6

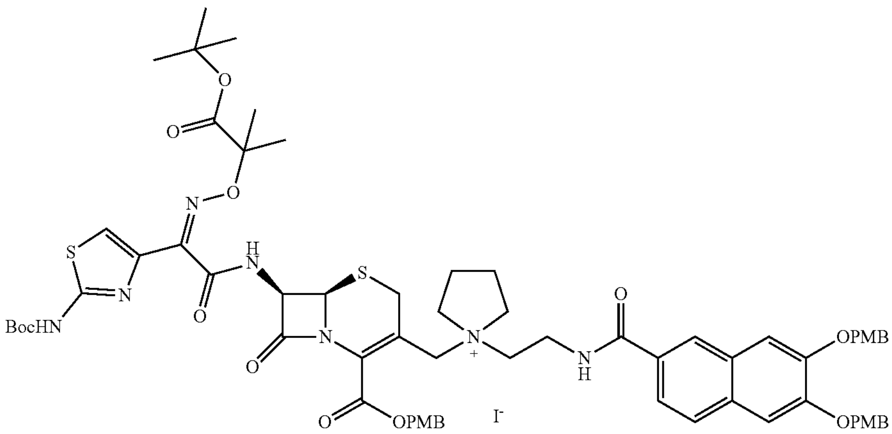

8-5

Compound 8-4 (86 mg, 0.16 mmol), compound 1-6 (139 mg, 0.18 mmol) and sodium iodide (81 mg, 0.54 mmol) were added to N,N-dimethylformamide (0.5 mL), and the mixture was stirred. After the reaction was completed, the flask was cooled in an ice water bath, followed by the addition of $PBr_3$ (72 mg, 0.26 mmol), and the mixture was stirred. After the reaction was completed, the reaction mixture was added dropwise to aqueous $NaHSO_3$ solution and filtered, and the filter cake was washed with clear water and dried in vacuum to give crude compound 8-5 (150 mg).

LC/MS (ESI): m/z 1284.1 $[M]^+$

Step 5

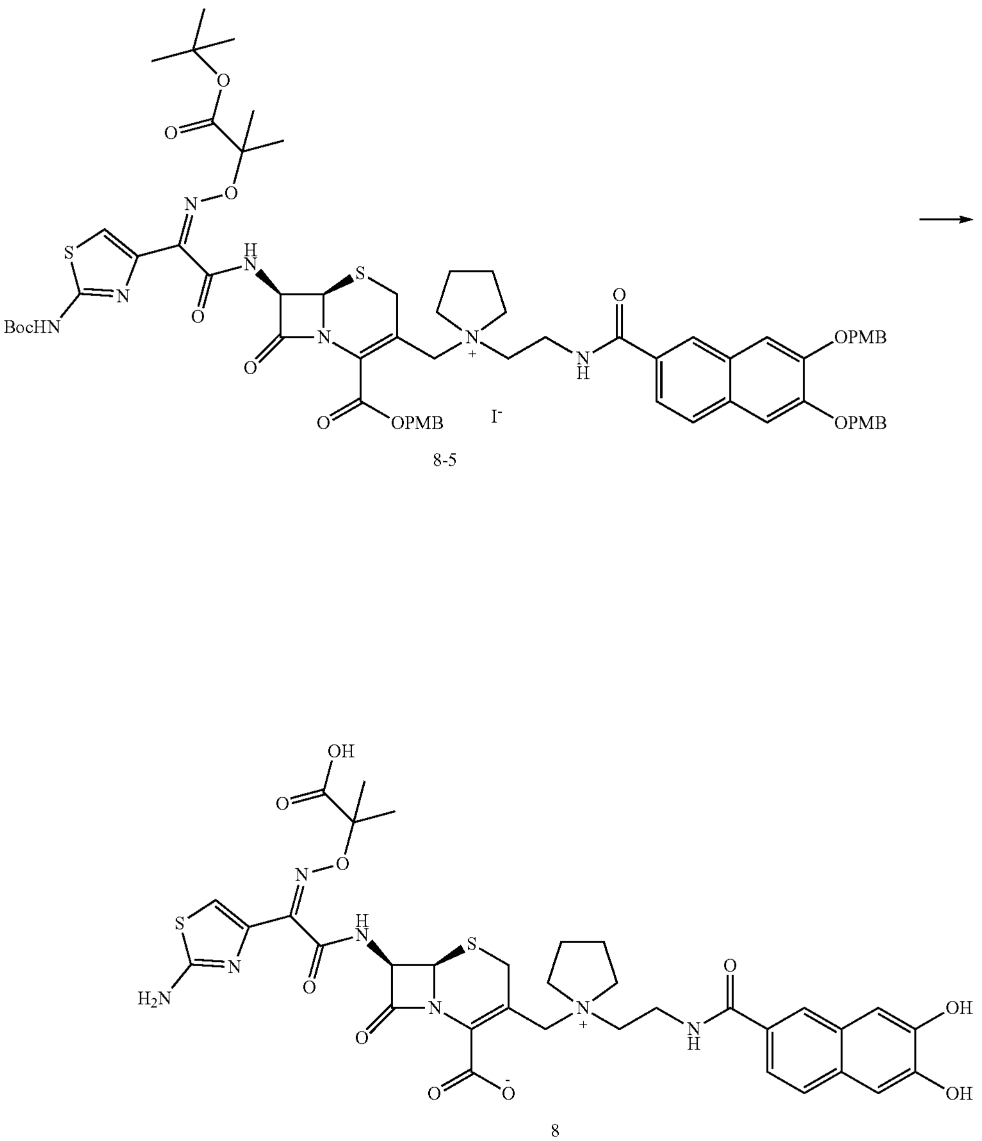

8-5

8

Compound 8-5 (150 mg, 0.117 mmol) was added to a single-necked flask, followed by the addition of anisole (0.3 mL) and TFA (1.2 mL), and the mixture was stirred. The reaction mixture was added with MTBE and filtered to give a crude product (78 mg). The crude product was purified by HPLC to give compound 8 (11.21 mg).

HRMS: 768.2109 $[M+H]^+$

Example 9

9

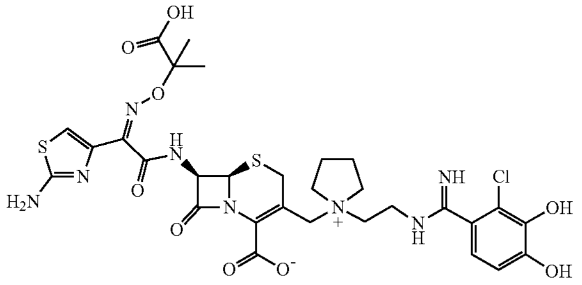

Step 1

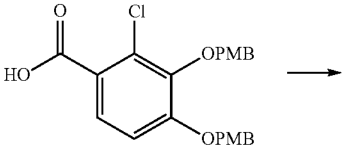

2-4

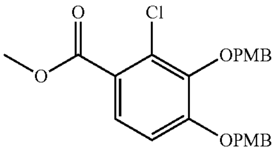

9-2

To a solution of compound 2-4 (500 mg, 1.17 mmol) in DMF (12 mL) was added iodomethane (5 g, 35.1 mmol) and potassium carbonate (323 mg, 2.34 mmol), and the mixture was stirred at room temperature. After the reaction was completed, the reaction mixture was added with water, extracted with ethyl acetate, dried over anhydrous sodium sulfate, filtered and evaporated to dryness to give a crude product. The crude product was purified by flash silica gel column chromatography to give compound 9-2 (505 mg, yield 97%).

LC/MS (ESI): m/z 465.0 $[M+Na]^+$

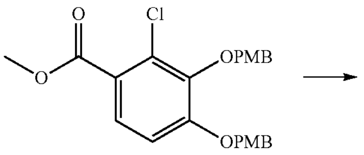

9-2

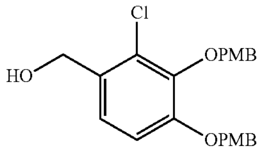

9-3

A solution of $LiAlH_4$ (1.1 mL, 1.14 mmol) in 1 M THF was added dropwise to a solution of compound 9-2 (505 mg, 1.14 mmol) in THF (4.2 mL) cooled in ice water. The mixture was slowly heated to room temperature and reacted until the reaction was completed. The reaction mixture was cooled in an ice water bath, added with $Na_2SO_4 \cdot 10\ H_2O$, stirred at room temperature and filtered to remove a solid, and the filtrated was concentrated under reduced pressure to give crude compound 9-3. The crude product was directly used in the next step (465 mg, yield 98%).

LC/MS (ESI): m/z 437.1 $[M+Na]^+$

Step 3

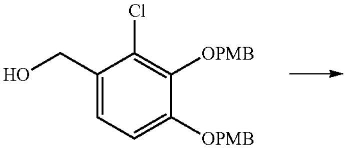

9-3

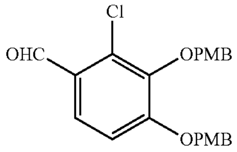

9-4

Dess-Martin reagent (712 mg, 1.68 mmol) was added to a solution of compound 9-3 (465 mg, 1.12 mmol) in DCM (23 mL) cooled in an ice/water. The mixture was slowly heated to room temperature and reacted until the reaction was completed. $H_2O$ was added to quench the reaction, and the reaction mixture was extracted with DCM. The organic phase was washed with water and saturated brine sequentially, dried over anhydrous sodium sulfate, filtered and evaporated to dryness to give a crude product. The crude product was purified by flash silica gel column chromatography to give compound 9-4 (440 mg, yield 95%).

LC/MS (ESI): m/z 412.9 $[M+H]^+$

Step 4

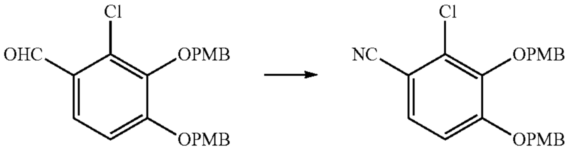

9-4 9-5

A solution of a mixture of $NH_2OH$ HCl (82 mg, 1.18 mmol) and $Et_3N$ (199 mg, 197 mmol) in $CH_3CN$ (5 mL) was stirred at room temperature, followed by the dropwise addition of a solution of compound 9-4 (405 mg, 0.98 mmol) in $CH_3CN$ (5 mL), and the resulting mixture was stirred at room temperature. To the reaction mixture were added MsCl (280 mg, 2.45 mmol) and $Et_3N$ (104 mg, 1.03 mmol). The mixture was stirred at room temperature until the reaction was completed. $H_2O$ was added to quench the reaction, and the reaction mixture was washed with saturated brine sequentially, dried over anhydrous sodium sulfate, filtered and evaporated to dryness to give a crude product. The crude product was purified by flash silica gel column chromatography to give compound 9-5 (290 mg, yield 72%).

LC/MS (ESI): m/z 432.0 $[M+Na]^+$

Step 5

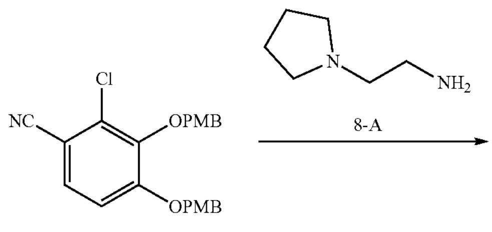

9-5

-continued

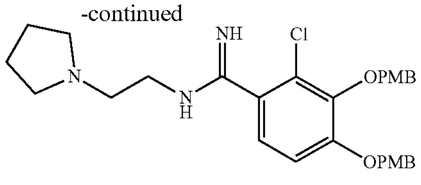

9-6 n-BuLi (0.64 mL, 1.02 mmol) was slowly added dropwise to a solution of compound 9-5 (210 mg, 0.51 mmol) in THE (5 mL) cooled in ice water. A solution of compound 8-A (88 mg, 0.77 mmol) in THE (1 mL) was added to the above mixture, and the resulting mixture was heated to room temperature and stirred. After the reaction was completed, saturated $NH_4Cl$ solution was added to quench the reaction, and the reaction mixture was extracted with EA. The organic phase was washed with water and saturated brine sequentially, dried over anhydrous sodium sulfate, filtered and evaporated to dryness to give a crude product. The crude product was purified by flash silica gel column chromatography to give compound 9-6 (147 mg, yield 54%).

LC/MS (ESI): m/z 524.2 $[M+H]^+$

Step 6

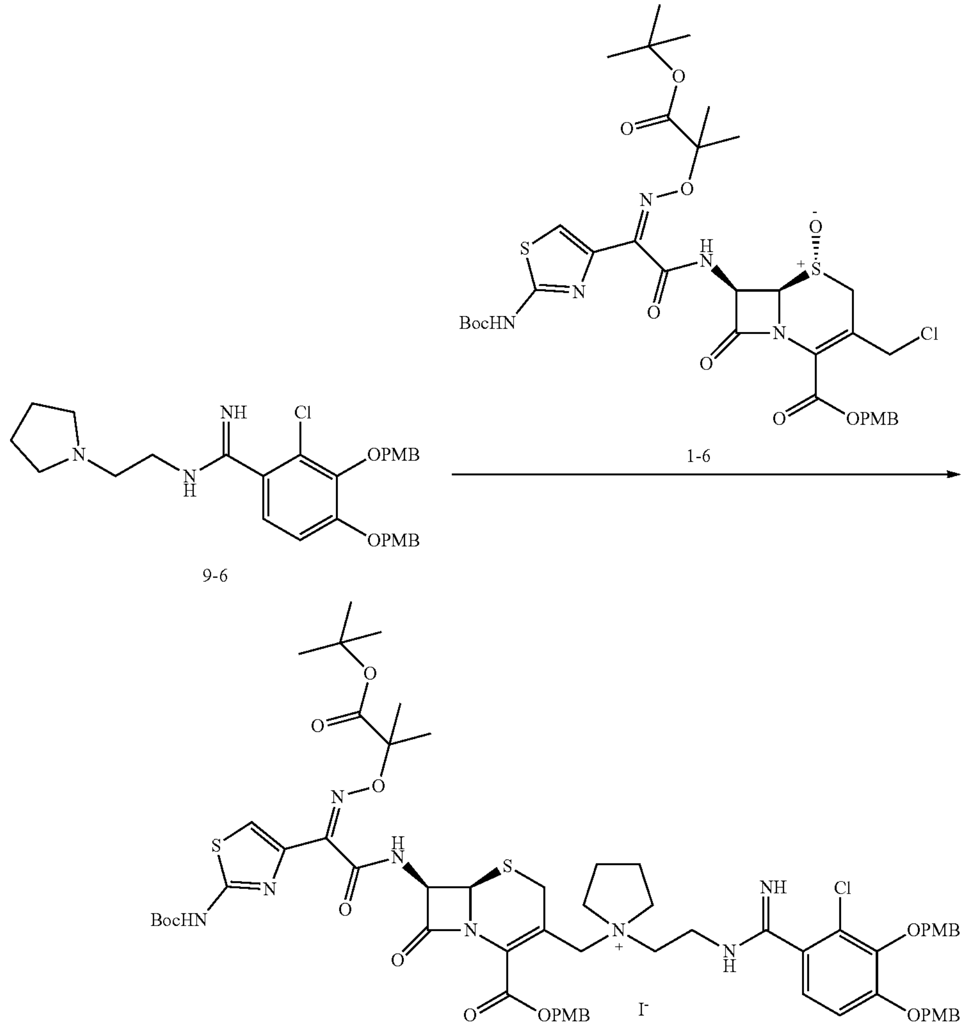

9-7

Compound 9-6 (140 mg, 0.267 mmol), compound 1-6 (265 mg, 0.334 mmol) and sodium iodide (150 mg, 1 mmol) were added to N,N-dimethylformamide (0.8 mL), and the mixture was stirred. After the reaction was completed, the flask was cooled in an ice water bath, followed by the addition of $PBr_3$ (144 mg, 0.52 mmol), and the mixture was stirred. After the reaction was completed, the reaction mixture was added dropwise to aqueous $NaHSO_3$ solution and filtered, and the filter cake was washed with clear water and dried in vacuum to obtain crude compound 9-7 (400 mg).

LC/MS (ESI): m/z 1267.1 $[M]^+$

Step 7

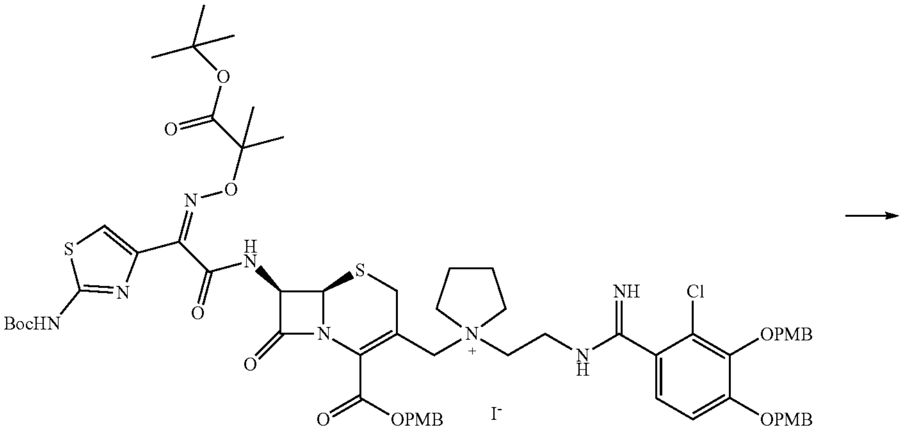

9-7

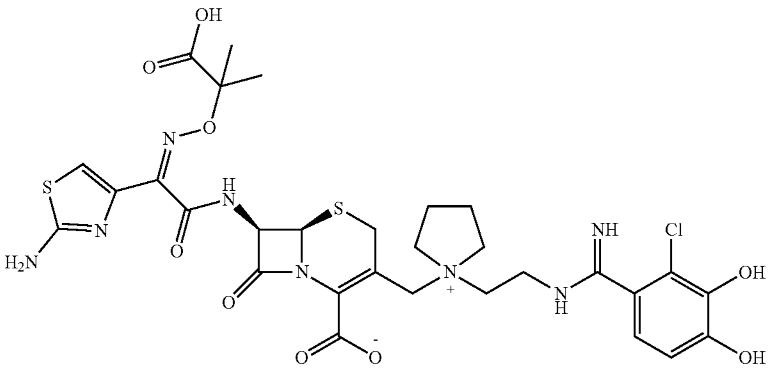

9

Compound 9-7 (100 mg, 0.0788 mmol) was added to a single-necked flask, followed by the addition of anisole (0.3 mL) and TFA (1.2 mL), and the mixture was reacted at room temperature. After the reaction was completed, the reaction mixture was added with MTBE and filtered, and the crude product was purified by HPLC to give compound 9 (4.4 mg).

HRMS: 751.1716 $[M+H]^+$

Example 10

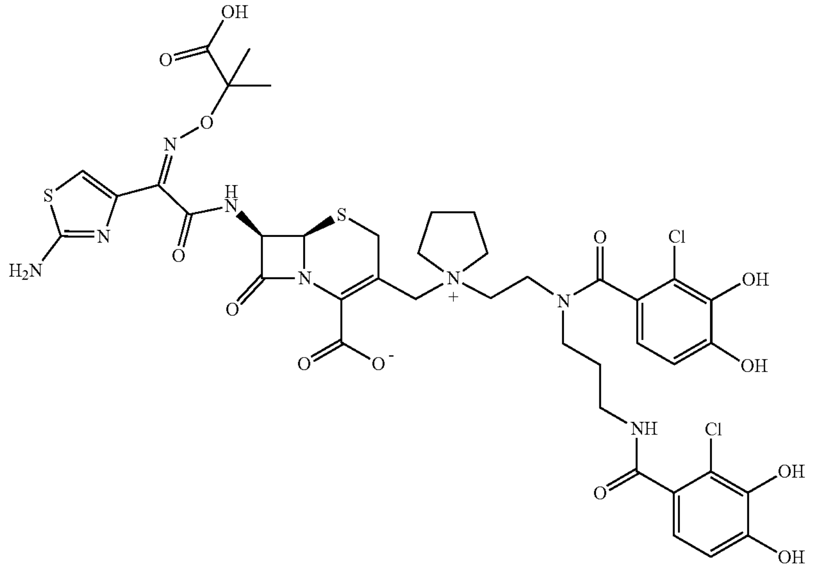

Step 1

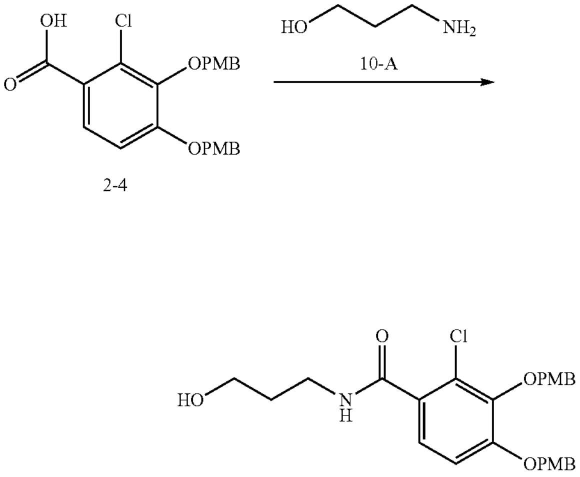

2-4

10-A 10-2

To a solution of compound 2-4 (1.5 g, 3.50 mmol) in DMF (35 mL) was added DMTMM (1.55 g, 5.26 mmol) and DIEA (905 mg, 7.0 mmol). After purging with argon three times, compound 10-A (525 mg, 7.0 mmol) was added to the above mixture, and the resulting mixture was stirred at room temperature for 2 h. The reaction solution was slowly added to water, and a solid product was gradually precipitated. The solid product obtained by filtration was dissolved in DCM, and extracted, followed by liquid separation. The organic phase was washed with water and saturated brine sequentially, dried over anhydrous sodium sulfate, filtered and evaporated to dryness to give compound 10-2 (1.6 g, yield 94%).

LC/MS (ESI): m/z 486.1 $[M+H]^+$

Step 2

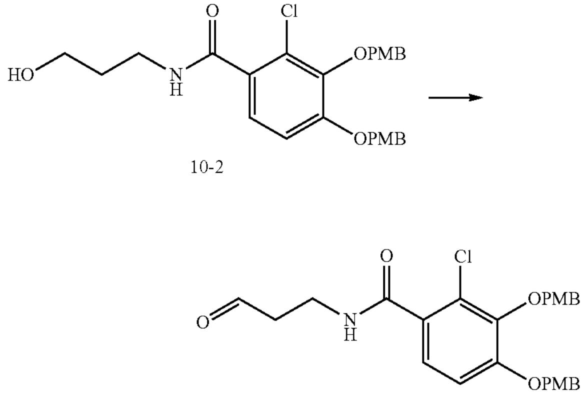

10-2

10-3

A solution of oxalyl chloride (1.05 g, 8.24 mmol) in DCM (10 mL) was cooled to −78 °C in a dry ice/acetone bath, DMSO (1.29 g, 16.5 mmol) was added dropwise under argon atmosphere, and the mixture was stirred. A solution of compound 10-2 (1.6 g, 3.30 mmol) in DCM (6 mL) was added dropwise slowly to the above mixture, and the resulting mixture was stirred at −78 °C. The reaction mixture was added with $Et_3N$ (3.34 g, 33.0 mmol), stirred at −78 °C, and slowly heated to 0 °C until the reaction was completed. $H_2O$ was added to quench the reaction, and the reaction mixture was extracted with DCM. The organic phase was washed with water and saturated brine sequentially, dried over anhydrous sodium sulfate, filtered and evaporated to dryness to give a crude product. The crude product was purified by flash silica gel column chromatography to give compound 10-3 (1.28 g, yield 80%).

LC/MS (ESI): m/z 484.0 $[M+H]^+$

Step 3

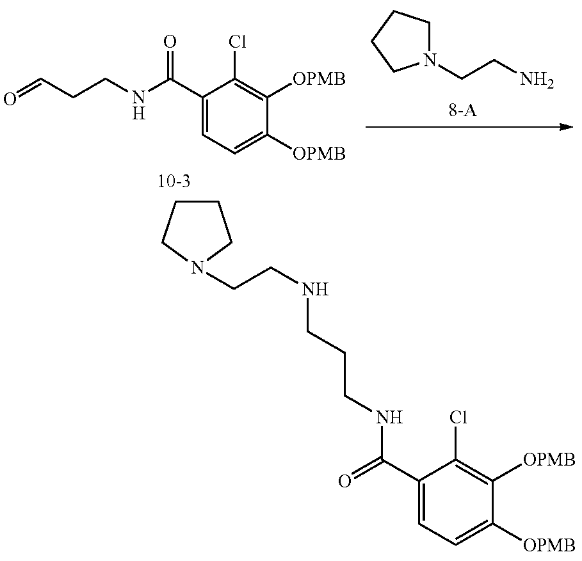

10-3
10-4

To a solution of compound 10-3 (1.28 g, 2.65 mmol) in DCM (26 mL) was added compound 8-A (605 mg, 5.30 mmol), and the mixture was cooled in an ice water bath, added with $NaBH(OAc)_3$ (1.68 g, 7.95 mmol), and heated to room temperature and stirred. After the reaction was completed, $NaHCO_3$ solution was added to quench the reaction, and the reaction mixture was extracted with DCM. The organic phase was washed with water and saturated brine sequentially, dried over anhydrous sodium sulfate, filtered and evaporated to dryness to give a crude product. The crude product was purified by flash silica gel column chromatography to give compound 10-4 (735 mg, yield 48%).

LC/MS (ESI): m/z 582.1 $[M+H]^+$

Step 4

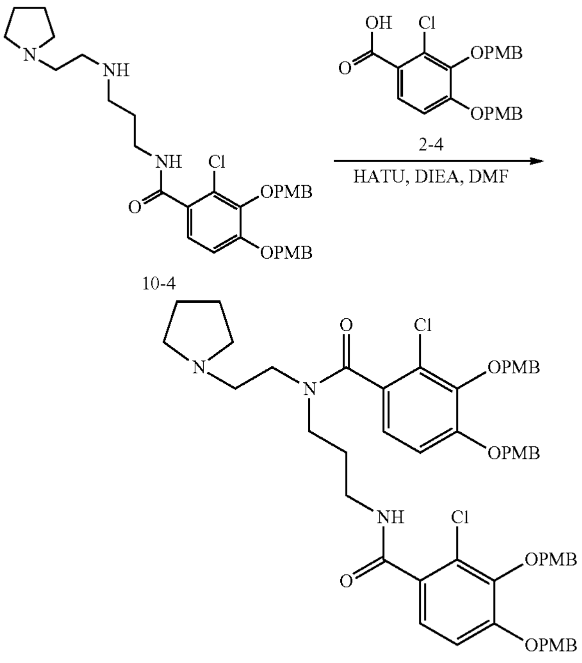

10-4
10-5

To a solution of compound 2-4 (650 mg, 1.51 mmol) in DMF (13 mL) was added HATU (961 mg, 2.52 mmol) and DIEA (490 mg, 3.78 mmol). The mixture was stirred at room temperature under argon atmosphere. Compound 10-4 (735 mg, 1.26 mmol) was added to the above reaction mixture, and the resulting mixture was stirred at room temperature. The reaction mixture was slowly added to water, filtered and dried in vacuum to give compound 10-5 (1.2 g, yield 96%).

LC/MS (ESI): m/z 992.1 $[M+H]^+$

Step 5

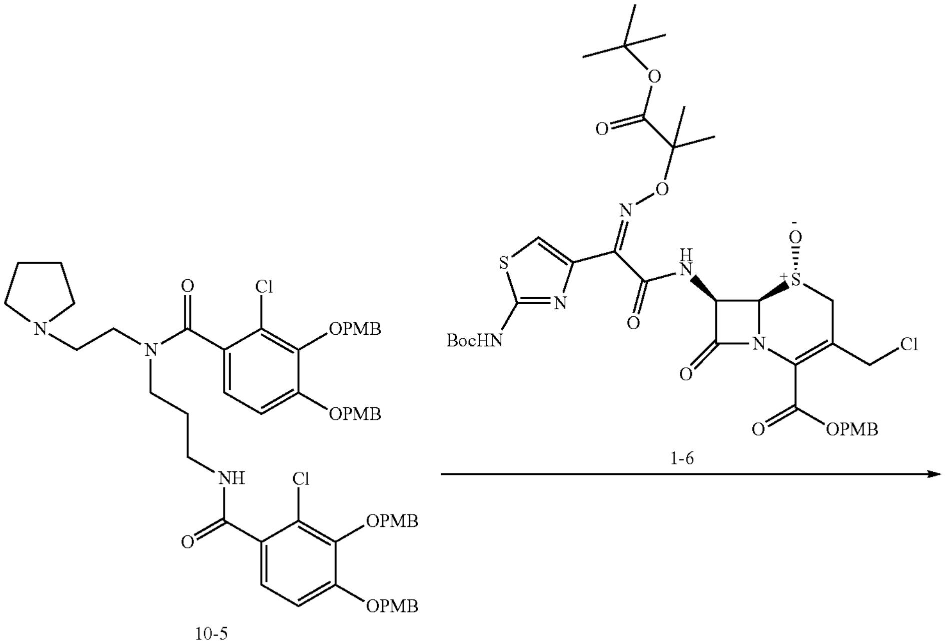
1-6
10-5

-continued

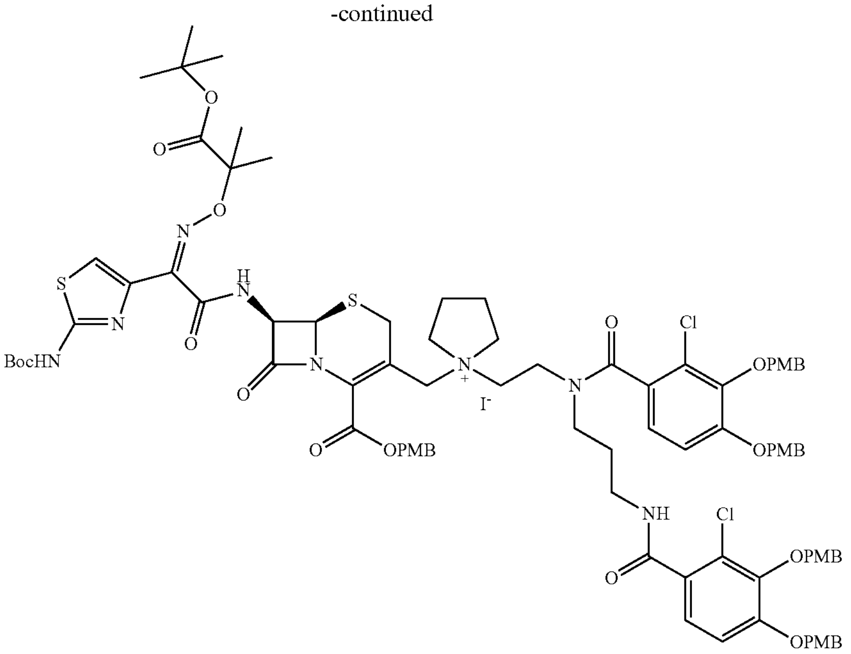

10-6

Compound 10-5 (546 mg, 0.55 mmol), compound 1-6 (398 mg, 0.5 mmol) and sodium iodide (225 mg, 1.5 mmol) were added to N,N-dimethylformamide (1.5 mL), and the mixture was stirred. After the reaction was completed, the flask was cooled in an ice water bath, followed by the addition of $PBr_3$ (360 mg, 1.33 mmol), and the mixture was stirred. After the reaction was completed, the reaction mixture was added dropwise to aqueous $NaHSO_3$ solution and filtered, and the filter cake was washed with clear water and dried in vacuum to obtain crude compound 10-6 (1.13 g).

LC/MS (ESI): m/z 1737.1 $[M]^+$

Step 6

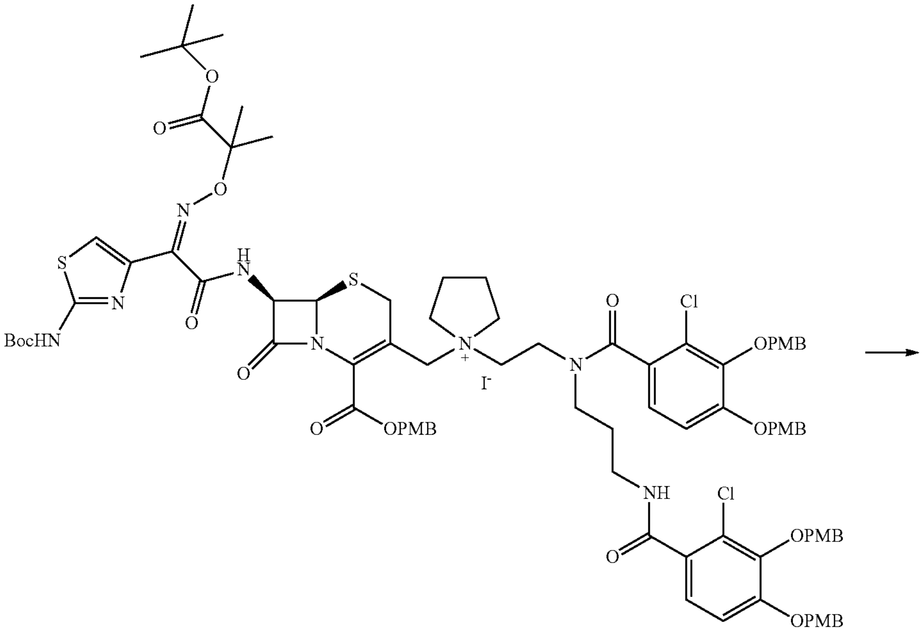

10-6

-continued

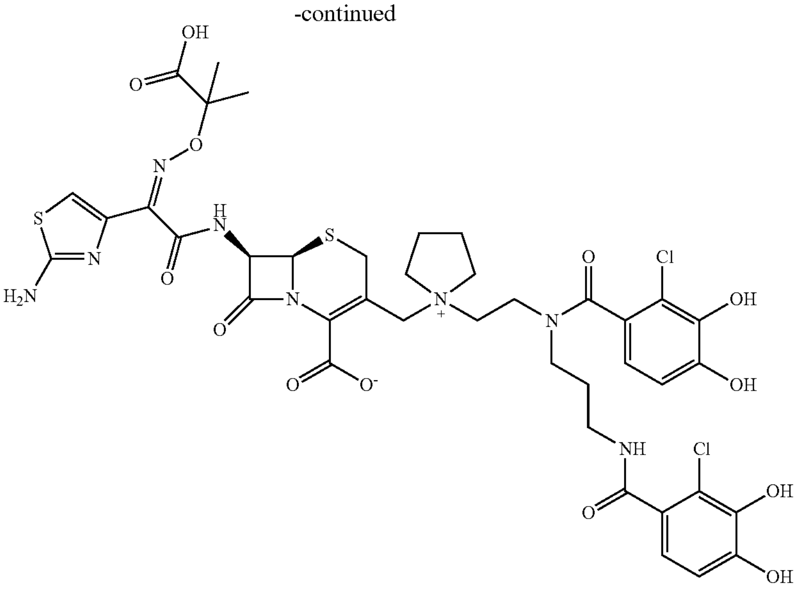

10

Compound 10-6 (1.13 g, 0.5 mmol) was added to anisole (2 mL) and trifluoroacetic acid (8 mL), and the mixture was reacted at room temperature. The reaction mixture was added with methyl tert-butyl ether, stirred and filtered. The filter cake was rinsed with MTBE and dried to give a crude product (600 mg). The crude product was purified by HPLC to give compound 10 (4 mg).

HRMS: 979.1874 $[M+H]^+$ $^1$H-NMR (400 MHz, DMSO-$d_6$) δ: 1.44 (s, 3H), 1.46 (s, 3H), 1.66-2.06 (m, 6H), 2.93-3.88 (m, 14H), 3.04-3.05 (m, 2H), 4.00-4.03 (m, 2H), 4.82-5.13 (m, 1H), 5.18 (d, 1H), 5.74 (dd, 1H), 6.54 (d, 1H), 6.60 (d, 1H), 6.73-6.85 (m, 3H), 7.28 (s, 2H), 8.05-8.33 (m, 1H), 9.46 (br s, 2H), 10.26 (br s, 2H).

Example 11

11

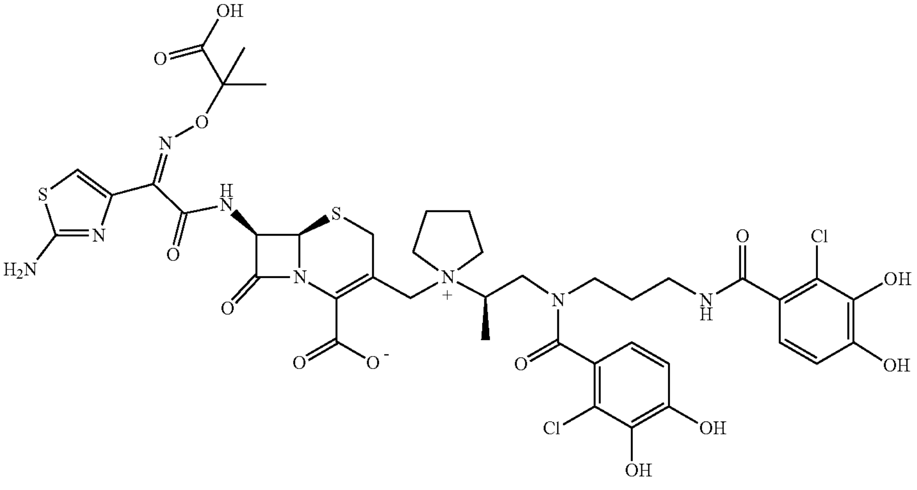

Step 1

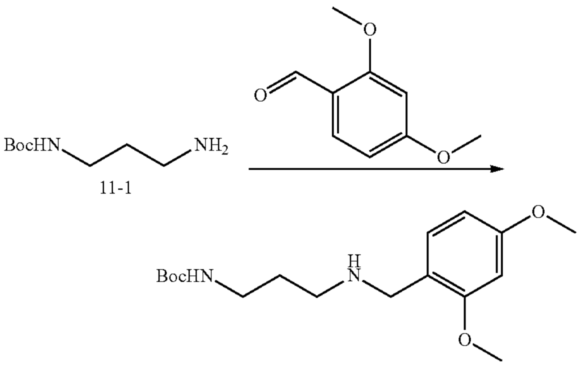

11-1

11-2

To a reaction flask were added compound 11-1 (30.3 g, 174.1 mmol, 1.0 eq), 2,4-dimethoxybenzaldehyde (29.5 g, 177.6 mmol, 1.02 eq), methanol (300 mL) and anhydrous sodium sulfate (24.7 g, 174.1 mmol, 1.0 eq), and the mixture was stirred at room temperature. The reaction mixture was cooled in an ice water bath, added with sodium borohydride (3.3 g, 87.0 mmol, 0.5 eq.) in portions, stirred for 5 min, and then stirred at room temperature until the reaction was completed. The reaction mixture was added with glacial acetic acid (3.3 mL), stirred, filtered, and washed with ethyl acetate. The filtrate was concentrated, and the residue was added with water and ethyl acetate and stirred for liquid separation. The aqueous phase was extracted with ethyl acetate. The organic phases were combined, washed with saturated brine, dried over anhydrous sodium sulfate, filtered and concentrated to give compound 11-2 (58.0 g, yield 102.8%). MS m/z 325.1 $[M+H]^+$ Step 2

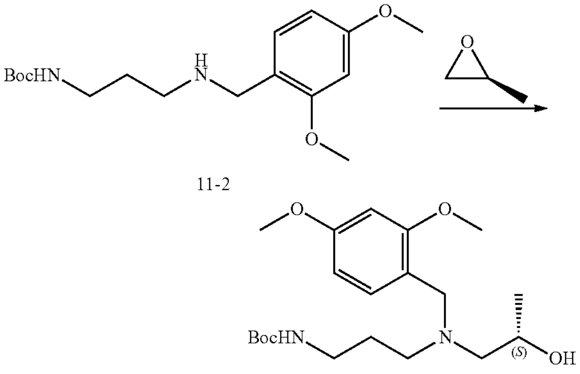

11-2

11-3

Compound 11-2 (2.0 g, 6.2 mmol, 1.0 eq), S-propylene oxide (0.54 g, 9.3 mmol, 1.5 eq) and EtOH (20 mL) were added to a reaction flask, and the mixture was heated to 60 °C After the starting material was consumed completely as detected by LC-MS, the reaction mixture was concentrated, and the crude product was purified by column chromatography to give compound 11-3 (1.2 g, yield 51.1%).

MS m/z 383.2 $[M+H]^+$

Step 3

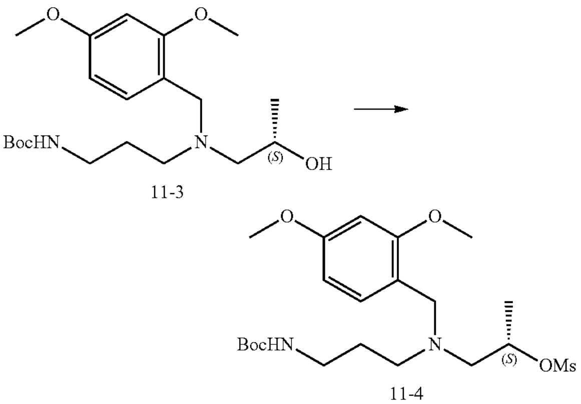

11-3

11-4

Compound 11-3 (1.2 g, 3.2 mmol, 1.0 eq), DCM (20 mL) and TEA (0.65 g, 6.4 mmol, 2.0 eq) were added to a reaction flask, and the mixture was cooled in an ice water bath, slowly added dropwise with MsCl (0.54 g, 4.7 mmol, 1.5 eq), and stirred. After the starting material was consumed completely as detected by LC-MS, the reaction mixture was washed with water and saturated sodium chloride solution, dried over anhydrous sodium sulfate, and concentrated to give crude compound 11-4 (1.34 g), which was directly used in the next reaction.

MS m/z 461.1 $[M+H]^+$

Step 4

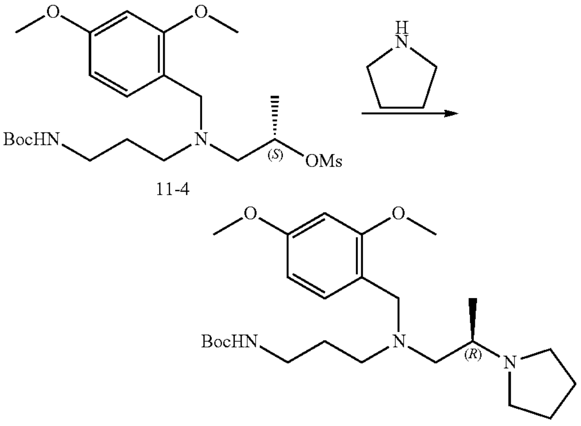

11-4

11-5

The crude compound 11-4 (1.34 g, 3.2 mmol, 1.0 eq), tetrahydropyrrole (0.56 g, 8.0 mmol, 2.5 eq), MeCN (15 mL) and potassium carbonate (0.66 g, 4.8 mmol, 1.5 eq) were added to a reaction flask, and the mixture was heated to 40 °C and stirred. After the starting material was consumed completely as detected by LC-MS, the reaction mixture was added with water (30 mL) and EA (30 mL) and stirred for liquid separation. The aqueous phase was washed with EA. The organic phases were combined, washed with saturated sodium chloride solution, dried over anhydrous sodium sulfate and concentrated. The crude product was purified by column chromatography to give compound 11-5 (0.66 g, yield 48.5% over two steps).

MS m/z 436.1 $[M+H]^+$

Step 5

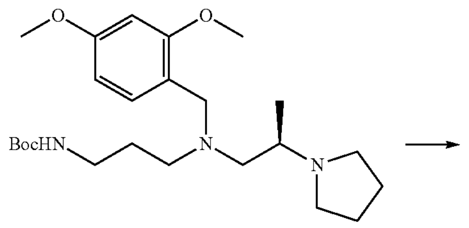

11-5

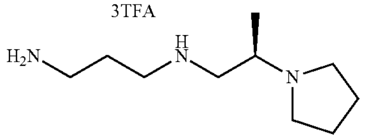

11-6

Compound 11-5 (600 mg, 1.38 mmol) and TFA (10 mL) were dissolved in a reaction flask, and the solution was heated to 60 °C and reacted until the reaction was completed. The reaction mixture was concentrated to dryness, added with MTBE (10 mL) and slurried, and the supernatant was removed. The resulting oil was concentrated in vacuum to remove most of the solvent, and directly used in the next step.

MS m/z 186.1 $[M+H]^+$

Step 6

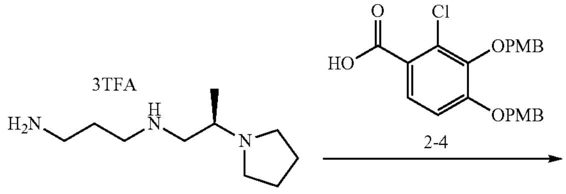

11-6 2-4

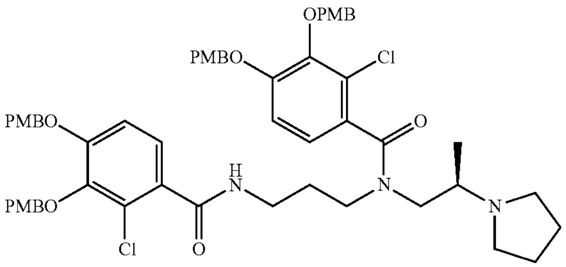

11-7

The crude compound 11-6 and compound 2-4 (1.31 g, 3.05 mmol) were dissolved in DCM (15 mL), and the mixture was stirred at 0 °C DIPEA (2.02 mL, 12.22 mmol) and HATU (1.39 g, 3.67 mmol) were added. The resulting mixture was warmed to room temperature and reacted until the reaction was completed. The reaction mixture was added with water (10 mL), followed by the liquid separation. The organic phase was washed with water, dried over anhydrous sodium sulfate, filtered, and concentrated to dryness. The crude product was separated by column chromatography (DCM:MeOH=10:1) to give compound 11-7 (0.85 g).

MS m/z 1006.3 $[M+H]^+$

Step 7

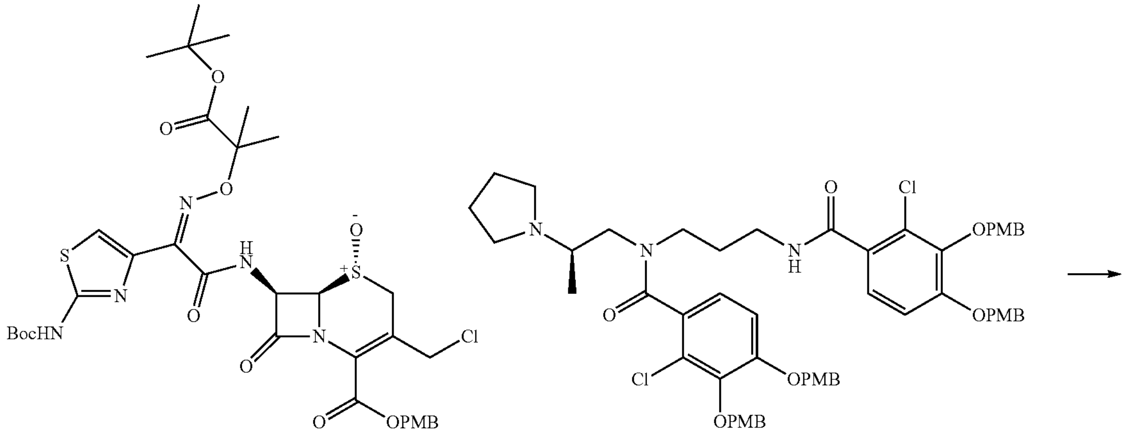

1-6 11-7

-continued

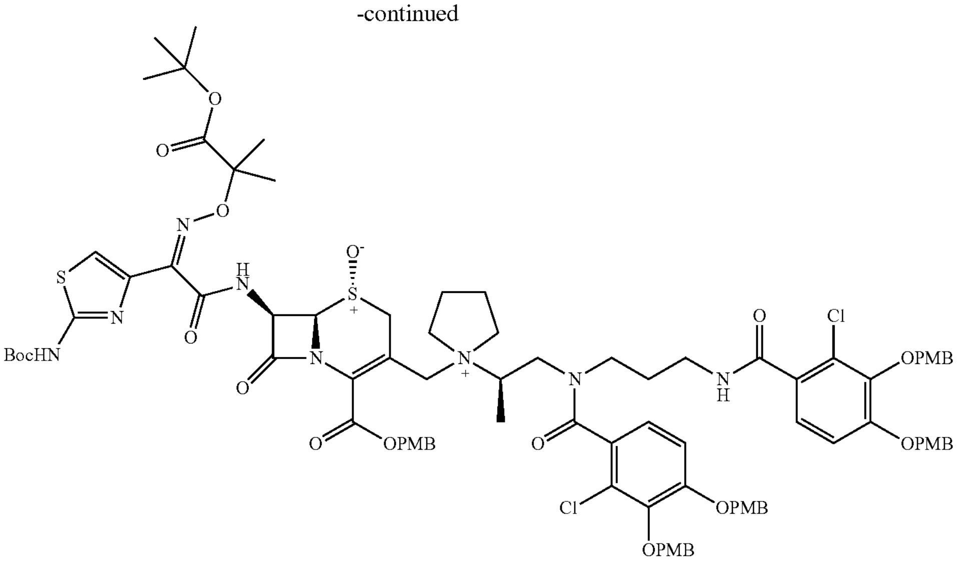

11-8

Compound 1-6 (720 mg, 0.904 mmol), compound 11-7 (650 mg, 0.645 mmol), sodium iodide (0.406 g, 2.71 mmol) and boric acid (17 mg, 0.271 mmol) were added to a reaction flask, and after purging with argon three times, NMP (2.1 mL) was added. The reaction mixture was reacted at room temperature until the reaction was completed. The reaction solution was directly used in the next step without further treatment.

MS m/z 1767.5 $[M]^+$

Step 8

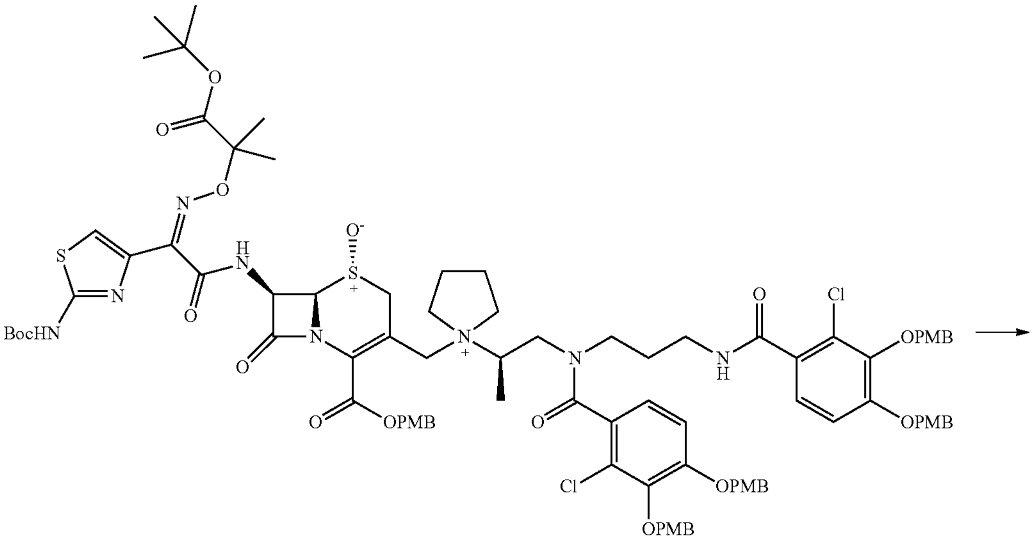

11-8

-continued

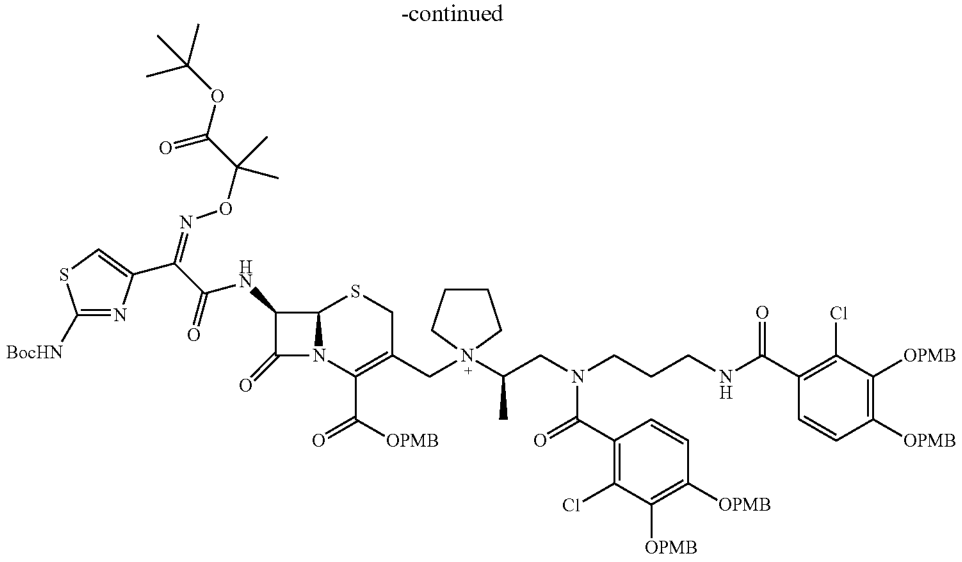

11-9

NMP (0.7 mL) was added to the above reaction mixture, and the resulting reaction mixture was cooled to 0 °C, added with phosphorus trichloride (0.103 mL, 1.17 mmol), and reacted at 0 °C until the reaction was completed. The reaction mixture was added with 5% aqueous sodium hydrogen sulfite solution (20 mL), slurried in an ice water bath and filtered, and the filter cake was dissolved with DCM (20 mL), dried over anhydrous sodium sulfate, filtered, and concentrated to dryness to give compound 11-9 (1.21 g).

MS m/z 1751.4 $[M]^+$

Step 9

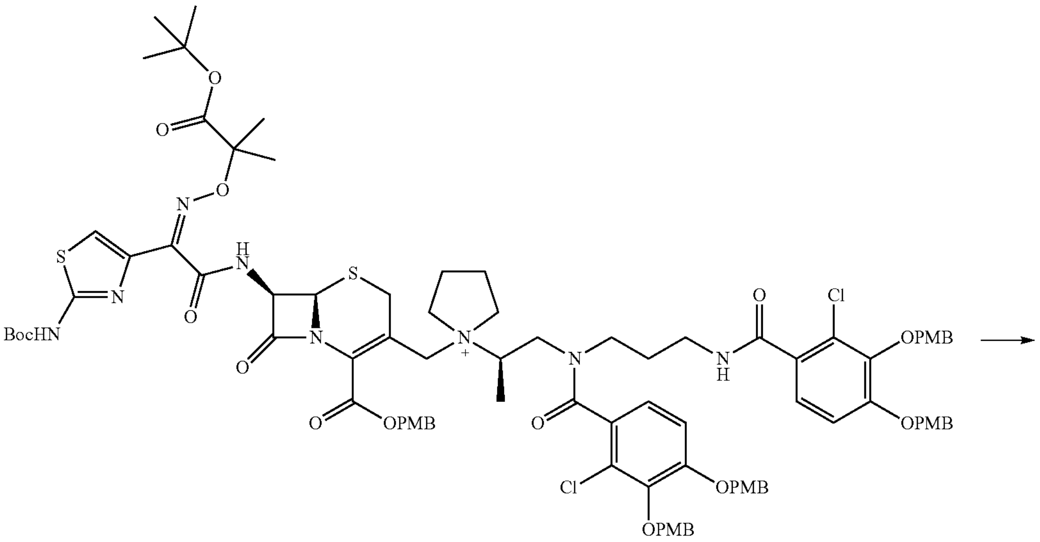

11-9

-continued

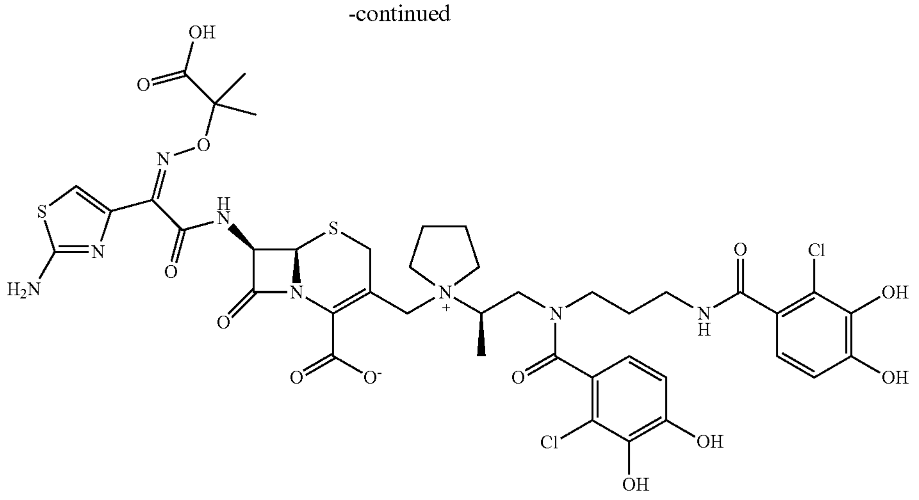

11

Compound 11-9 (1.21 g, 0.69 mmol) was dissolved in anisole (0.2 mL) and trifluoroacetic acid (0.8 mL), and the solution was reacted at room temperature until the reaction was completed. The reaction mixture was cooled to 0 °C, added with MTBE (20 mL), slurried in an ice water bath and filtered, the filter cake was rinsed with MTBE and dried to give a crude product (0.82 g). The crude product was purified by reverse HPLC to give compound 11 (107 mg).

MS m/z 993.1 $[M+H]^+$

Biological Evaluation

The present disclosure is further described and explained below with reference to test examples, which are not intended to limit the scope of the present disclosure.

Test Example 1: Antibacterial Activity Test

The test compounds were diluted in a gradient and used for an MIC assay on the test strains. The test compounds at an initial assay concentration of 32 μg/mL were diluted in a 2-fold gradient (11 concentration points in total), and two duplicate wells were set for each concentration. Additional wells without drug dosing were set as growth controls. The minimum inhibitory concentration (MIC) assay was performed with reference to the Clinical and Laboratory Standards Institute (CLSI) guidelines.

1. Preparation of Bacterial Inoculation Liquid

After the frozen strains were subcultured, a single colony was picked and re-suspended in normal saline or sterile water in a tube. The bacterial suspension was vortexed and adjusted to 0.5 McF using a spectrophotometer at the wavelength of 530 nm. The bacterial solution was taken by a pipette, added to a culture medium, diluted and mixed well, and seeded to a bacterial assay plate.

2. Culture

The bacterial assay plate was placed in an incubator, incubated at 35 °C with 85% humidity for 24 h, and read for the MIC values.

3. MIC interpretation

The 96-well plate was affixed with a disposable sealing film, shaken and mixed well, and visually observed using a plate reader. The minimum concentration of the compounds capable of inhibiting the growth of bacteria was defined as MIC as compared to the growth controls.

MIC Results

| Strain | Strain No. | MIC (μg/mL) | | | | | | |
|---|---|---|---|---|---|---|---|---|
| | | Meropenem | Cefiderocol | Compound 1 | Compound 2 | Compound 3 | Compound 4 | Compound 6 |
| Carbapenem- | 110390 | 12 | 0.5 | >32 | 0.5 | 2 | >32 | 2 |
| resistant | 110358 | 4 | 1 | >32 | 1 | 2 | >32 | 4 |
| *Pseudomonas* | 110163 | 24 | 1 | >32 | 0.5 | 1 | >32 | 0.5 |
| *aeruginosa* | 110224 | 16 | 0.75 | 32 | 0.75 | 1 | >32 | 0.625 |
| (CRPA) (n = 5) | 100110 | 32 | 0.047 | 16 | 0.031 | 0.5625 | 16 | 0.063 |
| Carbapenem- | 311277 | 32 | 5 | >32 | 1.5 | 8 | >32 | 8 |
| resistant | 110525 | 32 | 6 | >32 | 2 | 16 | >32 | 4 |
| *Enterobacteriaceae* | 110502 | 32 | 12 | >32 | 6 | >32 | >32 | 32 |
| (CRE) (n = 5) | 100186 | >32 | 0.5 | >32 | 1.5 | 6 | >32 | 1.5 |
| | 100109 | >32 | 1 | >32 | 1 | 3 | >32 | 2 |
| Carbapenem- | 110517 | 32 | 0.5 | >32 | 0.5 | 1 | >32 | 1 |
| resistant | 110477 | >32 | 1 | >32 | 2 | 4 | >32 | 3 |
| *Acinetobacter* | 110440 | 32 | 1.5 | >32 | 3 | 4 | >32 | 4 |
| *baumannii* | 100333 | >32 | 2 | >32 | 2 | 6 | >32 | 6 |
| (CRAB) (n = 5) | 100085 | 32 | 0.5 | >32 | 0.5 | 3 | >32 | 3 |

As shown above, the compounds of the present disclosure have a broad antibacterial spectrum, specifically an effective antibacterial spectrum against gram-negative bacteria, and/or have efficacy against multidrug-resistant bacteria, and further exhibit high stability in its activity against gram-negative bacteria producing β-lactamases.

Test Example 2: Antibacterial Activity Test

1. The test compounds were dissolved in sterile normal saline, vortexed for uniformly mixing, and diluted in a 2-fold dilution with the sterile normal saline (11 concentration points in total). The test concentration range was 32-0.031 μg/mL, and two duplicate wells were set for each concentration. Additional wells without drug dosing were set as growth controls.
2. 4 μL of the diluent was added to 196 μL of the bacterial suspension in a 96-well plate (the bacterial count in the bacterial suspension was 2-8×$10^5$ colony forming units/mL).
3. The plate was incubated at 36 °C for 24 h, and read for the MIC values by visual observation.

The minimum inhibitory concentration (MIC) assay was performed with reference to the Clinical and Laboratory Standards Institute (CLSI) guidelines.

| Strain (gram-negative bacteria) | Strain ID | AMR gene | ID-CAMHB, MIC, μg/mL Cefiderocol | Compound 2 | Compound 7 | Compound 5 |
|---|---|---|---|---|---|---|
| Carbapenem-resistant *Acinetobacter baumannii* (CRAB, *Acinetobacter baumannii*) | FDA-CDC AR-BANK #0036 | strB, OXA-65, OXA-24, strA, sul2 | 0.25 | 0.5 | 2 | >32 |
| | FDA-CDC AR-BANK #0052 | OXA-58, OXA-100, sul2 | 0.0625 | 0.0625 | 0.25 | >32 |
| | FDA-CDC AR-BANK #0063 | OXA-23, OXA-65, OXA-24, sul2 | 8 | 16 | >32 | >32 |
| | FDA-CDC AR-BANK #0070 | OXA-58, OXA-100, sul2 | 0.125 | 0.0625 | 0.125 | >32 |
| | FDA-CDC AR-BANK #0101 | strB, OXA-65, OXA-24, strA, sul2 | 1 | 0.5 | 4 | >32 |
| Carbapenem-resistant *Enterobacteriaceae* (CRE, *Klebsiella pneumoniae*) | FDA-CDC AR-BANK #0361 | TEM-1; SHV-12; KPC-2 | 2 | 1 | 1 | >32 |
| | FDA-CDC AR-BANK #0362 | TEM-1; SHV-11; KPC-2 | 0.5 | 0.5 | 1 | >32 |
| | FDA-CDC AR-BANK #0363 | TEM-1; SHV-12; KPC-2 | 0.25 | 0.5 | 0.5 | >32 |
| | FDA-CDC AR-BANK #0438 | aph(3')-Ia, dfrA12, KPC-3, OmpK35, oqxA, oqxB, SHV-11 | 2 | 1 | 2 | >32 |
| | FDA-CDC AR-BANK #0453 | KPC-3, OmpK35, oqxA, oqxB, SHV-11, TEM-1B | 1 | 2 | 4 | >32 |
| Carbapenem-resistant *Pseudomonas aeruginosa* (CRPA, *Pseudomonas aeruginosa*) | FDA-CDC AR-BANK #0439 | aac(6')-Il, aadA1b, BCR1, IMP-18, OXA-50 | 0.25 | 0.5 | 8 | >32 |
| | FDA-CDC AR-BANK #0441 | KPC-2 | 1 | 2 | 8 | >32 |
| | FDA-CDC AR-BANK #0444 | aac(6')-Il, dfrB5, OXA-4, tet(G), VIM-2 | 2 | 4 | 32 | >32 |
| | FDA-CDC AR-BANK #0457 | aadA6, VIM-2 | 0.125 | 0.125 | 1 | >32 |
| Control strain* *Escherichia coli* | ATCC 25922 | — | 0.0625 | 0.125 | 0.125 | >32 |
| Control Strain* *Pseudomonas aeruginosa* | ATCC 27853 | — | 0.0625 | 0.0625 | 0.125 | >32 |

| Strain (gram-negative bacteria) | ID-CAMHB, MIC, μg/mL Compound 9 | Compound 8 | Compound 10 | Compound 11 | CAMHB MIC, μg/mL Meropenem |
|---|---|---|---|---|---|
| Carbapenem-resistant | >32 | 0.25 | 0.125 | 0.5 | >32 |
| *Acinetobacter baumannii* | >32 | 0.0625 | 0.0625 | 0.125 | 16 |
| (CRAB, *Acinetobacter* | >32 | 8 | >32 | 4 | >32 |
| *baumannii*) | >32 | 0.125 | 0.125 | 0.25 | 8 |
| | >32 | 2 | 0.5 | 1 | >32 |
| Carbapenem-resistant | >32 | 2 | 0.25 | 1 | 16 |
| *Enterobacteriaceae* (CRE, *Klebsiella* | 16 | 1 | 0..25 | 0.25 | >32 |
| *pneumoniae*) | >32 | 0.25 | 0.125 | 0.5 | 32 |
| | >32 | 2 | 0.5 | 1 | >32 |
| | >32 | 2 | 2 | 1 | >32 |

-continued

| | | | | | |
|---|---|---|---|---|---|
| Carbapenem-resistant *Pseudomonas aeruginosa* (CRPA, *Pseudomonas aeruginosa*) | >32 | 1 | 0.25 | 0.5 | >32 |
| | >32 | 4 | 1 | 8 | >32 |
| | >32 | 4 | 16 | 4 | >32 |
| | >32 | 0.25 | 0.0625 | 0.25 | >32 |
| Control strain* *Escherichia coli* | 16 | 0.25 | 0.0625 | 0.125 | ≤0.03125 |
| Control Strain* *Pseudomonas aeruginosa* | >32 | 0.25 | 0.0625 | 0.0625 | 0.5 |

As shown above, the compounds of the present disclosure have a broad antibacterial spectrum, specifically an effective antibacterial spectrum against gram-negative bacteria, and/or have efficacy against multidrug-resistant bacteria, and further exhibit high stability in its activity against gram-negative bacteria producing β-lactamases.

Test Example 3: Pharmacokinetic Study in Cynomolgus Monkeys

1. Sample Preparation

An appropriate amount of a test compound was weighed precisely and added to a container, and 0.9% sodium chloride injection and 0.2 M NaOH solution were added thereto in an ice bath until the test compound was completely dissolved, so that a sample solution at a concentration of 2 mg/mL was obtained followed by storage at 2-8 °C for later use.

2. Test Animal

Species and strain: cynomolgus monkey

Animal grade: general grade

Animal source: Guangxi Xiongsen Primate Experimental Animal Breeding Development Co., Ltd.

Number of the using of laboratory animal: SYXK (Su) 2019-0012

3. Test Method 6 cynomolgus monkeys (half male and half female) were selected and randomly divided into 3 groups with 1 animal/sex in each group. The cynomolgus monkeys were administered with the test sample at a dose of 10 mg/kg by the single intravenous infusion. Blood samples were collected from each group of animals at the following time points: before administration, and 5 min, 15 min, 0.5 h, 1 h, 2 h, 4 h, 6 h, and 8 h after administration. In the test, the concentration of each test compound in the plasma of the cynomolgus monkey was detected by the LC-MS/MS method, and the lower limit of quantification of the analysis methods for the plasma samples were all 1 μg/mL. The plasma concentration data were analyzed by the non-compartmental analysis (NCA) of the analysis software for pharmacokinetic data, WinNonlin, pharmacokinetic parameters were calculated, and pharmacokinetic characteristics of the test compounds in cynomolgus monkeys after administration were investigated, with the results shown in the following table

| Sample | Animal No. | $t_{1/2}$ (h) | $T_{max}$ (h) | $C_{max}$ (ug/mL) | AUC last (h*ug/mL) | $AUC_{inf}$ (h*ug/mL) | Vd (mL/kg) | CL (mL/h/kg) | MRT (h) |
|---|---|---|---|---|---|---|---|---|---|
| Compound 10 | 2073541 | 0.62 | 0.08 | 35.48 | 29.29 | 32.94 | 270.05 | 303.57 | 0.64 |
| | 2073542 | 0.56 | 0.08 | 30.64 | 23.44 | 25.64 | 313.34 | 390.01 | 0.62 |
| Cefiderocol | 2073545 | 0.86 | 0.08 | 30.53 | 26.21 | 32.39 | 380.98 | 308.70 | 0.70 |
| | 2073546 | 0.75 | 0.08 | 24.33 | 23.94 | 28.35 | 379.63 | 352.76 | 0.70 |

The compounds of the present disclosure are superior in terms of $C_{max}$ as compared to cefiderocol.

The invention claimed is:

1. A compound of formula (I-2) or a pharmaceutically acceptable salt, stereoisomer or deuterated compound thereof, (I-2)

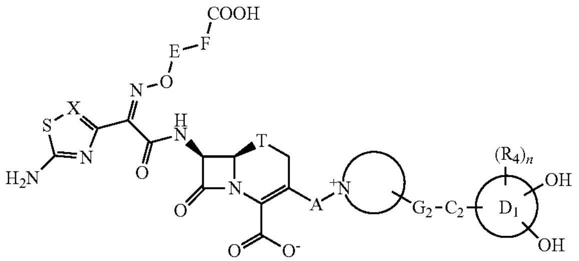

wherein,

X is selected from the group consisting of N, CH and C—Cl;

T is selected from the group consisting of S, S—O, and O;

E is selected from the group consisting of

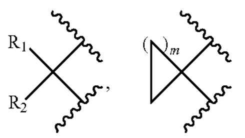 and 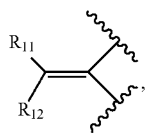

wherein $R_1$ and $R_2$ are each independently selected from the group consisting of hydrogen, halogen, phenyl, alkylthio, and alkyl optionally substituted with carbamoyl; $R_{11}$ and $R_{12}$ are each independently selected from the group consisting of hydrogen, carboxyl, and alkyl optionally substituted with carbamoyl; and m is an integer from 1 to 5;

F is a single bond;

A is selected from the group consisting of alkylene, alkenylene and alkynylene;

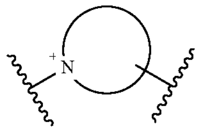

is a quaternary ammonium group containing one or more N atoms and selected from the group consisting of heterocyclyl, fused heterocyclyl, heteroaryl and fused heteroaryl, wherein the heterocyclyl, fused heterocyclyl, heteroaryl and fused heteroaryl are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy, alkylthio, cycloalkyl, heterocyclyl, aryl and heteroaryl;

$G_2$ is $G_1$ or alkylene, wherein the alkylene is optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

$G_1$ is

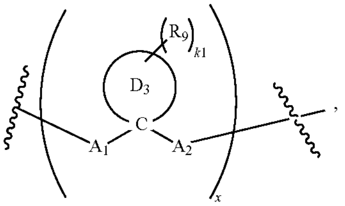

wherein each x is independently an integer from 1 to 6;

$A_1$ is selected from the group consisting of a single bond, alkylene, alkenylene and alkynylene, wherein the alkylene, alkenylene and alkynylene are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

$A_2$ is selected from the group consisting of a single bond, alkylene, alkenylene and alkynylene, wherein the alkylene, alkenylene and alkynylene are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy and alkylthio;

ring $D_3$ is selected from the group consisting of cycloalkyl, fused cycloalkyl, heterocyclyl and fused heterocyclyl;

$R_9$ is selected from the group consisting of alkyl, halogen, hydroxy, mercapto, oxo, thio, —$NR_iR_j$, —$C(O)R_k$, —$C(O)OR_k$, nitro, cyano, alkoxy and alkylthio, wherein the alkyl, alkoxy and alkylthio are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy, alkylthio, cycloalkyl, heterocyclyl, aryl and heteroaryl;

k1 is an integer from 0 to 8;

$C_2$ is $NR_{31}$-C(═O)—, wherein $R_{31}$ is selected from the group consisting of alkyl and alkoxy, wherein the alkyl and alkoxy are each independently substituted with one or more

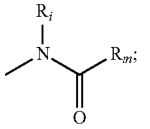

$R_m$ is selected from the group consisting of hydrogen, alkyl, hydroxy, aryl and heteroaryl, wherein the alkyl, aryl and heteroaryl are each independently optionally substituted with one or more substituents selected from the group consisting of alkyl, halogen, hydroxy, mercapto, —$NR_iR_j$, carboxyl, nitro, cyano, alkoxy, alkylthio, cycloalkyl, heterocyclyl, aryl and heteroaryl;

ring $D_1$ is selected from the group consisting of aryl, fused cycloaryl, heterocyclyl, fused heterocyclyl, heteroaryl and fused heteroaryl;

each $R_4$ is independently selected from the group consisting of alkyl, halogen, hydroxy, mercapto, oxo, thio, —$NR_iR_j$, —$C(O)R_k$, —$C(O)OR_k$, nitro, cyano, alkoxy and alkylthio, wherein the alkyl, alkoxy and alkylthio are each independently optionally substituted with one or more substituents selected from the group consisting of alkyl, halogen, hydroxy, mercapto, —$NR_iR_j$, oxo, thio, —$C(O)R_k$, —$C(O)OR_k$, —$C(S)R_k$, nitro, cyano, alkoxy, alkylthio, cycloalkyl, heterocyclyl, aryl and heteroaryl;

n is an integer from 0 to 8;

$R_i$ and $R_j$ are each independently selected from the group consisting of hydrogen, hydroxy, $C_1$-$C_6$ alkyl and $C_1$-$C_6$ alkoxy; and each $R_k$ is independently selected from the group consisting of hydrogen, alkyl, haloalkyl, alkoxy, hydroxy and —$NR_iR_j$, wherein the alkyl, haloalkyl and alkoxy are each independently optionally substituted with one or more substituents selected from the group consisting of alkyl, halogen, hydroxy, mercapto, —$NR_iR_j$, oxo, thio, carboxyl, nitro, cyano, alkoxy, alkylthio, cycloalkyl, heterocyclyl, aryl and heteroaryl.

2. The compound or the pharmaceutically acceptable salt, stereoisomer or deuterated compound thereof according to claim 1, wherein

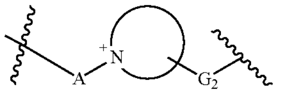

is selected from the group consisting of:

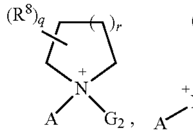 , 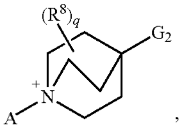 , 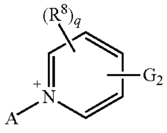 ,

-continued

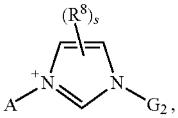

,

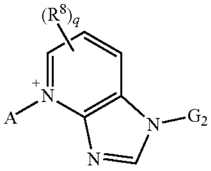

,

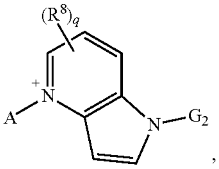

,

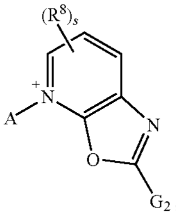

,

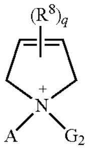

,

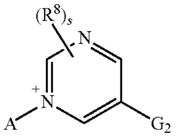

,

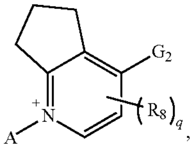

,

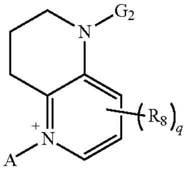

and

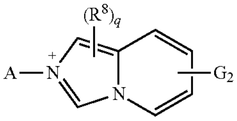

, wherein each $R_8$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy;

each q is independently an integer from 0 to 5;

each r is independently an integer from 0 to 5; and each s is independently an integer from 0 to 3.

3. The compound or the pharmaceutically acceptable salt, stereoisomer or deuterated compound thereof according to claim 1, wherein $G_2$ is selected from the group consisting of:

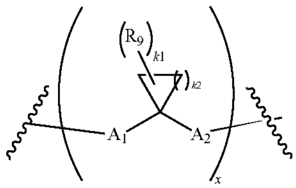

,

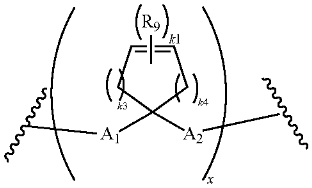

,

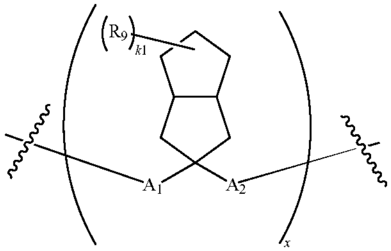

,

-continued

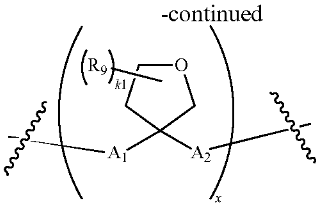

and

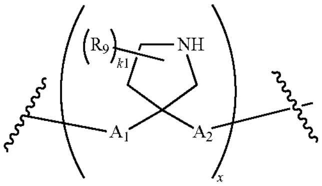

, wherein each $R_9$ is independently selected from the group consisting of halogen, hydroxy, alkyl, alkoxy, haloalkyl and haloalkoxy;

each k2 is independently an integer from 1 to 6;

each k3 is independently an integer from 0 to 3; and each k4 is independently an integer from 0 to 3.

4. The compound or the pharmaceutically acceptable salt, stereoisomer or deuterated compound thereof according to claim 1, wherein $G_2$ is selected from the group consisting of:

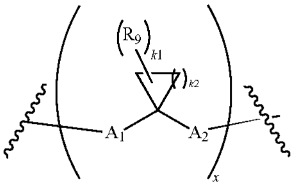

,

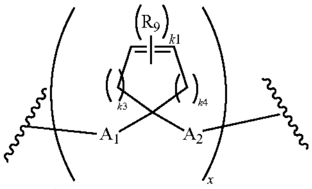

,

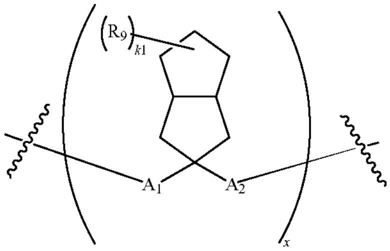

,

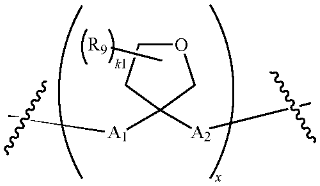

and

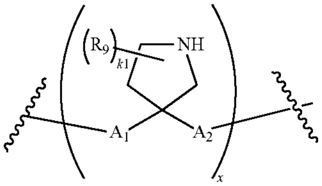

, wherein each $R_9$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy;

$A_1$ is a single bond or $C_1$-$C_6$ alkylene, wherein the alkylene is optionally substituted with one or more substituents selected from the group consisting of $C_1$-$C_6$ alkyl, halogen, hydroxy, mercapto, —$NR_iR_j$, oxo, thio, —$C(O)R_k$, —$C(O)OR_k$, —$C(S)R_k$, nitro, cyano, $C_1$-$C_6$ alkoxy and $C_1$-$C_6$ alkylthio;

$A_2$ is a single bond or $C_1$-$C_6$ alkylene, wherein the alkylene is optionally substituted with one or more substituents selected from the group consisting of $C_1$-$C_6$ alkyl, halogen, hydroxy, mercapto, —$NR_iR_j$, oxo, thio, —$C(O)R_k$, —$C(O)OR_k$, —$C(S)R_k$, nitro, cyano, $C_1$-$C_6$ alkoxy and $C_1$-$C_6$ alkylthio;

each k2 is independently an integer from 1 to 6; each k3 is independently an integer from 0 to 3;

each k4 is independently an integer from 0 to 3; and x is an integer from 1 to 3.

5. The compound or the pharmaceutically acceptable salt, stereoisomer or deuterated compound thereof according to claim 1, wherein

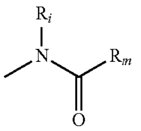

is

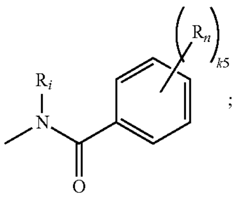

;

each $R_n$ is independently selected from the group consisting of $C_1$-$C_6$ alkyl, hydroxy and halogen, and k5 is an integer from 0 to 5.

6. The compound or the pharmaceutically acceptable salt, stereoisomer or deuterated compound thereof according to claim 1, wherein ring Di is phenyl or naphthyl.

7. The compound or the pharmaceutically acceptable salt, stereoisomer or deuterated compound thereof according to claim 1, wherein $G_2$ is $C_1$-$C_6$ alkylene optionally substituted with one or more substituents selected from the group consisting of $C_1$-$C_6$ alkyl, halogen, hydroxy, mercapto, —$NR_iR_j$, oxo, thio, —$C(O)R_k$, —$C(O)OR_k$, —$C(S)R_k$, nitro, cyano, $C_1$-$C_6$ alkoxy and $C_1$-$C_6$ alkylthio.

8. The compound or the pharmaceutically acceptable salt, stereoisomer or deuterated compound thereof according to claim 1, wherein the compound of formula (I-2) is (II-2)

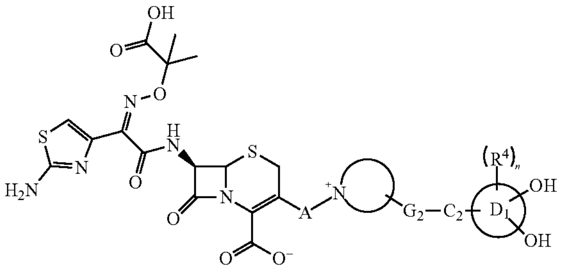

, wherein A,

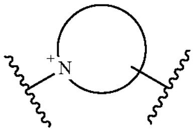

, $G_2$, $C_2$, $D_1$, $R_4$ and n are as described in claim 1.

9. The compound or the pharmaceutically acceptable salt, stereoisomer or deuterated compound thereof according to claim 1, wherein the compound is selected from the group consisting of

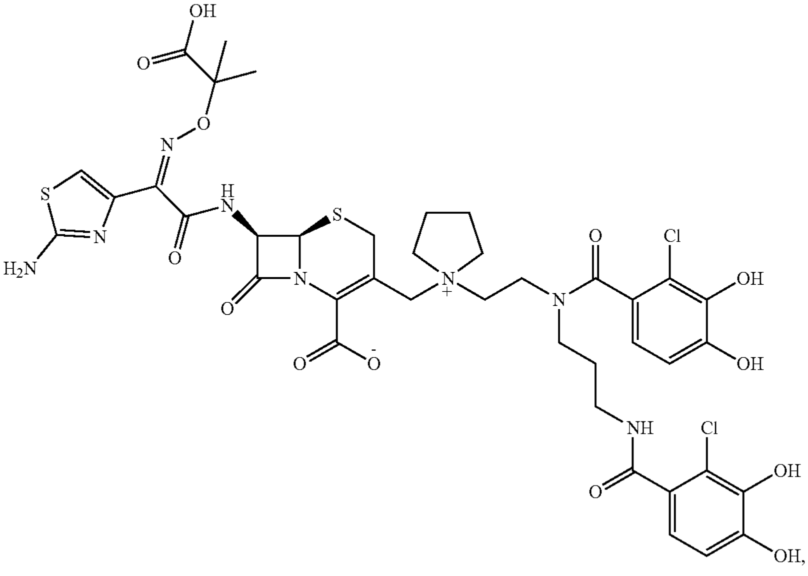 [SMILES: CC(C)(O/N=C(\C(=O)N[C@@H]1C(=O)N2C(C(=O)O)=C(C[N+]3(CCN(CCCNC(=O)c4ccc(O)c(O)c4Cl)C(=O)c4ccc(O)c(O)c4Cl)CCCC3)CS[C@H]12)c1csc(N)n1)C(=O)O]

,

-continued
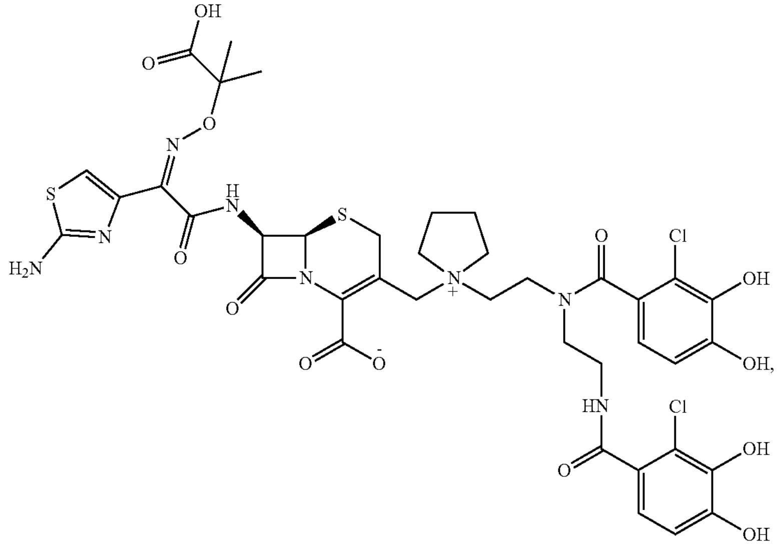
,
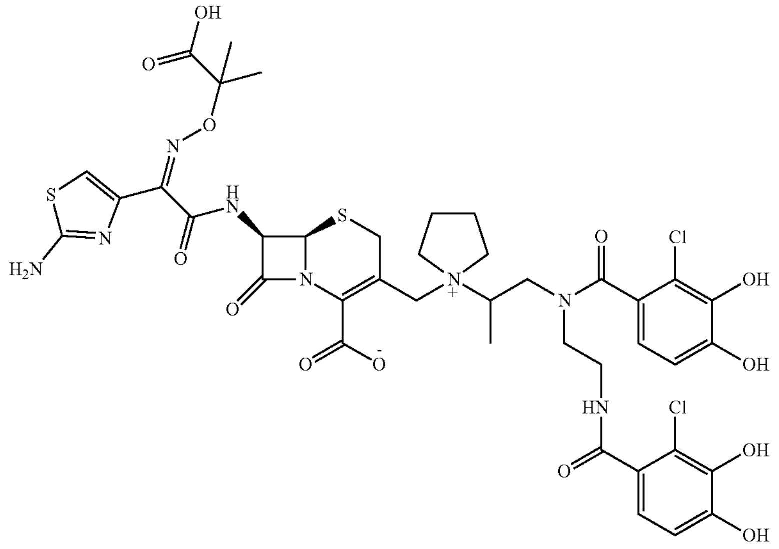
and
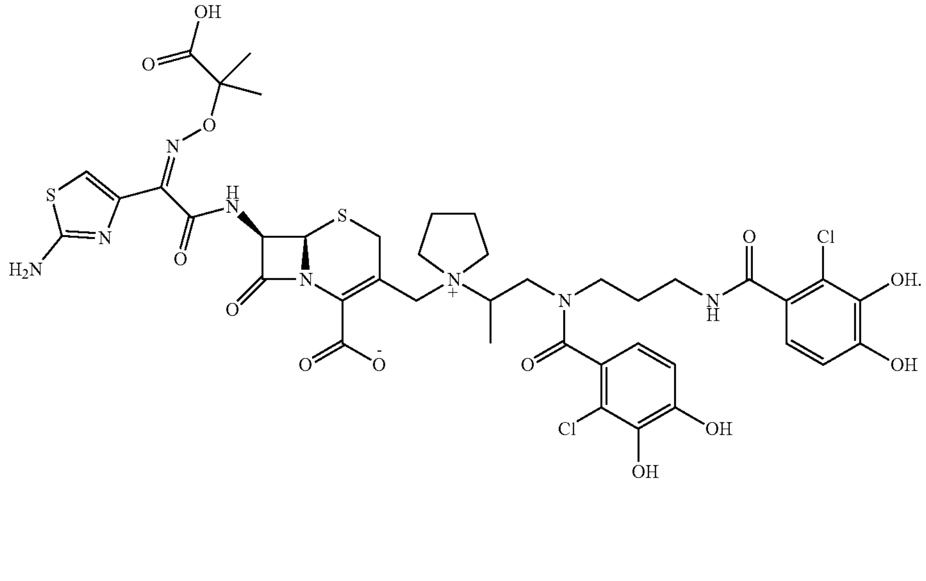 [SMILES: CC(CN(CCCNC(=O)c1ccc(O)c(O)c1Cl)C(=O)c1ccc(O)c(O)c1Cl)[N+]1(CC2=C(C(=O)O)N3C(=O)[C@@H](NC(=O)/C(=N\OC(C)(C)C(=O)O)c4csc(N)n4)[C@H]3SC2)CCCC1]
.

10. The compound or the pharmaceutically acceptable salt, stereoisomer or deuterated compound thereof according to claim 1, wherein

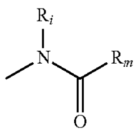

is

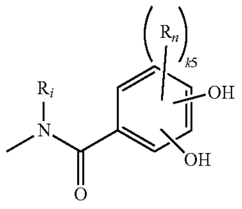

, wherein k5 is an integer from 0 to 3.

11. The compound or the pharmaceutically acceptable salt, stereoisomer or deuterated compound thereof according to claim 1, wherein

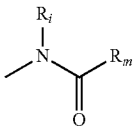

is

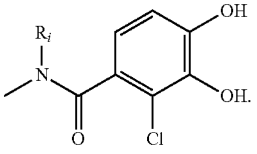

12. A pharmaceutical composition comprising the compound or the pharmaceutically acceptable salt, stereoisomer or deuterated compound thereof according to claim 1, and a pharmaceutically acceptable carrier, diluent, or excipient.

13. A method of treating or preventing a disease caused by gram-negative bacteria or pathogenic bacteria in a subject in need thereof, the method comprising administering to the subject the compound or the pharmaceutically acceptable salt, stereoisomer or deuterated compound thereof according to claim 1.

14. The method according to claim 13, wherein the disease is selected from the group consisting of airway infectious diseases, urinary system infectious diseases, respiratory system infectious diseases, septicemia, nephritis, cholecystitis, oral infectious diseases, endocarditis, pneumonia, bone marrow membrane myelitis, otitis media, enteritis, empyema, traumatic infectious diseases and opportunistic infections.

15. The method according to claim 13, wherein the gram-negative bacteria is selected from the group consisting of *E. coli, Klebsiella, Serratia, Enterobacter, Citrobacter, Morganella, Providencia, Proteus, Haemophilus, Moraxella, Pseudomonas aeruginosa* and *Pseudomonas* other than *P. aeruginosa, Stenotrophomonas, Burkholderia* or *Acinetobacter.*

* * * * *